(12) United States Patent
Leahy et al.

(10) Patent No.: US 8,143,403 B2
(45) Date of Patent: Mar. 27, 2012

(54) CGRP RECEPTOR ANTAGONISTS

(75) Inventors: David K. Leahy, Hightstown, NJ (US); Yu Fan, Highland Park, NJ (US); Lopa V. Desai, Chesterfield, NJ (US); Ronald L. Hanson, Morris Plains, NJ (US); Thorsten Rosner, Berkeley Heights, NJ (US); Guanglin Luo, Madison, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 12/977,275

(22) Filed: Dec. 23, 2010

(65) Prior Publication Data

US 2012/0010402 A1 Jan. 12, 2012

Related U.S. Application Data

(63) Continuation-in-part of application No. 12/415,624, filed on Mar. 31, 2009, now Pat. No. 8,044,043.

(60) Provisional application No. 61/044,198, filed on Apr. 11, 2008.

(51) Int. Cl.
*C07D 221/04* (2006.01)
(52) U.S. Cl. ...................................................... 546/183
(58) Field of Classification Search .................... 546/183
See application file for complete search history.

(56) References Cited

U.S. PATENT DOCUMENTS

2009/0258866 A1  10/2009  Luo

FOREIGN PATENT DOCUMENTS

| WO | WO 2004/092166 | 10/2004 |
| WO | WO 2004/092168 | 10/2004 |
| WO | WO 2007/120590 | 10/2007 |

OTHER PUBLICATIONS

U.S. Appl. No. 61/392,183, filed Oct. 12, 2010, Leahy et al.
U.S. Appl. No. 61/474,567, filed Apr. 12, 2011, Luo et al.
U.S. Appl. No. 12/902,714, filed Oct. 12, 2010, Luo et al.

*Primary Examiner* — Bruck Kifle
(74) *Attorney, Agent, or Firm* — James Epperson

(57) ABSTRACT

The disclosure generally relates to the novel compounds of formula I, including their salts, which are CGRP receptor antagonists. The disclosure also relates to pharmaceutical compositions and methods for using the compounds in the treatment of CGRP related disorders including migraine and other headaches, neurogenic vasodilation, neurogenic inflammation, thermal injury, circulatory shock, flushing associated with menopause, airway inflammatory diseases such as asthma, and chronic obstructive pulmonary disease (COPD).

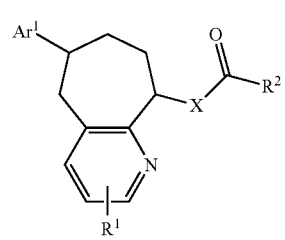

5 Claims, 4 Drawing Sheets

[$^{125}$I]-CGRP Saturation/Scatchard Analysis

Direct Validation of Facial Blood Flow as Surrogate for Intracranial Artery Dilation in the Rat Dose-Response for hαCGRP in Non-Human-Primate Laser Doppler Facial Blood Flow

CGRP RECEPTOR ANTAGONISTS

CROSS-REFERENCE TO RELATED APPLICATIONS

This application is a Continuation-in-Part of U.S. Non-Provisional application Ser. No. 12/415,624 filed Mar. 31, 2009 which claims the benefit of U.S. Provisional Application Ser. No. 61/044,198 filed Apr. 11, 2008.

BACKGROUND OF THE INVENTION

The disclosure generally relates to the novel compounds of formula I, including pharmaceutically acceptable salts, which are CGRP-receptor antagonists. The disclosure also relates to pharmaceutical compositions and methods for using the compounds in the treatment of CGRP related disorders including migraine headaches, neurogenic vasodilation, neurogenic inflammation, thermal injury, circulatory shock, flushing associated with menopause, airway inflammatory diseases such as asthma, and chronic obstructive pulmonary disease (COPD).

Calcitonin gene-related peptide (CGRP) is a naturally occurring 37-amino-acid peptide first identified in 1982 (Amara, S. G. et al, Science 1982, 298, 240-244). Two forms of the peptide are expressed (αCGRP and βCGRP) which differ by one and three amino acids in rats and humans, respectively. The peptide is widely distributed in both the peripheral (PNS) and central nervous system (CNS), principally localized in sensory afferent and central neurons, and displays a number of biological effects, including vasodilation.

When released from the cell, CGRP binds to specific cell surface G protein-coupled receptors and exerts its biological action predominantly by activation of intracellular adenylate cyclase (Poyner, D. R. et al, Br J Pharmacol 1992, 105, 441-7; Van Valen, F. et al, Neurosci Lett 1990, 119, 195-8). Two classes of CGRP receptors, CGRP1 and CGRP2, have been proposed based on the antagonist properties of the peptide fragment CGRP(8-37) and the ability of linear analogues of CGRP to activate CGRP2 receptors (Juaneda, C. et al. TiPS 2000, 21, 432-438). However, there is lack of molecular evidence for the CGRP2 receptor (Brain, S. D. et al, TiPS 2002, 23, 51-53). The CGRP1 receptor has three components: (i) a 7 transmembrane calcitonin receptor-like receptor (CRLR); (ii) the single transmembrane receptor activity modifying protein type one (RAMP1); and (iii) the intracellular receptor component protein (RCP) (Evans B. N. et al., J Biol Chem. 2000, 275, 31438-43). RAMP1 is required for transport of CRLR to the plasma membrane and for ligand binding to the CGRP-receptor (McLatchie, L. M. et al, Nature 1998, 393, 333-339). RCP is required for signal transduction (Evans B. N. et al., J Biol Chem. 2000, 275, 31438-43). There are known species-specific differences in binding of small molecule antagonists to the CGRP-receptor with typically greater affinity seen for antagonism of the human receptor than for other species (Brain, S. D. et al, TiPS 2002, 23, 51-53). The amino acid sequence of RAMP1 determines the species selectivity, in particular, the amino acid residue Trp74 is responsible for the phenotype of the human receptor (Mallee et al. J Biol Chem 2002, 277, 14294-8).

Inhibitors at the receptor level to CGRP are postulated to be useful in pathophysiologic conditions where excessive CGRP receptor activation has occurred. Some of these include neurogenic vasodilation, neurogenic inflammation, migraine, cluster headache and other headaches, thermal injury, circulatory shock, menopausal flushing, and asthma. CGRP receptor activation has been implicated in the pathogenesis of migraine headache (Edvinsson L. CNS Drugs 2001; 15(10): 745-53; Williamson, D. J. Microsc. Res. Tech. 2001, 53, 167-178; Grant, A. D. Brit. J. Pharmacol. 2002, 135, 356-362). Serum levels of CGRP are elevated during migraine (Goadsby P J, et al. Ann Neurol 1990; 28:183-7) and treatment with anti-migraine drugs returns CGRP levels to normal coincident with alleviation of headache (Gallai V. et al. Cephalalgia 1995; 15: 384-90). Migraineurs exhibit elevated basal CGRP levels compared to controls (Ashina M, et al., Pain 2000, 86(1-2):133-8.2000). Intravenous CGRP infusion produces lasting headache in migraineurs (Lassen L H, et al. Cephalalgia 2002 February; 22(1):54-61). Preclinical studies in dog and rat report that systemic CGRP blockade with the peptide antagonist CGRP(8-37) does not alter resting systemic hemodynamics nor regional blood flow (Shen, Y-T. et al, J Pharmacol Exp Ther 2001, 298, 551-8). Thus, CGRP-receptor antagonists may present a novel treatment for migraine that avoids the cardiovascular liabilities of active vasoconstriction associated with non-selective 5-HT1B/1D agonists, 'triptans' (e.g., sumatriptan).

CGRP antagonists have shown efficacy in human clinical trials. See Davis C D, Xu C. *Curr Top Med Chem.* 2008 8(16):1468-79; Benemei S, Nicoletti P, Capone J G, Geppetti P. *Curr Opin Pharmacol.* 2009 9(1):9-14. Epub 2009 January 20; Ho T W, Ferrari M D, Dodick D W, Galet V, Kost J, Fan X, Leibensperger H, Froman S, Assaid C, Lines C, Koppen H, Winner P K. *Lancet.* 2008 372:2115. Epub 2008 Nov. 25; Ho T W, Mannix L K, Fan X, Assaid C, Furtek C, Jones C J, Lines C R, Rapoport A M; *Neurology* 2008 70:1304. Epub 2007 Oct. 3.

The invention provides technical advantages, for example, the compounds are novel and inhibit CGRP. Additionally, the compounds provide advantages for pharmaceutical uses, for example, with regard to one or more of their mechanism of action, binding, inhibition efficacy, target selectivity, solubility, safety profiles, or bioavailability.

CGRP receptor antagonists have been disclosed in PCT publications WO 2004/092166, WO 2004/092168, and WO 2007/120590.

DESCRIPTION OF THE INVENTION

Figure 1:
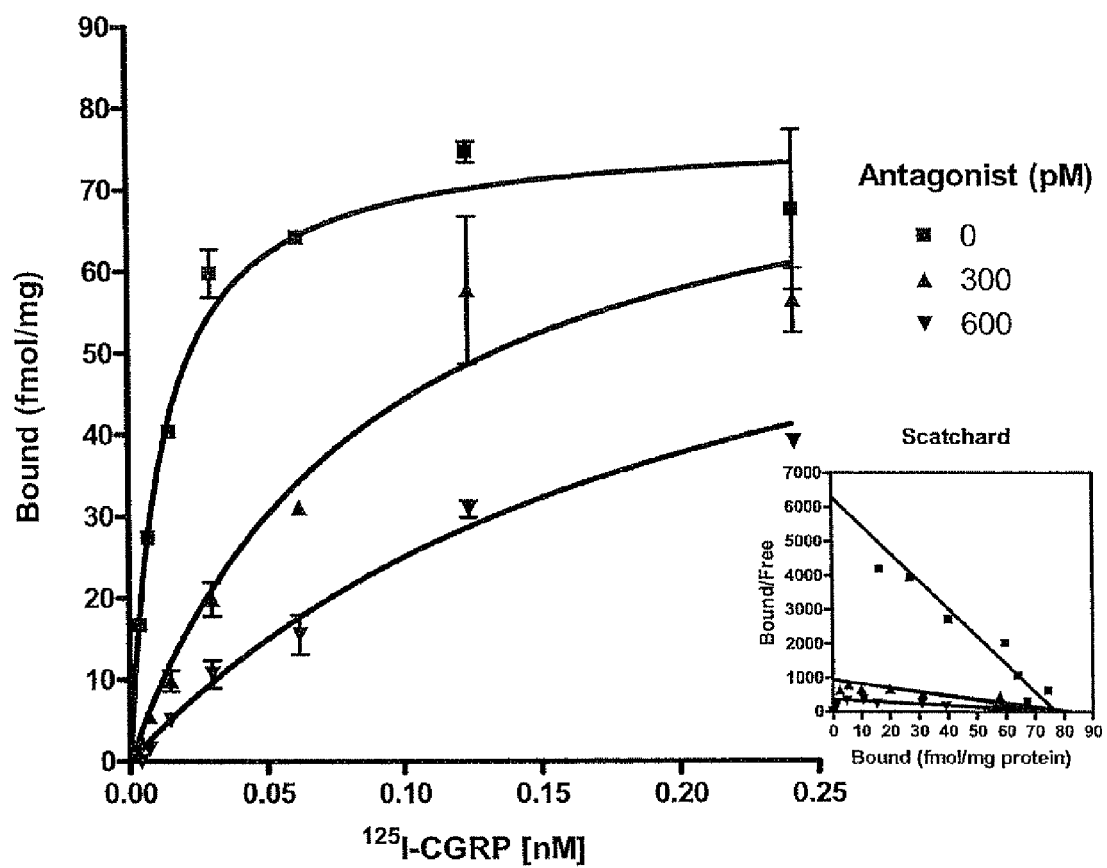
FIG. 1. [$^{125}$I]-CGRP Saturation/Scatchard Analysis. [$^{125}$I]-CGRP saturation using SK-N-MC membranes in the absence (filled squares) and presence (all others) of CGRP antagonist example 20. Inset depicts a Scatchard plot of same data.

The invention encompasses a series of CGRP antagonist compounds including pharmaceutically acceptable salts, compositions, methods of making them, and methods of using them in therapeutic treatment.

One aspect of the invention is a compound of formula I

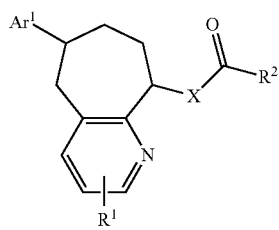

where:

$R^1$ is hydrogen, cyano, halo, alkyl, haloalkyl, alkoxy, haloalkoxy, alkylSO$_2$, amino, alkylamino, dialkylamino, azetidinyl, pyrrolidinyl, piperidinyl, piperazinyl, N-alkylpiperazinyl, or morpholinyl;

$R^2$ is piperidinyl substituted with 1 substituent selected from the group consisting of

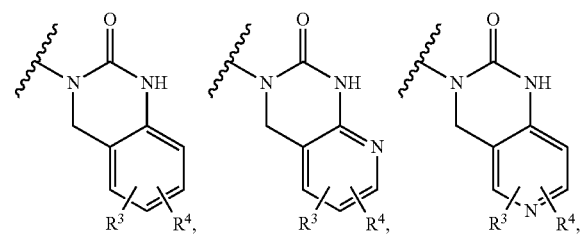

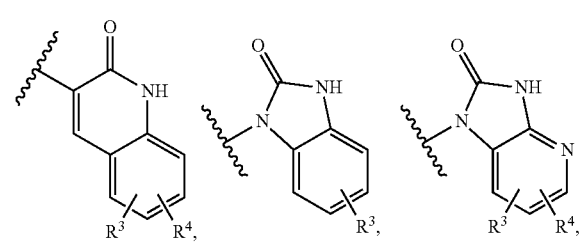

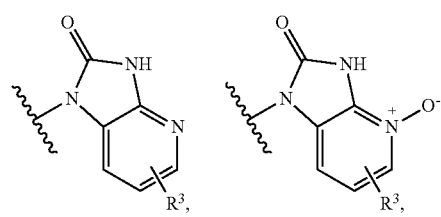 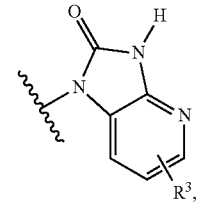

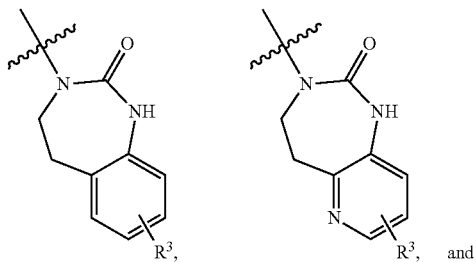

or $R^2$ is

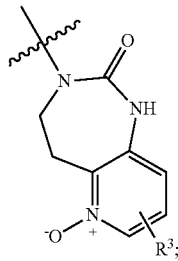

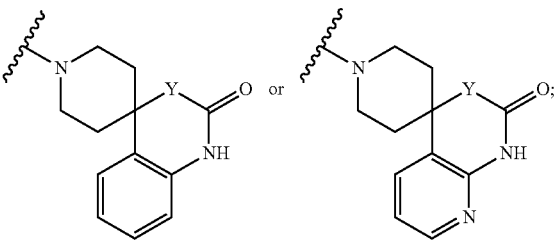

$R^3$ is hydrogen, halo, cyano, alkyl, haloalkyl, alkoxy, or haloalkoxy;

$R^4$ is hydrogen, halo, cyano, alkyl, haloalkyl, alkoxy, or haloalkoxy;

$Ar^1$ is phenyl substituted with 0-3 substituents selected from the group consisting of cyano, halo, alkyl, haloalkyl, alkoxy, haloalkoxy, and alkylSO$_2$;

X is O, CH$_2$, or NH; and

Y is a bond, O, CH$_2$, or NH;

or a pharmaceutically acceptable salt thereof.

Another aspect of the invention is a compound of formula I where $R^1$ is hydrogen, cyano, amino, alkylamino, or dialkylamino;

$R^2$ is piperidinyl substituted with 1 substituent selected from the group consisting of -continued

[chemical structures]

R³, and ;

R³ is hydrogen or halo;
R⁴ is hydrogen or halo;
Ar¹ is phenyl 0-2 halo substituents;
X is O, CH₂, or NH;
and Y is O;
or a pharmaceutically acceptable salt thereof.

Another aspect of the invention is a compound of Formula I where R¹ is hydrogen, cyano, amino, dimethylamino, or t-butylamino; R² is piperidinyl substituted with 1 substituent selected from the group consisting of

[chemical structures]

Ar¹ is phenyl or difluorophenyl; X is O, CH₂, or NH; and Y is O; or a pharmaceutically acceptable salt thereof.

Another aspect of the invention is a compound of formula I where R¹ is hydrogen or cyano.

Another aspect of the invention is a compound of formula I where R² is N-piperidinyl and is 4-substituted.

Another aspect of the invention is a compound of formula I where R² is N-piperidinyl and is 4-substituted with a substituent selected from

[chemical structures]

Another aspect of the invention is a compound of formula I where Ar¹ is phenyl substituted with 2 halo substituents.

Another aspect of the invention is a compound of formula I where Ar¹ is 2,3-difluorophenyl.

Another aspect of the invention is a compound of formula I where X is O.

Another aspect of the invention is a compound of formula I with the following stereochemistry.

[chemical structure]

Another aspect of the invention is a compound of formula II

II

[chemical structure]

where:
R² is piperidinyl and is substituted with 1 substituent selected from the group consisting of

[chemical structures]

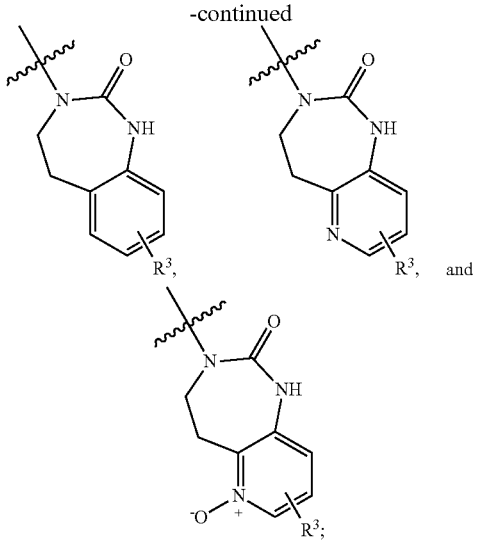

or R² is

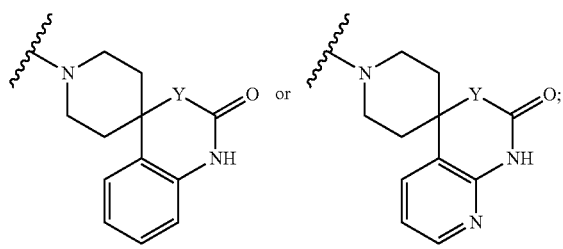

R³ is hydrogen or alkyl;
R⁴ is hydrogen, halo, cyano, alkyl, haloalkyl, alkoxy, or haloalkoxy;
$Ar^1$ is phenyl substituted with 0-3 substituents selected from cyano, halo, alkyl, haloalkyl, alkoxy, and haloalkoxy;
X is O, $CH_2$, or $NR^3$;
Y is a bond, methylene, O, or $NR^3$;
or a pharmaceutically acceptable salt thereof The scope of any instance of a variable, including $R^1$, $R^2$, $R^3$, $R^4$, $Ar^1$, X, and Y, can be used independently with the scope of any other instance of a variable substituent. As such, the invention includes combinations of the different aspects.

Unless specified otherwise, these terms have the following meanings. "Alkyl" means a straight or branched alkyl group composed of 1 to 6 carbons, preferably 1 to 3 carbons. "Alkenyl" means a straight or branched alkyl group composed of 2 to 6 carbons with at least one double bond. "Cycloalkyl" means a monocyclic ring system composed of 3 to 7 carbons. "Hydroxyalkyl," "alkoxy" and other terms with a substituted alkyl moiety include straight and branched isomers composed of 1 to 6 carbon atoms for the alkyl moiety. "Haloalkyl" and "haloalkoxy" include all halogenated isomers from monohalo substituted alkyl to perhalo substituted alkyl. "Aryl" includes carbocyclic and heterocyclic aromatic ring systems. "Amino" includes primary, secondary, and tertiary amine moieties. "Carbonyl" means CO. "Oxy" means —O—. "Aminocarbonyl" means —N(R)C(=O)—. "Oxycarbonyl" means —OC(=O)—. "Methylenecarbonyl" means —CH₂C(=O)—. "Amino(cyano)iminomethyl" means —NHC(=NCN)—. Parenthetic and multiparenthetic terms are intended to clarify bonding relationships to those skilled in the art. For example, a term such as ((R)alkyl) means an alkyl substituent further substituted with the substituent R.

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some compounds of the invention may exist in stereoisomeric forms, one example of which is shown below. The invention includes all stereoisomeric and tautomeric forms of the compounds.

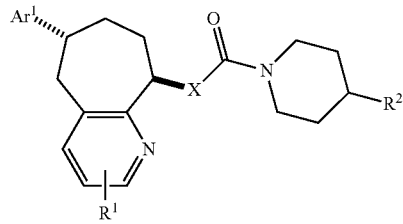

Synthetic Methods

The compounds may be made by methods known in the art including those described below and including variations within the skill of the art. Some reagents and intermediates are known in the art. Other reagents and intermediates can be made by methods known in the art using readily available materials. The following methods are for illustrative purposes and are not intended to limit the scope of the invention. It will be appreciated by those skilled in the art that there are a number of methods available for the synthesis of these compounds and that their synthesis is not limited to the methods provided in the following examples. Variations of the compounds and the procedures to make them which are not illustrated are within the skill of the art. The variables describing general structural formulas and features in the synthetic schemes are distinct from and should not be confused with the variables in the claims or the rest of the specification. These variables are meant only to illustrate how to make some of the compounds of the invention.

Abbreviations used in the schemes generally follow conventions used in the art. Chemical abbreviations used in the specification and examples are defined as follows: "NaHMDS" for sodium bis(trimethylsilyl)amide; "DMF" for N,N-dimethylformamide; "MeOH" for methanol; "NBS" for N-bromosuccinimide; "Ar" for aryl; "TFA" for trifluoroacetic acid; "LAH" for lithium aluminum hydride; "BOC", "DMSO" for dimethylsulfoxide; "h" for hours; "rt" for room temperature or retention time (context will dictate); "min" for minutes; "EtOAc" for ethyl acetate; "THF" for tetrahydrofuran; "EDTA" for ethylenediaminetetraacetic acid; "Et₂O" for diethyl ether; "DMAP" for 4-dimethylaminopyridine; "DCE" for 1,2-dichloroethane; "ACN" for acetonitrile; "DME" for 1,2-dimethoxyethane; "HOBt" for 1-hydroxybenzotriazole hydrate; "DIEA" for diisopropylethylamine, "Nf" for $CF_3(CF_2)_3SO_2-$; and "TMOF" for trimethylorthoformate.

The following schemes exemplify methods that can be used to prepare compounds of formula I. The synthesis described in Scheme I begins with compound III, a literature-known compound prepared from commercially available materials in one step. Reaction of III with an aryl metal reagent such as ArLi or ArMgX can generate IV, which can form V under ring-closure metathesis (RCM). The tertiary alcohol V can be de-hydroxylated to alkene VI, which under standard di-hydroxylation conditions can afford diol VII. Mono-protection of the diol can afford VIII, which can be oxidized to afford the protected hydroxyl ketone IX. Conventional reactions modifying the alcohol, the ketone, or the alpha carbon can lead to additional compounds of Formula I. Alternatively, IX can be modified to generate a variety of fused heterocyclo-cycloheptane derivatives as X. Deprotection can afford the corresponding alcohol XI, which can be activated and reacted with different amines to afford Formula II compound with X=O. XI can also be oxidized to ketone XIII, followed by carbon elongation (Wittig), reduction and hydrolysis to the acid XIV, which by amide formation, can lead to Formula II compounds with X=$CH_2$. Alternatively, alcohol XI can be converted to amines following by urea formation to Formula II compound with X=NH. Scheme 2 provides an alternate procedure for making formula I compounds. This procedure uses a Grubbs cyclization followed by transformation to the ketone which can then introduce an aryl moiety. Further elaboration leads to the alcohol which can then be transformed by methods known in the art.

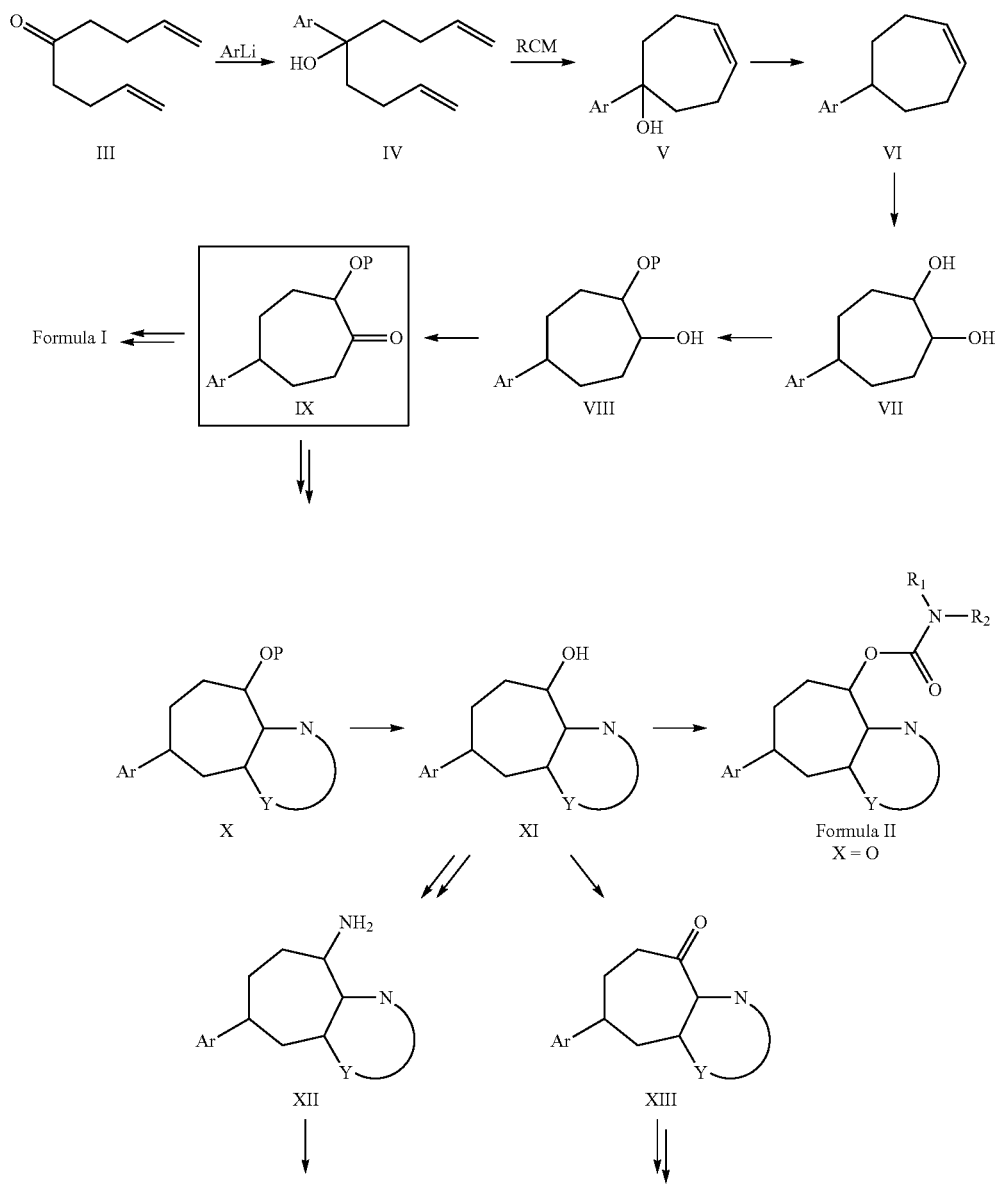

Scheme 1.

11                                                 12
-continued
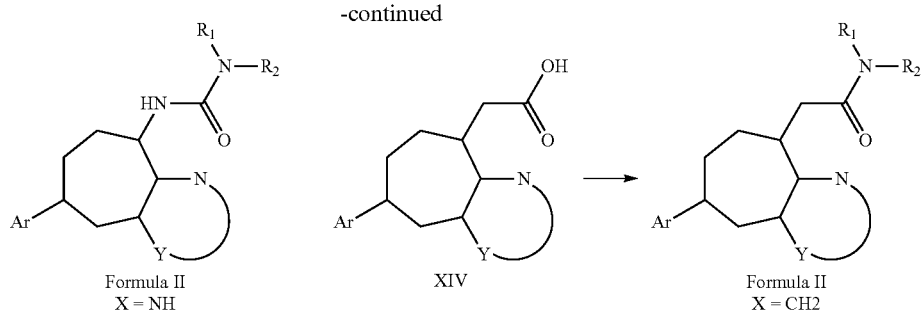
Scheme 2 describes some methods for generating the cycloheptane ring fused a pyrido ring structure using Grubbs cyclization. Further elaboration generates compounds of formula I.
Scheme 2.
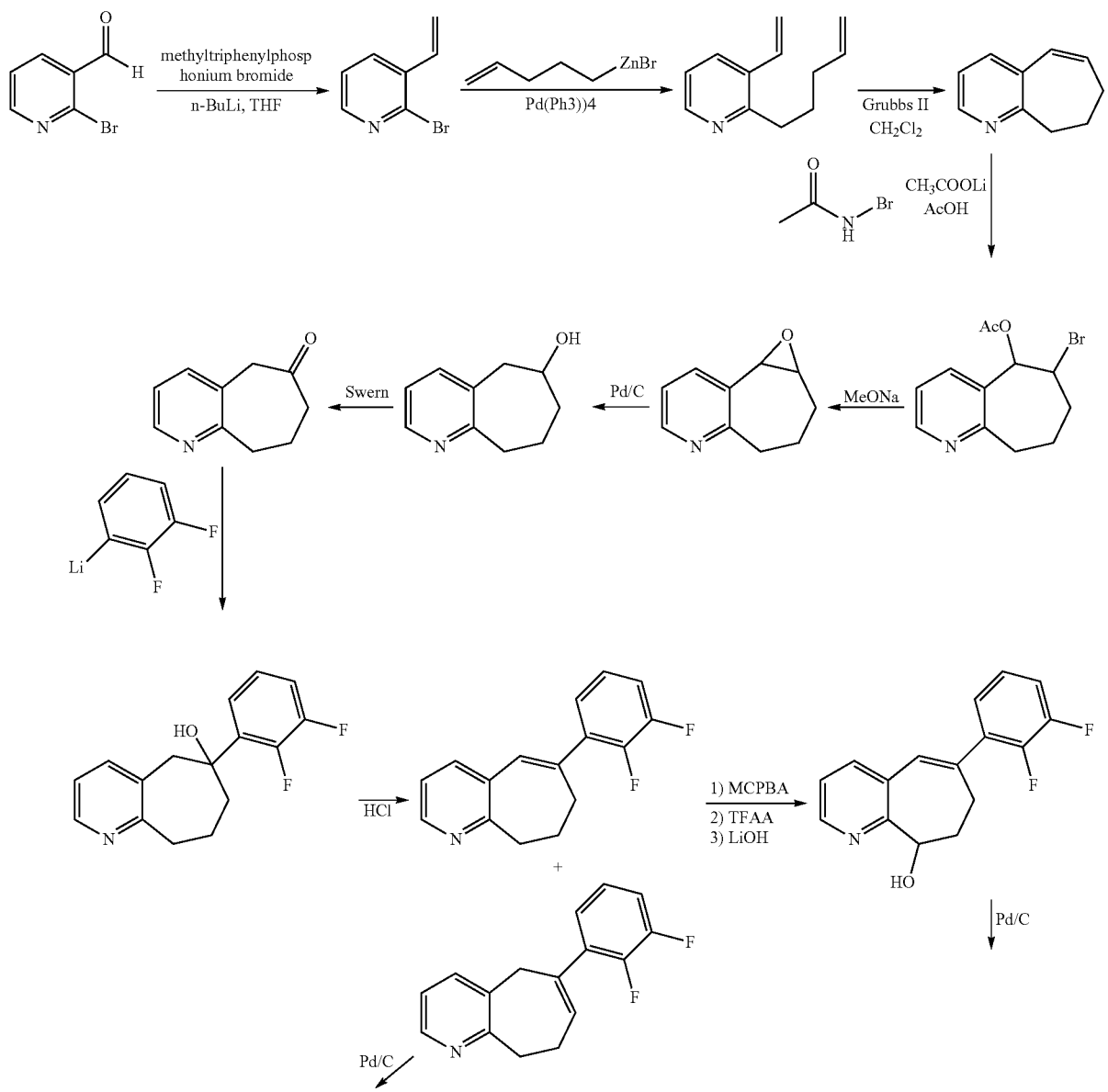

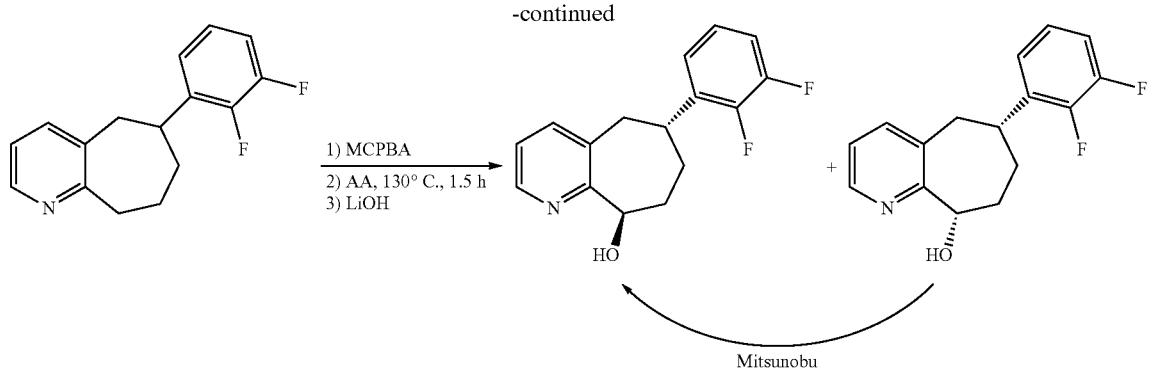
Scheme 3 describes alternative methods for generating the cycloheptane ring fused a pyrido ring structure using Grubbs cyclization. Further elaboration generates compounds of formula I.
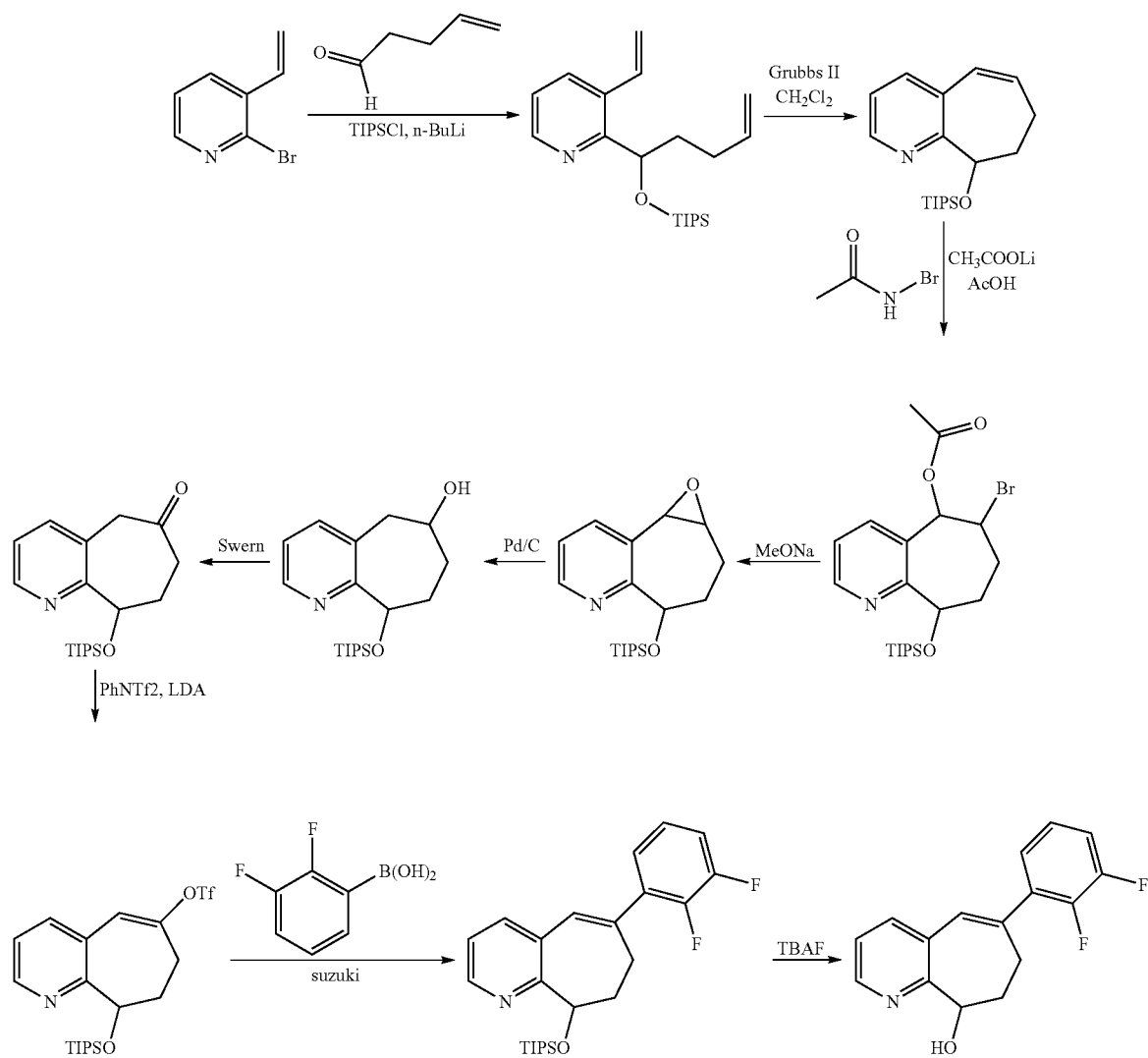

Scheme 2 describes an alternative method for generating the cycloheptane ring fused a pyrido ring structure followed by selective reduction of the diketo intermediate. Further elaboration generates compounds of formula I.
Scheme 4.
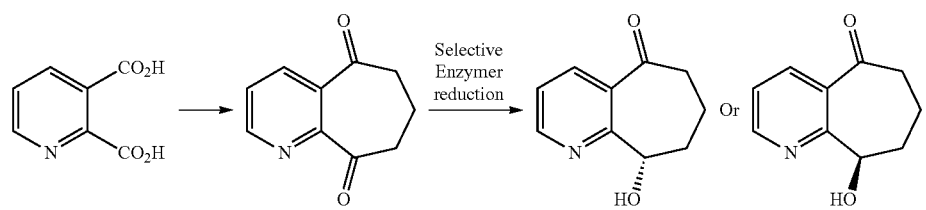
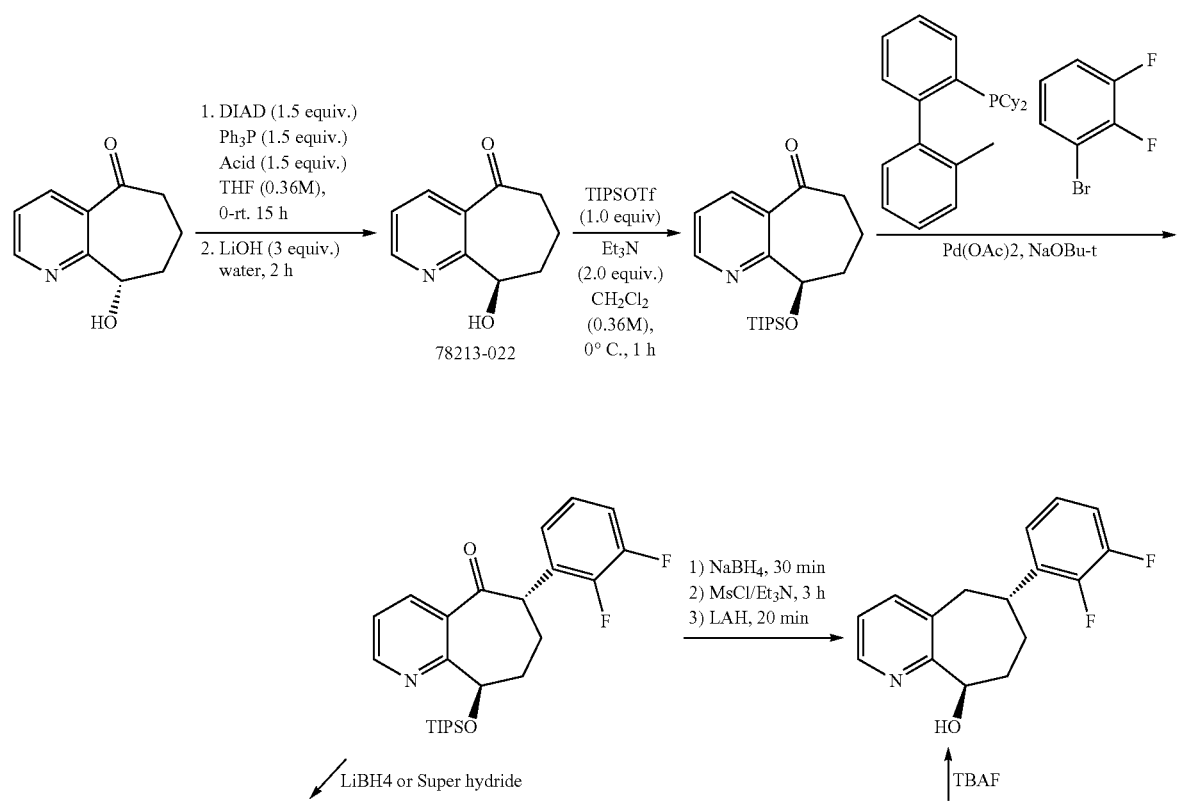
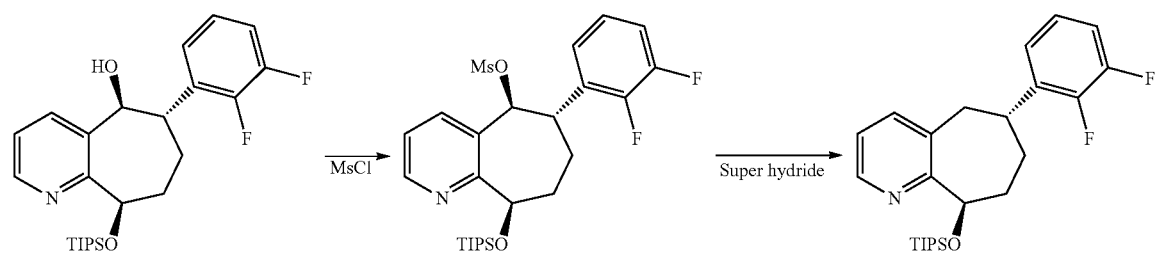

Scheme 5 describes a method for generating compounds of formula I with a carbon linker to the fused pyridocycloheptane core.
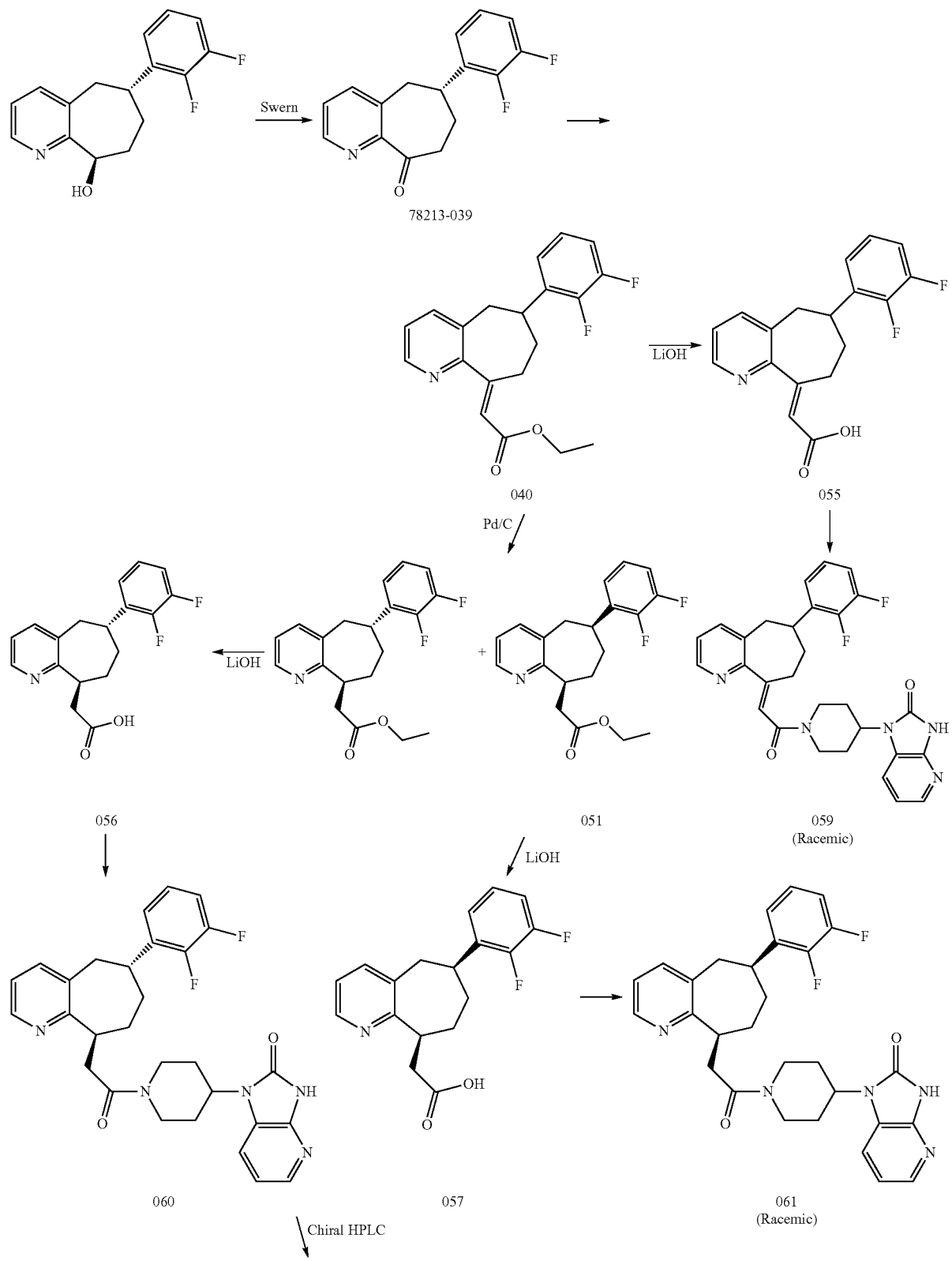
Scheme 5.

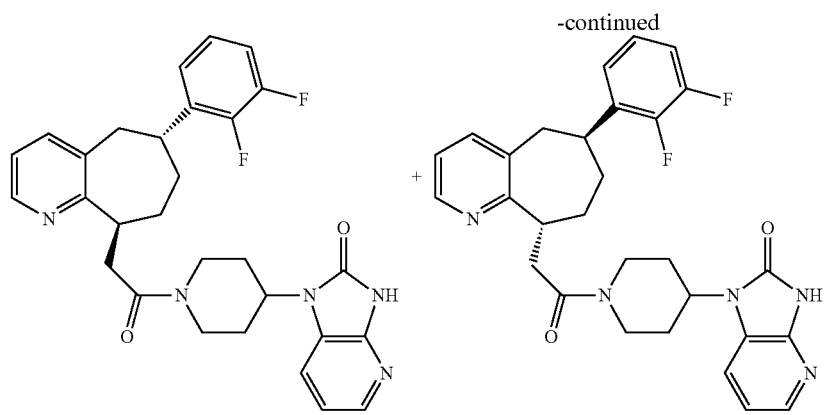
Scheme 6 describes some methods for generating additional substituents on the fused pyridocycloheptane core. Further elaboration generates compounds of formula I.
Scheme 6.
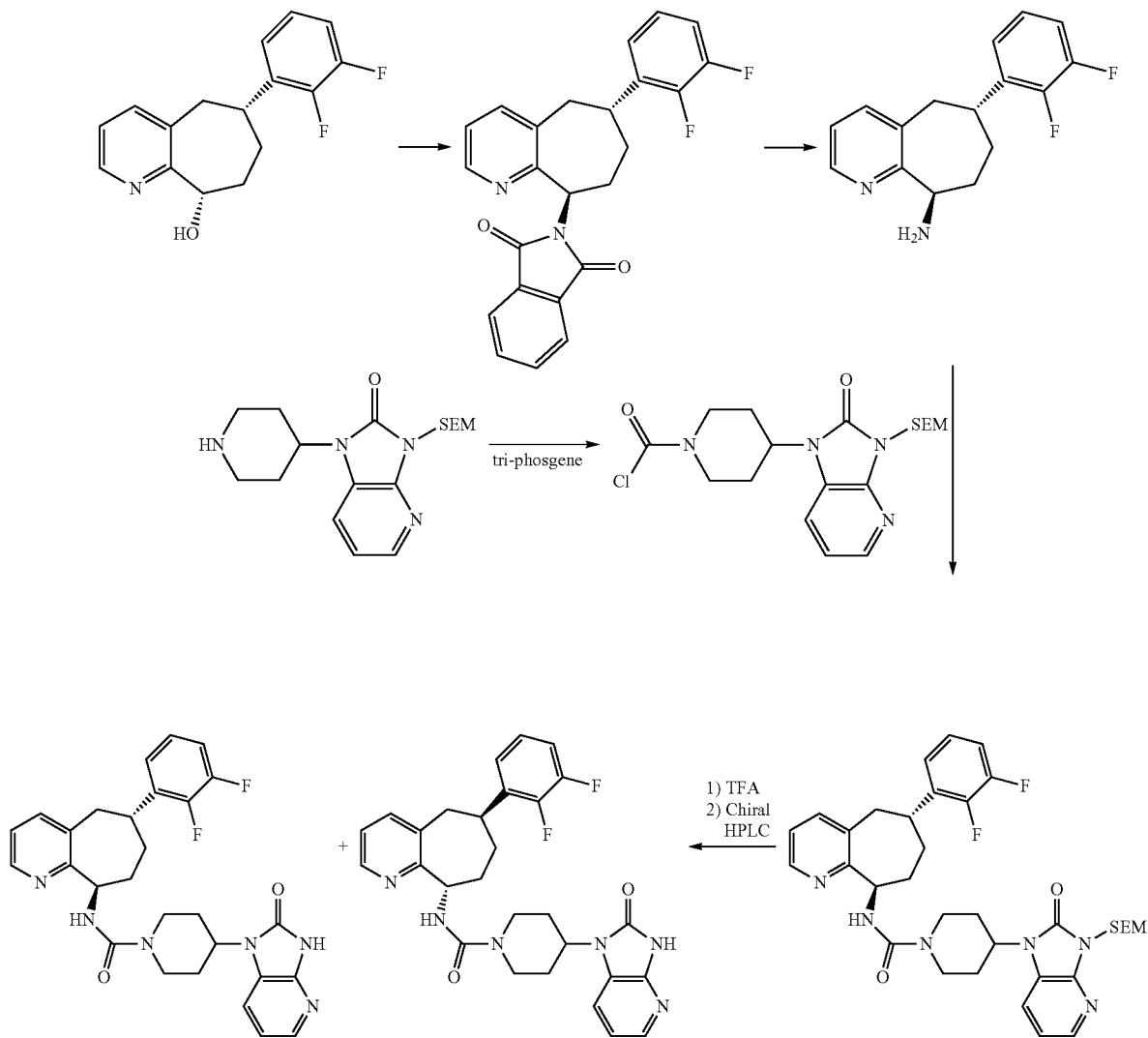

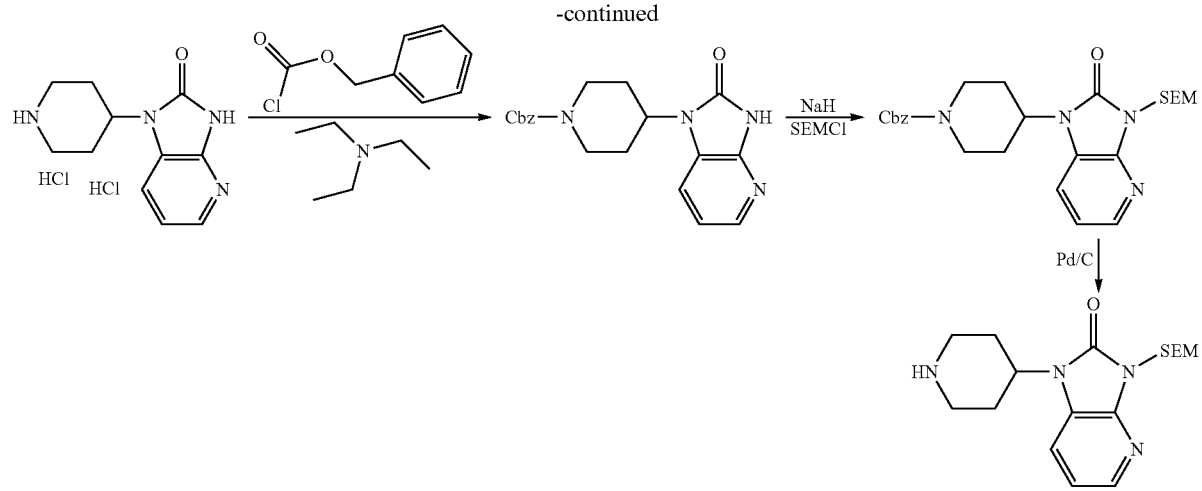
Scheme 7 describes some methods for generating additional aryl substituents on the fused pyridocycloheptane core. Further elaboration generates compounds of formula I.
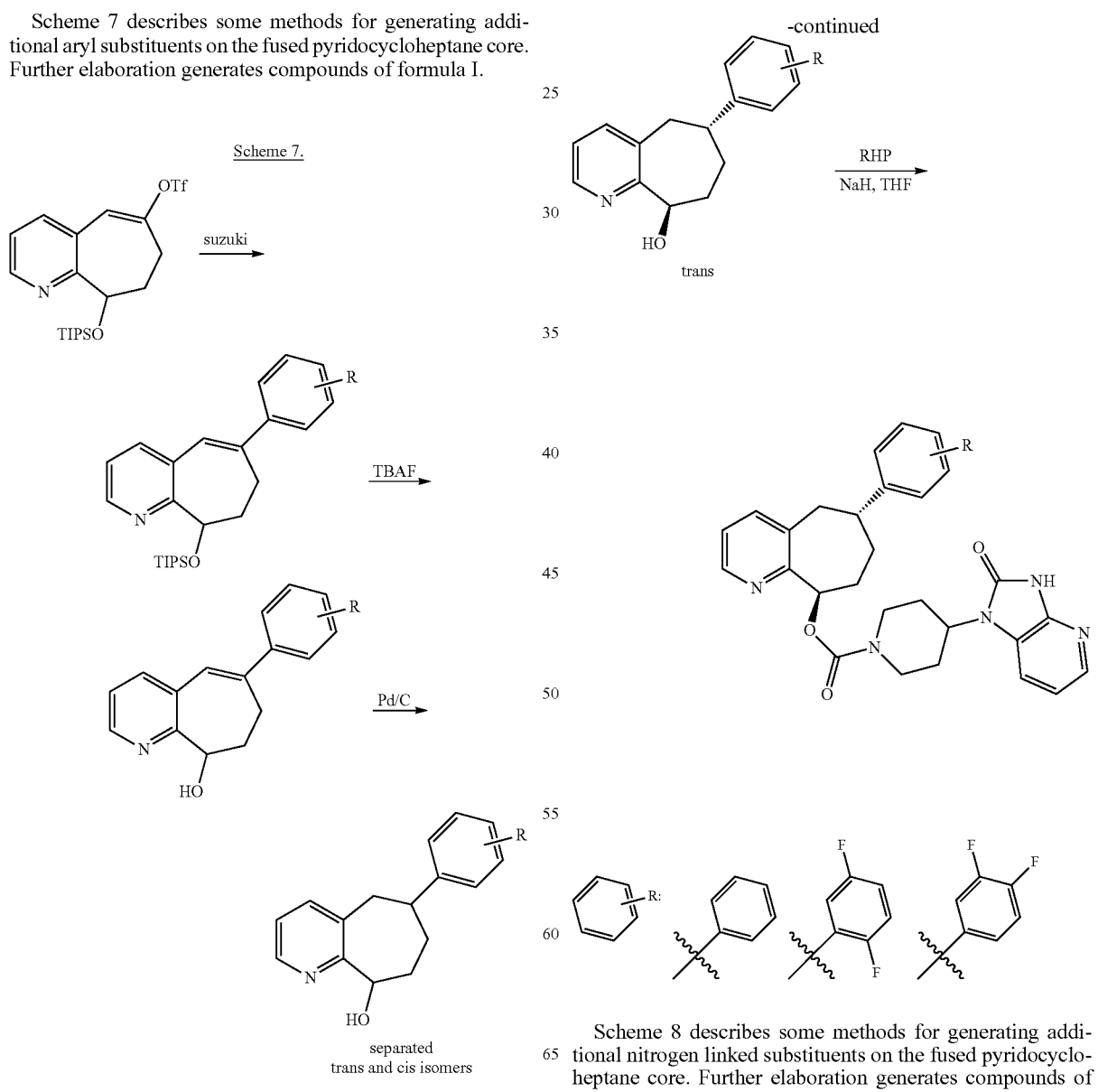
Scheme 8 describes some methods for generating additional nitrogen linked substituents on the fused pyridocycloheptane core. Further elaboration generates compounds of formula I.

Scheme 8.
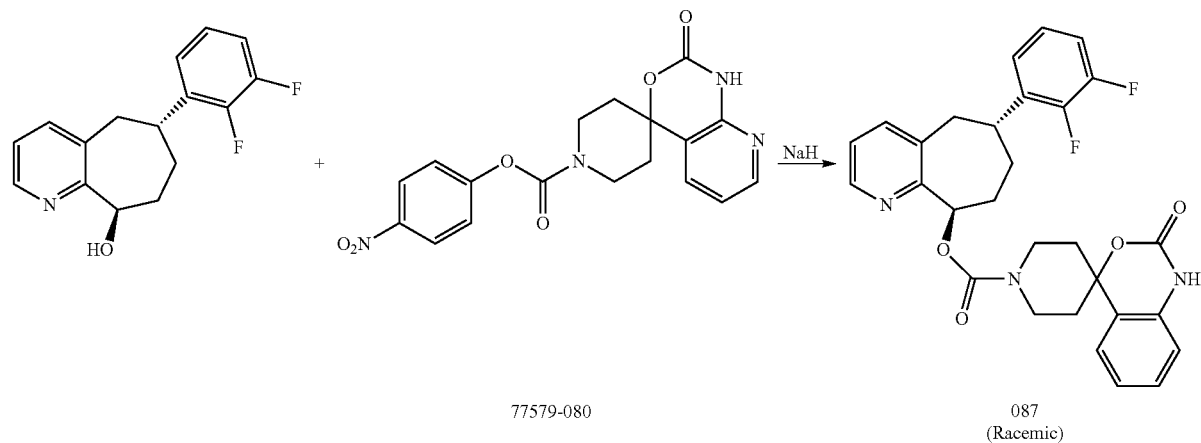
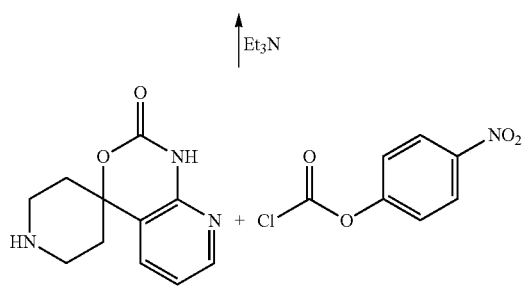
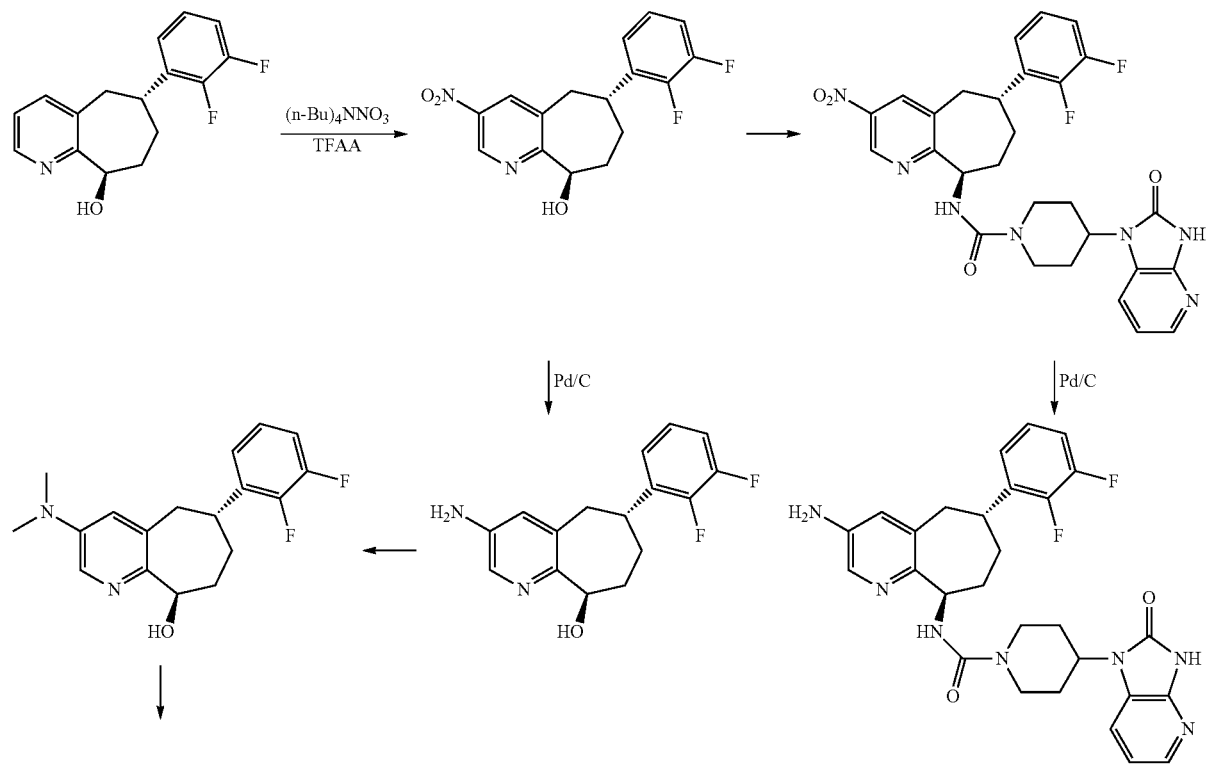

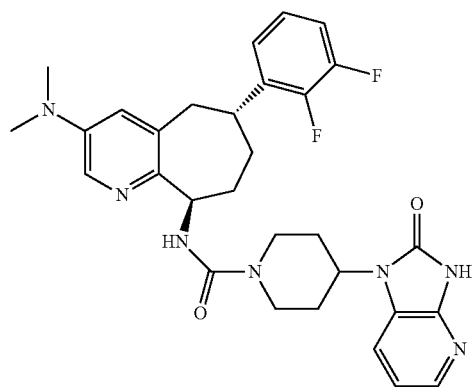
Scheme 9 describes some methods for generating N-oxide analogs of the pyridocycloheptane core. Further elaboration generates compounds of formula I.
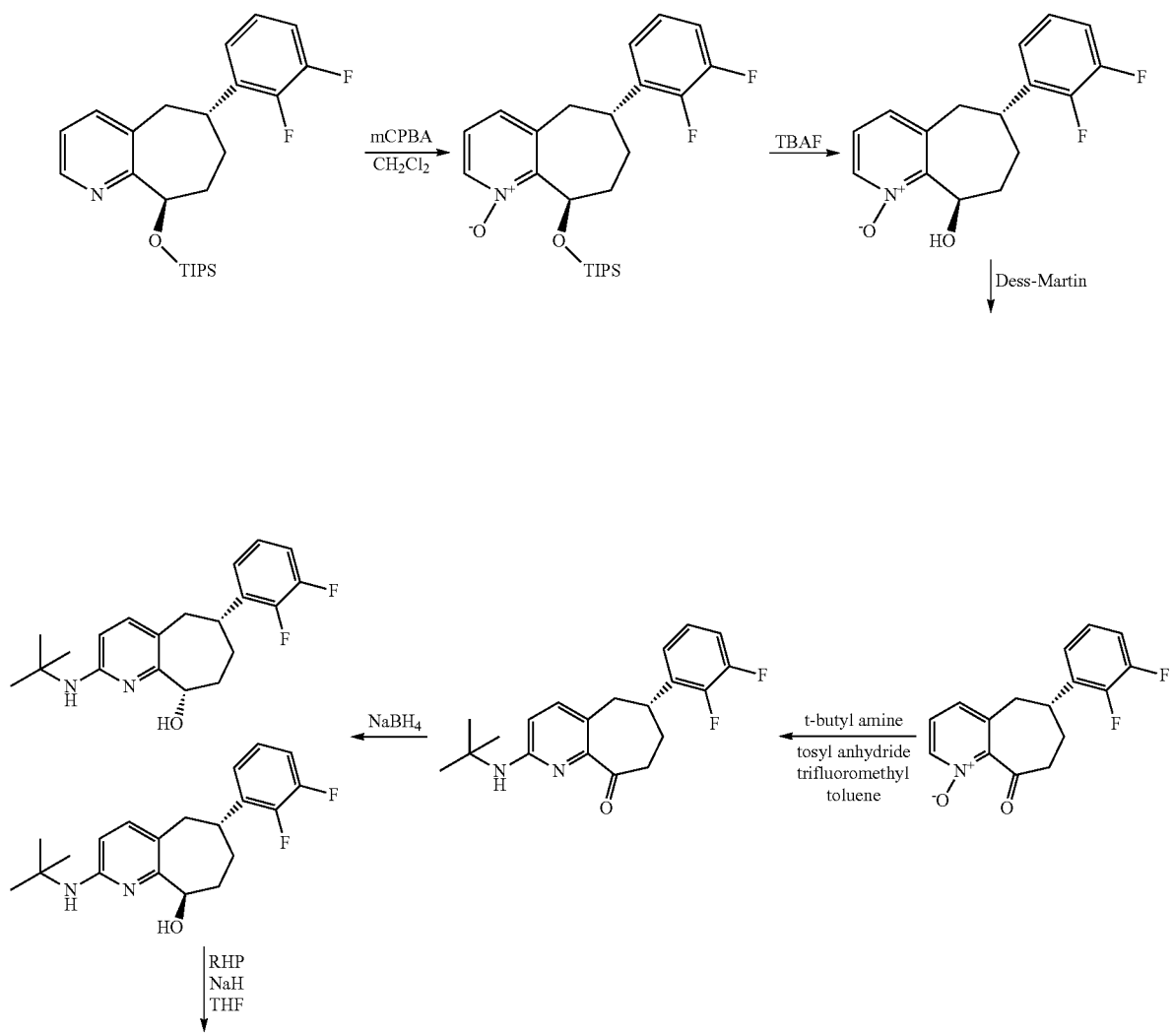
Scheme 9.

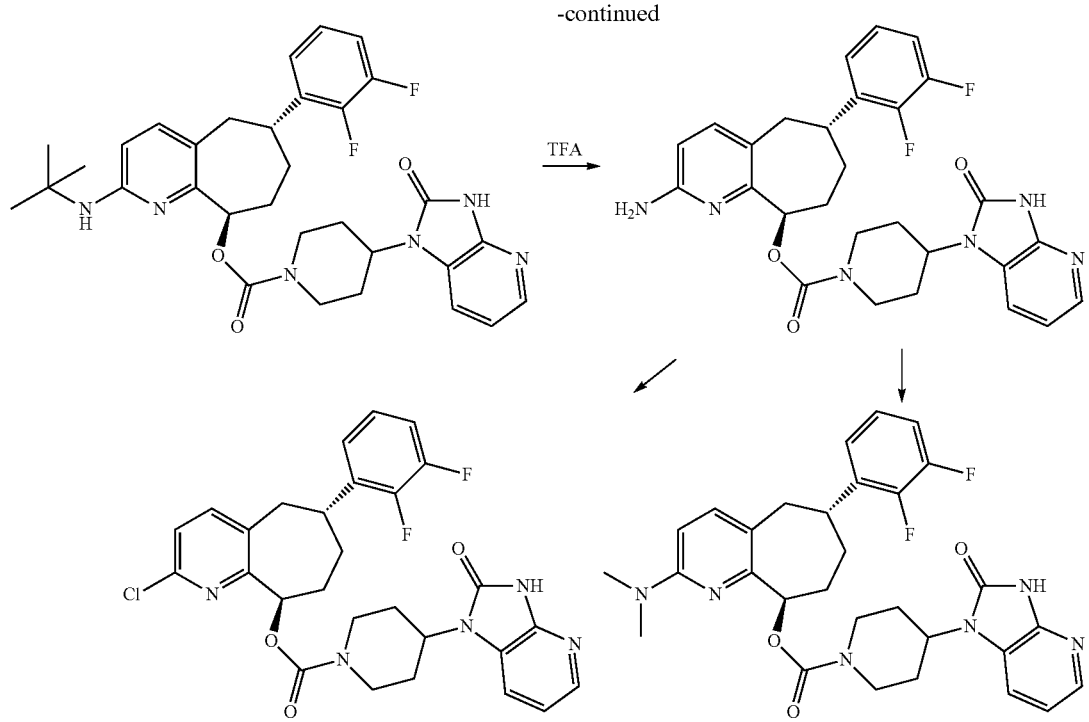

Biological Methods

In Vitro Pharmacology.

Tissue Culture. SK-N-MC cells were grown at 37° C. in 5% $CO_2$ as a monolayer in medium consisting of MEM with Earle's salts and L-glutamine (Invitrogen) supplemented with 10% fetal bovine serum (Invitrogen).

Membrane Preparation. Crude membranes were prepared from SK-N-MC cells expressing CGRP receptors. The cells were rinsed twice with phosphate-buffered saline (155 mM NaCl, 3.3 mM $Na_2HPO_4$, 1.1 mM $KH_2PO_4$, pH 7.4), and incubated for 5-10 min. at 4° C. in hypotonic lysis buffer consisting of 10 mM Tris (pH 7.4) and 5 mM EDTA. The cells were transferred from plates to polypropylene tubes (16×100 mm) and homogenized using a polytron. Homogenates were centrifuged at 32,000×g for 30 min. The pellets were resuspended in cold hypotonic lysis buffer with 0.1% mammalian protease inhibitor cocktail (Sigma) and assayed for protein concentration. The SK-N-MC homogenate was aliquoted and stored at −80° C.

Radioligand Binding Assay. The compounds of invention were solubilized and carried through serial dilutions using 100% DMSO. Aliquots from the compound serial dilutions were further diluted 25 fold into assay buffer (50 mM Tris-Cl pH 7.5, 5 mM $MgCl_2$, 0.005% Triton X-100) and transferred (volume 50 µl) into 96 well assay plates. [$^{125}$I]-CGRP (GE Healthcare or Perkin-Elmer) was diluted to 72 pM in assay buffer and a volume of 50 µl was added to each well. SK-N-MC membranes were thawed, diluted in assay buffer with fresh 0.1% mammalian protease inhibitor cocktail (Sigma), and re-homogenized. SK-N-MC homogenate (7 µg/well) was added in a volume of 100 µl. The assay plates were then incubated at room temperature for 2 h. Assays were stopped by addition of excess cold wash buffer (50 mM Tris-Cl pH 7.5, 0.1% BSA) immediately followed by filtration over glass fiber filters (Whatman GF/B) previously soaked in 0.5% PEI. Non-specific binding was defined with 1 µM beta-CGRP (Bachem). Protein bound radioactivity was determined using a gamma or scintillation counter. The resulting data was analyzed using a four parameter competitive binding equation (XLfit v2.0) and the $IC_{50}$ was defined as the concentration of a compound of invention required to displace 50% of radio-ligand binding. Final assay concentration of [$^{125}$I]-CGRP was 18 pM. The mean Kd for [$^{125}$I]-CGRP is 25.4 pM. All compounds of invention were evaluated in at least two separate experiments. See table 1 for data summary.

TABLE 1

Human CGRP Binding

| Example | Human CGRP Receptor $IC_{50}$ (nM) |
|---|---|
| 1 | 2.86 |
| 2 | 0.23 |
| 3 | 1.25 |
| 4 | 0.44 |
| 5 | 4.04 |
| 6 | 0.89 |
| 7 | >100 |
| 8 | 1.60 |
| 9 | >1000 |
| 10 | 8.89 |
| 11 | 4.14 |
| 12 | 7.41 |
| 13 | 1.55 |
| 14 | 0.25 |
| 15 | 0.98 |
| 16 | 6.96 |
| 17 | 0.80 |
| 18 | 0.78 |
| 19 | 0.76 |
| 20 | 0.12 |
| 21 | 0.12 |

Saturation/Scatchard Analysis. The nature of the interaction between the human CGRP peptide and example 20 was studied in detail using saturation binding experiments. The binding of increasing concentrations of [$^{125}$I]-CGRP to SK-N-

MC cell membranes was measured in the absence (control condition) and in the presence of 300 pM and 600 pM example 20. Saturation data were analyzed using a one site binding equation to estimate apparent equilibrium dissociation constant ($K_d$) and the maximum number of binding sites ($B_{max}$) (Prizm v4.0, Graphpad). The impact of the addition of example 20 to the binding parameters ($K_d$, $B_{max}$) of [$^{125}$I]-CGRP binding was measured and compared. Example 20 dose-dependently increased the $K_d$ of [$^{125}$I]-CGRP binding, without significantly changing the maximum binding sites of [$^{125}$I]-CGRP binding ($B_{max}$). This is indicative of a competitive mechanism of inhibition of binding of [$^{125}$I]-CGRP by example 20. Example 20 was evaluated in 3 separate experiments (for representative dataset, see FIG. 1. [$^{125}$I]-CGRP Saturation/Scatchard Analysis).

Figure 2:
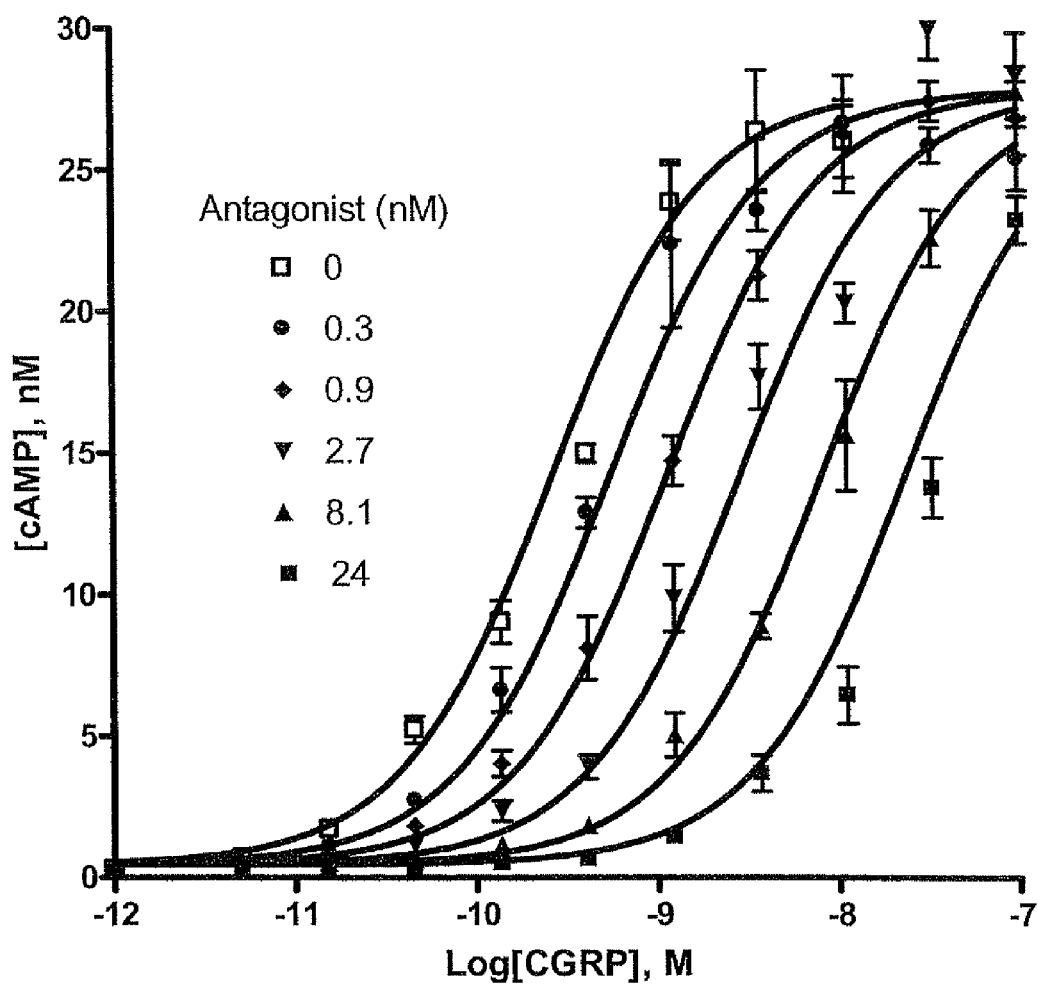
FIG. 2. Functional Antagonism/Schild Analysis. CGRP dose response (stimulated cAMP production) in SK-N-MC cells in the absence (open squares) and presence (all others) of increasing concentrations (left-to-right, 0.3 to 24 nM) of the CGRP antagonist example 20.

Functional Antagonism/Schild analysis. Agonist stimulation of CGRP receptor complex leads to cyclic AMP (adenosine 3'5'-cyclic monophosphate) production via Gs-dependent activation of an adenylate cyclase (Juaneda C et al., TiPS, 2000; 21:432-438). Consequently, CGRP receptor antagonists inhibit CGRP-induced cyclic AMP formation in SK-N-MC cells which natively express the CGRP receptor complex (Doods H et al., Br J Pharmacol, 2000; 129(3):420-423). Example 20 was evaluated for its ability to block CGRP induced cAMP formation using a commercially available cAMP HTRF kit (catalog number 62AM2PEC, CisBio International). A Schild analysis format was used, which allowed investigation of the mechanism of antagonism. In this format the dose response of CGRP stimulated cAMP production was generated with CGRP alone and in the presence of various concentrations of example 20. Briefly, example 20 was pre-incubated with SK-N-MC cells for 15 minutes. Various concentrations of CGRP were added and the cells were allowed to incubate 30 min at room temperature. The cells were lysed with lysis reagent and cAMP concentrations were determined by HTRF according to the manufacturer's instructions. A standard curve using known quantities of cAMP was evaluated in parallel to allow conversion of HTRF ratio to nM cAMP. The resulting curves were then evaluated using a Gaddum/Schild equation individually and with global fitting (Prizm v4.0, Graphpad). Example 20 caused a right shift in the CGRP EC50, without altering the maximal response. To obtain a global fit the following parameters were shared (top, bottom, logEC50, Hill slope and pA2) and all curves were fit simultaneously. Global fits for two separate experiments using unconstrained Schild slopes returned Schild slope values of 1.17 and 0.8, consistent with the expected Schild slope of ~1 for simple competitive antagonists (for methodology see Moltulsky et al., 2003, Graphpad Software Inc.). The mean $K_b$ for both example 20 datasets (using Schild slope of 1) is 247±40 pM (for representative global fit data set for example 20 plotted with Schild slope of 1, see FIG. 2. Functional Antagonism/Schild Analysis).

Figure 3:
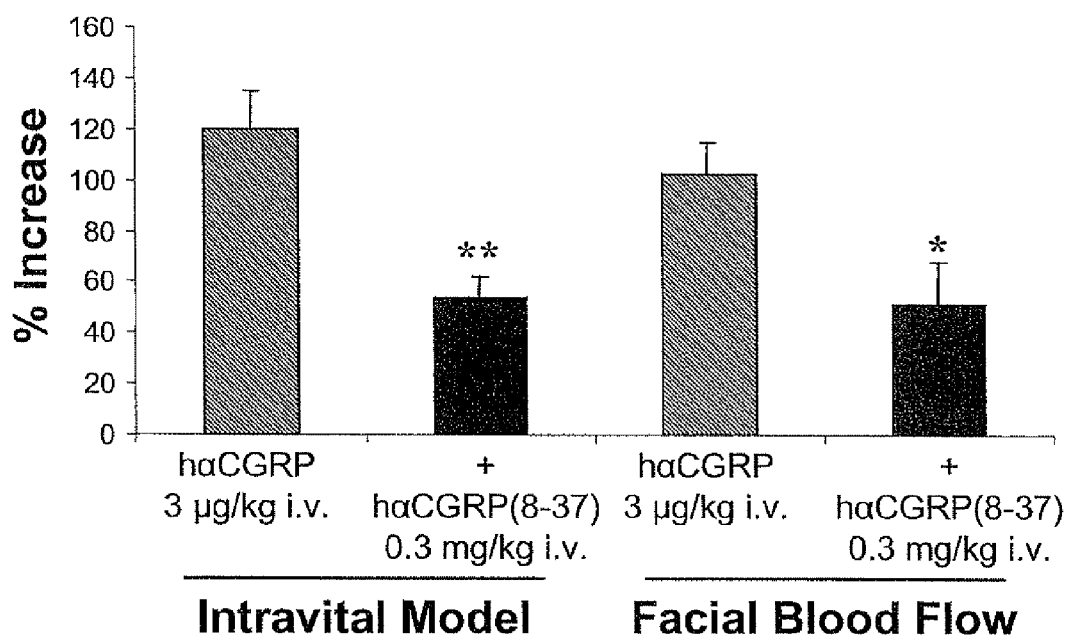
FIG. 3. Direct Validation of Facial Blood Flow as Surrogate for Intracranial Artery Dilation in the Rat. Intravenous delivery of i.v. hαCGRP induces comparable percent increases (100-120% of baseline) in rat middle meningeal artery diameter and rat facial blood flow (left and right striped bars, respectively). Pretreatment with the peptide antagonist CGRP(8-37) produces a 50% inhibition of subsequent i.v. hαCGRP administration for both measures (filled bars). Intracranial artery diameter and facial blood flow were measured concurrently in each animal (n=5 rats). Data are mean±sem * $p<0.05$, ** $p<0.01$ vs corresponding hαCGRP alone.
Figure 4:
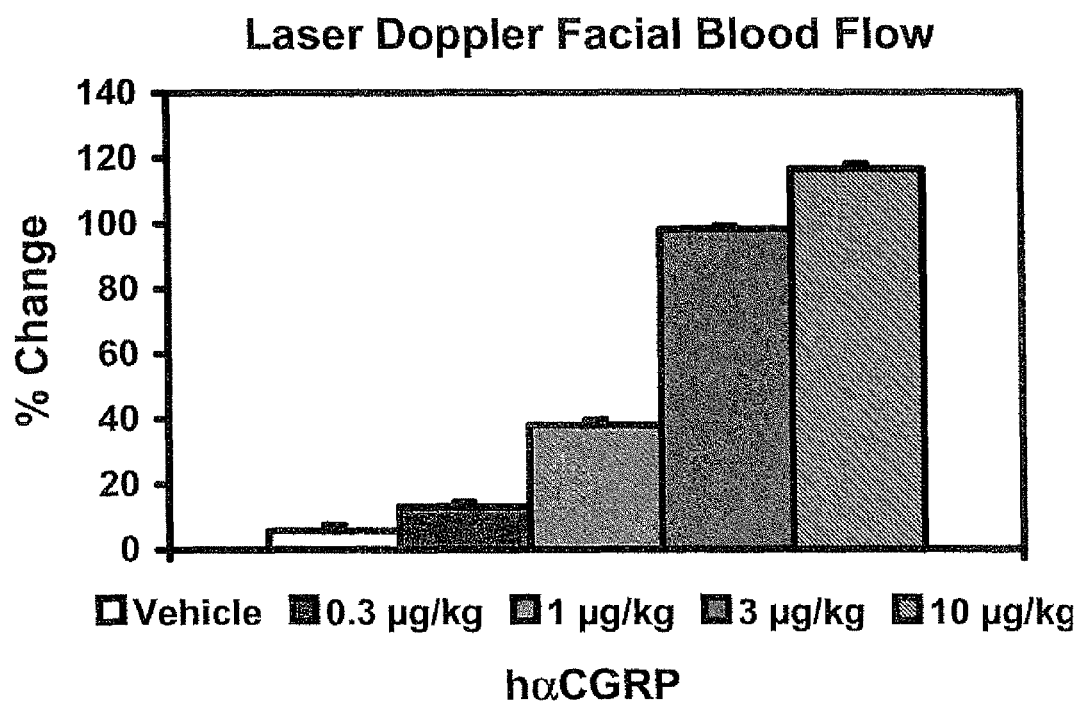
FIG. 4. Dose-Response for hαCGRP in Non-Human-Primate Laser Doppler Facial Blood Flow. Delivery of hαCGRP (i.v.) induces dose-dependent increase in laser Doppler facial blood flow in non-human primates (e.g., common marmoset). Animals (n=6) received increasing doses of hαCGRP at 30 min intervals. Data are peak % change from baseline±sem, with each animal serving as its own control.

Non-Terminal Method for Assessing In Vivo Efficacy of Small Molecule CGRP-Receptor Antagonists in Mammals Overview. Blocking the cascade of events induced by calcitonin gene-related peptide (CGRP), including neurogenic vasodilation of intracranial arteries, has been proposed as a treatment for migraine headache (Edvinsson et al CNS Drugs 2001 15:745; Benemei et al Curr Opin Pharmacol 2009 9:9), however, novel small molecule CGRP-receptor antagonists have shown species-specific differences with relatively poor activity in rodents (Mallee et al. J Biol Chem 2002 277: 14294) requiring new models for assessment of in vivo efficacy. Non-human primates (e.g., marmosets) are the only animals known to have human-like CGRP receptor pharmacology conferred by the presence of the specific amino acid residue (Trp74) in their RAMP1 sequence which is responsible for the phenotype of the human receptor (Mallee et al. J Biol Chem 2002 277:14294). Since current migraine models primarily use rats (Escott et al. Brain Res 1995 669:93; Williamson et al. Cephalalgia 1997 17:525), or are invasive, terminal procedures in primates (Doods et al. Br J Pharmacol 2000 129:420), a novel non-invasive, survival model in non-human primates for in vivo efficacy assessment of CGRP-receptor antagonists was developed. While it is known that trigeminal activation increases both intracranial (Goadsby & Edvinsson, 1993) and facial blood flow (Doods et al., 2000), demonstration of a direct relationship between facial blood flow and intracranial artery dilation conducted in the same animals was not known. Therefore, before initiating studies in non-human primates, laser Doppler measurement of facial blood flow was directly validated in the rat as a surrogate for intracranial artery dilation in terminal studies that measured both intracranial artery diameter and changes in facial blood flow in the same animals (see FIG. 3. Direct Validation of Facial Blood Flow as Surrogate for Intracranial Artery Dilation in the Rat). In both measures, comparable increases were induced by i.v. CGRP and blocked by the peptide antagonist hαCGRP(8-37). Next, the method of i.v. CGRP-induced changes in facial blood flow was validated as a recovery model in isoflurane anesthetized rats using hαCGRP(8-37). This rodent survival method was then established in non-human primates and a dose-response study characterizing i.v. CGRP activity was completed (see FIG. 4. Dose-Response for hαCGRP in Non-Human-Primate Laser Doppler Facial Blood Flow). Peptide and small-molecule CGRP-receptor antagonists were used to validate the non-human primate model. Pre-treatment with small molecule antagonists or hαCGRP(8-37) dose-dependently inhibited i.v. CGRP-stimulated increases in primate facial blood flow (see Table 2. Inhibition of CGRP-Induced Increase in Laser Doppler Facial Blood Flow in the Non-Human Primate (e.g., Common Marmoset)). Post-treatment of antagonists also reversed CGRP-induced increases in facial blood flow (not shown). This survival model provides a novel, non-invasive recovery procedure for evaluating prophylactic and abortive effects of CGRP-receptor antagonists in non-human primates, or in transgenic animals with humanized RAMP1 (Trp74) which have similar CGRP receptor pharmacology, as a surrogate marker for activity in intracranial artery diameter.

Animals. Adult male and female common marmosets (*Callithrix jacchus*) purchased from Harlan and weighing 350-550 g served as subjects.

Anesthesia & Surgical Preparation. Animals are anesthetized by isoflurane inhalation in an induction chamber (4-5% rapid induction, maintained with 1-2.5%; Solomon et al., 1999). Anesthesia is maintained by delivering a constant supply of air:oxygen (50:50) and isoflurane via face mask, or by intubation and ventilation (with blood gas monitoring). Body temperature is maintained at 38±0.5° C. by placement on an automated temperature controlled surface with rectal probe. A small area of fur (approx. 1.5 cm square) is removed from one or both sides of the face by application of a depilatory cream and/or shaving. Surgical areas are clipped and prepared with betadine. An i.v. line is placed in any accessible vein (e.g, saphenous) for the administration of test compounds and CGRP-receptor agonist and, if needed, withdrawal of blood samples (max 2.5 ml, 10%) for blood gas monitoring and content analysis. At the end of the study, a solution of 5% dextrose is administered i.v. in order to maintain blood sugar levels. Anesthesia depth is monitored by measuring blood pressure and heart rate using a non-invasive arm cuff method and a pulse oximeter, respectively.

Guanethidine 5-10 mg/kg i.v., supplemented with 5 mg/kg i.v. as needed, may be given to stabilize the peak flux in facial blood flow seen with repeated stimulation-induced changes in blood flow (Escott et al., 1999). Microvascular blood flow is monitored by attaching a self adhesive laser Doppler flow probe to the facial skin.

Compound Administration. Test compounds may be administered i.v. (0.01-5 ml/kg), i.m. (0.01-0.5 ml/kg), s.c. (0.01-5 ml/kg) or p.o. (0.1-10 ml/kg) (Diehl et al., 2001). CGRP-receptor agonists may be delivered i.v. (0.01-5 ml/kg), i.d. (10-100 µl/site) or s.c. (10-100 µl/site).

Laser Doppler Flowmetry. A control increase in facial blood flow is induced by administration of a vasodilator, such as CGRP (0.05-100 µg/kg i.v.) or 2-20 pmol/site i.d). Test compound or vehicle is administered either before (pre-treatment) or after (post-treatment) subsequent repeat administration of the vasodilating agent, providing the ability to assess prophylactic or therapeutic actions. Blood pressure is monitored continuously to ensure adequate depth of anesthesia, and anesthetic is adjusted to maintain stable levels that match pre-treatment values. During collection of laser Doppler flowmetry data, isoflurane may be reduced to 0.25-0.75% as previous electrophysiological studies in marmosets found that recordings were sensitive to isoflurane concentration (Solomon, 1999). To reduce the number of animals used, the effect of test compound on i.v. vasodilator-induced changes in blood flow may be repeated up to 6 times in a single session.

Recovery. Animals are returned to the transport cage which is placed on a temperature controlled surface to keep the animals warm until fully awake and ambulatory. Animals may be tested again after 7-14 days rest, and may be tested repeatedly at 7-14 day intervals depending on the health of the animal See Diehl K H, Hull R, Morton D, Pfister R, Rabemampianina Y, Smith D, Vidal J M, van de Vorstenbosch C. A good practice guide to the administration of substances and removal of blood, including routes and volumes. J Appl Toxicol. 2001 January-February; 21(1):15-23; Doods H, Hallermayer G, Wu D, Entzeroth M, Rudolf K, Engel W, Eberlein W. Pharmacological profile of BIBN4096BS, the first selective small molecule CGRP-receptor antagonist. Br J Pharmacol. 2000 February; 129(3):420-3; Edvinsson L. Calcitonin gene-related peptide (CGRP) and the pathophysiology of headache: therapeutic implications. CNS Drugs 2001; 15(10):745-53; Escott K J, Beattie D T, Connor H E, Brain S D. Trigeminal ganglion stimulation increases facial skin blood flow in the rat: a major role for calcitonin gene-related peptide. Brain Res. 1995 Jan. 9; 669(1):93-9; Goadsby P J, Edvinsson L. The trigeminovascular system and migraine: studies characterizing cerebrovascular and neuropeptide changes seen in humans and cats. Ann Neurol. 1993 January; 33(1):48-56; Lassen L H, Haderslev P A, Jacobsen V B, Iversen H K, Sperling B, Olsen J. CGRP may play a causative role in migraine. Cephalalgia, 2002, 22, 54-61; Mallee J J, Salvatore C A, LeBourdelles B, Oliver K R, Longmore J, Koblan K S, Kane S A. RAMP1 determines the species selectivity of non-peptide CGRP receptor antagonists. J Biol Chem. 2002 Feb. 14 [epub ahead of print]; Solomon S G, White A J, Martin P R. Temporal contrast sensitivity in the lateral geniculate nucleus of a New World monkey, the marmoset *Callithrix jacchus*, J Physiol. 1999 Jun. 15; 517 (Pt 3):907-17.

TABLE 2

Inhibition of CGRP-Induced Increase in Laser Doppler Facial Blood Flow in the Non-Human Primate (e.g., Common Marmoset) % Inhibition in Non-Human Primate following single delivery of compound (at −30 to 0 min) against repeat hαCGRP (10 µg/kg, i.v.) delivery 1x at each time point (15-105 min)

| Example | Experimental Details | | | % Inhibition | | |
|---|---|---|---|---|---|---|
| | Pretreat | Route | Dose (mg/kg) | 15 min | 60 min | 105 min |
| 20 | −30 min | s.c. | 0.1 | 9.9 | −6.7 | −4.9 |
| 20 | −30 min | s.c. | 0.3 | 28.8 | 27.6* | 41.2* |
| 20 | −30 min | s.c. | 3 | 26.5 | 36.7* | 39.0* |
| 20 | −30 min | s.c. | 7 | 25.1 | 53.9* | 70.0* |
| haCGRP(8-37) | 0 min | i.v. | 1 | 87.2* | | |

*$P < 0.05$ Dunnett's vs baseline response to hαCGRP on laser Doppler facial blood flow Pharmaceutical Compositions and Methods of Treatment The compounds of Formula I inhibit the CGRP receptor. As such, they are useful for treating conditions or disorders associated with aberrant CGRP levels or where modulating CGRP levels may have therapeutic benefit.

Accordingly, another aspect of the invention is a pharmaceutical composition comprising a compound of Formula I with a pharmaceutically acceptable adjuvant, carrier, or diluent.

Compounds are generally given as pharmaceutical compositions comprised of a therapeutically effective amount of a compound of Formula I, or a pharmaceutically acceptable salt, and a pharmaceutically acceptable carrier and may contain conventional excipients. A therapeutically effective amount is the amount needed to provide a meaningful patient benefit as determined by practitioners in that art. Pharmaceutically acceptable carriers are those conventionally known carriers having acceptable safety profiles. Compositions encompass all common solid and liquid forms including capsules, tablets, losenges, and powders as well as liquid suspensions, syrups, elixers, and solutions. Solid compositions may by formed in timed or sustained released formulations. Compositions are made using common formulation techniques and conventional excipients (such as binding and wetting agents) and vehicles (such as water and alcohols).

Solid compositions are normally formulated in dosage units providing from about 1 to about 1000 mg of the active ingredient per dose. Some examples of solid dosage units are 0.1 mg, 1 mg, 10 mg, 100 mg, 500 mg, and 1000 mg. Liquid compositions are generally in a unit dosage range of 1-100 mg/mL. Some examples of liquid dosage units are 0.1 mg/mL, 1 mg/mL, 10 mg/mL, 25 mg/mL, 50 mg/mL, and 100 mg/mL.

The invention encompasses all conventional modes of administration including oral, parenteral, intranasal, sublingual, and transdermal methods. Typically, the daily dose will be 0.01-100 mg/kg body weight daily. Generally, more compound is required orally and less parenterally. The specific dosing regime, however, should be determined by a physician using sound medical judgement.

Inhibitors at the receptor level to CGRP are postulated to be useful in pathophysiologic conditions where excessive CGRP receptor activation has occurred. Some of these include neurogenic vasodilation, neurogenic inflammation, migraine, cluster headache and other headaches, thermal injury, circulatory shock, menopausal flushing, and asthma. CGRP receptor activation has been implicated in the pathogenesis of migraine headache (Edvinsson L. CNS Drugs 2001, 15(10), 745-53; Williamson, D. J. Microsc. Res. Tech. 2001, 53, 167-178; Grant, A. D. Brit. J. Pharmacol. 2002, 135, 356-362). Serum levels of CGRP are elevated during migraine (Goadsby P. J. et al. Ann. Neurol. 1990, 28, 183-7) and treatment with anti-migraine drugs returns CGRP levels to normal coincident with alleviation of headache (Gallai V. et al. Cephalalgia 1995, 15, 384-90). Migraineurs exhibit elevated basal CGRP levels compared to controls (Ashina M. et al., Pain 2000, 86(1-2), 133-8). Intravenous CGRP infusion produces lasting headache in migraineurs (Lassen L. H. et al. Cephalalgia. 2002, 22(1), 54-61). Preclinical studies in dog and rat report that systemic CGRP blockade with the peptide antagonist CGRP(8-37) does not alter resting systemic hemodynamics nor regional blood flow (Shen, Y-T. et al. J. Pharmacol. Exp. Ther. 2001, 298, 551-8). Thus, CGRP-receptor antagonists may present a novel treatment for migraine that avoids the cardiovascular liabilities of active vasoconstriction associated with non-selective 5-HT1B/1D agonists, "triptans" (e.g., sumatriptan).

Another aspect of the invention is a method of inhibiting the CGRP receptor comprising contacting the CGRP receptor with a compound of formula I or a pharmaceutically acceptable salt thereof.

Another aspect of the invention is a method for treating conditions associated with aberrant levels of CGRP comprising the administration of a therapeutically effective amount of a compound of formula I to a patient.

Another aspect of the invention is the use of a compound of formula I in the manufacture of a medicament for the treatment of conditions related to aberrant levels of CGRP.

Another aspect of the invention is a method of treating migraine or headache.

Another aspect of the invention relates to a method of treating inflammation (particularly neurogenic inflammation), pain, thermal injury, circulatory shock, diabetes, Reynaud's syndrome, peripheral arterial insufficiency, subarachnoid/cranial hemorrhage, tumor growth, flushing associated with menopause and other conditions the treatment of which can be effected by the antagonism of the CGRP receptor by the administration of pharmaceutical compositions comprising compounds of Formula (I) as defined herein.

Another aspect of the invention relates to methods selected from the group consisting of (a) immune regulation in gut mucosa (b) protective effect against cardiac anaphylactic injury (c) stimulating or preventing interleukin-1b(IL-1b)-stimulation of bone resorption (d) modulating expression of NK1 receptors in spinal neurons and (e) airway inflammatory diseases and chronic obstructive pulmonary disease including asthma. See (a) Calcitonin Receptor-Like Receptor Is Expressed on Gastrointestinal Immune Cells. Hagner, Stefanie; Knauer, Jens; Haberberger, Rainer; Goeke, Burkhard; Voigt, Karlheinz; McGregor, Gerard Patrick. Institute of Physiology, Philipps University, Marburg, Germany. Digestion (2002), 66(4), 197-203; (b) Protective effects of calcitonin gene-related peptide-mediated evodiamine on guinea-pig cardiac anaphylaxis. Rang, Wei-Qing; Du, Yan-Hua; Hu, Chang-Ping; Ye, Feng; Tan, Gui-Shan; Deng, Han-Wu; Li, Yuan-Jian. School of Pharmaceutical Sciences, Department of Pharmacology, Central South University, Xiang-Ya Road 88, Changsha, Hunan, Naunyn-Schmiedeberg's Archives of Pharmacology (2003), 367(3), 306-311; (c) The experimental study on the effect calcitonin gene-related peptide on bone resorption mediated by interleukin-1. Lian, Kai; Du, Jingyuan; Rao, Zhenyu; Luo, Huaican. Department of Orthopedics, Xiehe Hospital, Tongji Medical College, Huazhong University of Science and Technology, Wuhan, Peop. Rep. China. Journal of Tongji Medical University (2001), 21(4), 304-307, (d) Calcitonin gene-related Peptide regulates expression of neurokinin) receptors by rat spinal neurons. Seybold V S, McCarson K E, Mermelstein P G, Groth R D, Abrahams L G. J. Neurosci. 2003 23 (5): 1816-1824. Department of Neuroscience, University of Minnesota, Minneapolis, Minn. 55455, and Department of Pharmacology, Toxicology, and Therapeutics, University of Kansas Medical Center, Kansas City, Kans. 66160 (e) Attenuation of antigen-induced airway hyperresponsiveness in CGRP-deficient mice. Aoki-Nagase, Tomoko; Nagase, Takahide; Oh-Hashi, Yoshio; Shindo, Takayuki; Kurihara, Yukiko; Yamaguchi, Yasuhiro; Yamamoto, Hiroshi; Tomita, Tetsuji; Ohga, Eijiro; Nagai, Ryozo; Kurihara, Hiroki; Ouchi, Yasuyoshi. Department of Geriatric Medicine, Graduate School of Medicine, University of Tokyo, Tokyo, Japan. American Journal of Physiology (2002), 283(5, Pt. 1), L963-L970; (f) Calcitonin gene-related peptide as inflammatory mediator. Springer, Jochen; Geppetti, Pierangelo; Fischer, Axel; Groneberg, David A. Charite Campus-Virchow, Department of Pediatric Pneumology and Immunology, Division of Allergy Research, Humboldt-University Berlin, Berlin, Germany. Pulmonary Pharmacology & Therapeutics (2003), 16(3), 121-130; and (g) Pharmacological targets for the inhibition of neurogenic inflammation. Helyes, Zsuzsanna; Pinter, Erika; Nemeth, Jozsef; Szolcsanyi, Janos. Department of Pharmacology and Pharmacotherapy, Faculty of Medicine, University of Pecs, Pecs, Hung. Current Medicinal Chemistry: Anti-Inflammatory & Anti-Allergy Agents (2003), 2(2), 191-218.

Another aspect of this invention relates to a method of treatment using combinations of Formula I compounds with one or more agents selected from the group consisting of COX-2 inhibitors, NSAIDS, aspirin, acetaminophen, triptans, ergotamine and caffeine for the treatment of migraine.

"Migraine," "headache," and related terms are as understood by medical practitioners. Migraine encompasses all classes of migraine including common, classic, cluster, fulgurating, hemiplegic, opthalmoplegic, and opthomalmic.

"Therapeutically effective" means there is a meaningful patient benefit as understood by medical practitioners.

"Patient" means a person who may benefit from treatment as determined by medical practitioners.

DESCRIPTION OF SPECIFIC EMBODIMENTS

Abbreviations generally follow conventions used in the art. Chemical abbreviations used in the specification and Examples are defined as follows: "NaHMDS" for sodium bis(trimethylsilyl)amide; "DMF" for N,N-dimethylformamide; "MeOH" for methanol; "NBS" for N-bromosuccinimide; "Ar" for aryl; "TFA" for trifluoroacetic acid; "LAH" for lithium aluminum hydride; "BOC", "DMSO" for dimethylsulfoxide; "h" for hours; "rt" for room temperature or retention time (context will dictate); "min" for minutes; "EtOAc" for ethyl acetate; "THF" for tetrahydrofuran; "EDTA" for ethylenediaminetetraacetic acid; "Et$_2$O" for diethyl ether; "DMAP" for 4-dimethylaminopyridine; "DCE" for 1,2-dichloroethane; "ACN" for acetonitrile; "DME" for 1,2-dimethoxyethane; "HOBt" for 1-hydroxybenzotriazole hydrate; "DIEA" for diisopropylethylamine, "Nf" for CF$_3$(CF$_2$)$_3$SO$_2$—; and "TMOF" for trimethylorthoformate.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" or "ml" for milliliter or milliliters, "μL" for microliter or microliters, "N" for normal, "M" for molar, "mmol" for millimole or millimoles, "min" for minute or minutes, "h" for hour or hours, "rt" for room temperature, "RT" for retention time, "atm" for atmosphere, "psi" for pounds per square inch, "conc." for concentrate, "sat" or "sat'd "for saturated, "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

Proton magnetic resonance (1H NMR) spectra were recorded on a Bruker AC 300 or AC 500. All spectra were determined in the solvents indicated and chemical shifts are reported in δ units downfield from the internal standard tetramethylsilane (TMS) and interproton coupling constants are reported in Hertz (Hz). Splitting patterns are designated as follows: s, singlet; d, doublet; t, triplet; q, quartet; m, multiplet; br, broad peak. Low resolution mass spectra (MS) and the apparent molecular (MH+) or (M–H)+ was determined on a Micromass platform. Elemental analysis are reported as percent by weight. The products were purified by Prep HPLC using the column YMC S5 ODS (30×100 mm) at a flow rate of 40.0 mL/min and gradient time of 8.0 min. starting from solvent composition of 40% MeOH-60% $H_2O$-0.1% TFA and ending with solvent composition 95% MeOH-5% $H_2O$-0.1% TFA. The products were analyzed by a HPLC instrument using an XTERA column (3.0×50 mm S7) starting from solvent A (10% MeOH—90% water—0.1% trifluoroacetic acid (TFA)) and reaching solvent B (10% water—90% methanol—0.1% TFA) over a gradient time of 2 min. The flow rate is 5 mL/min. and retention time (Rf) of product was measured at 220 nm wavelength.

Intermediate 1

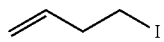

4-iodobut-1-ene. In an oven-dried 500 mL round-bottomed flask (t=g), a solution of triphenylphosphine (22.40 g, 85 mmol) and imidazole (5.82 g, 85 mmol) in $CH_2Cl_2$ (200 mL) was cooled to 0° C. to give a colorless solution. Iodine (21.68 g, 85 mmol) was carefully added. After 15 minutes, 3-Buten-1-ol (7.0 mL, 81 mmol) was added dropwise, and the mixture was allowed to warm up to room temperature overnight. The $CH_2Cl_2$ was removed under house vac but no heating was used (the product is extremely volatile!) to provide an orange slurry which was diluted with pentane and filtered through a pad of celite and a layer of silica gel. The solvent was then removed under house vac without warming A slightly yellow oil was obtained, crude 4-iodobut-1-ene (11.51 g, 78%), which was directly subject to the following reaction.

Intermediate 2

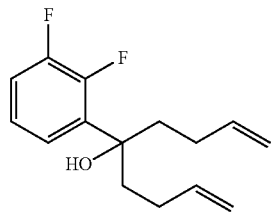

5-(2,3-difluorophenyl)nona-1,8-dien-5-ol. In a 500 mL round-bottomed flask (t=g) was added crude 4-iodobut-1-ene (11.51 g, 63.2 mmol) in $Et_2O$ (100 mL) to give a colorless solution. After cooling to −78° C. under nitrogen, tBuLi (80 mL, 136 mmol) was added dropwise via syringe. The mixture was slowly warmed up to room temperature while stirring for 2 hours. After 20 minutes at room temperature, the mixture was cooled to −78° C. and ethyl 2,3-difluorobenzoate (4.28 mL, 28.7 mmol) was added dropwise via syringe. The mixture was gradually warmed up to room temperature over 30 minutes. The reaction was quenched by water and the volatiles were evaporated. The residue was partitioned between water and EtOAc. The layers were separated and the organic layer was washed with brine, dried with $Na_2SO_4$ and concentrated to a light yellow oil. Purification up to 40% $Et_2O$ in hexane afforded the desired product as a colorless oil: (1.41 g, 19%). $^1$H NMR (400 MHz, $CDCl_3$) δ 7.31-7.22 (m, 1H), 7.10-7.03 (m, 2H), 5.82-5.70 (m, 2H), 4.97-4.85 (m, 4H), 2.20-2.00 (m, 4H), 2.00-1.75 (m, 4H).

Intermediate 3

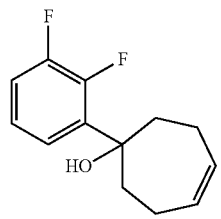

(Z)-1-(2,3-difluorophenyl)cyclohept-4-enol. In a 500 mL round-bottomed flask (t=g) was added 5-(2,3-difluorophenyl)nona-1,8-dien-5-ol (1.15 g, 4.56 mmol) in $CH_2Cl_2$ (50 mL) to give a colorless solution. Grubbs II (0.193 g, 0.228 mmol) was added, and the mixture was heated at 45° C. for 19 hours. TLC showed clean conversion to a more polar spot. Combined material with 68908-184 and concentrated to dryness and the residue was subject to purification up to 50% $Et_2O$/hexane. The major peak was pooled and concentrated to a colorless oil (0.761 g, 74.5%). $^1$H NMR showed the majority as the desired product (same as the later synthesized compound using Grubbs I catalyst) and a minor component with double-bond isomerized.

Intermediate 4

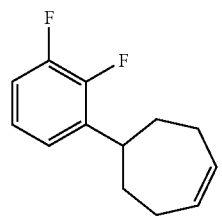

(Z)-5-(2,3-difluorophenyl)cyclohept-1-ene. In a 100 mL round-bottomed flask (t=g) was added (Z)-1-(2,3-difluorophenyl)cyclohept-4-enol (872 mg, 3.89 mmol) in $CH_2Cl_2$ (16 mL) to give a colorless solution. Triethylsilane (3.11 mL, 19.44 mmol) was added, following by TFA (8.00 mL). The mixture was stirred at room temperature for 2.5 hours. TLC showed clean conversion to a less polar compound. It was concentrated down and purification by FCC up to 20% $Et_2O$ in hexane afforded the desired product as a colorless oil (769 mg, 95%). The product was quickly eluted out. $^1H$ NMR (the major peaks are the same as these in the later synthesis) confirmed the structure.

Intermediate 5

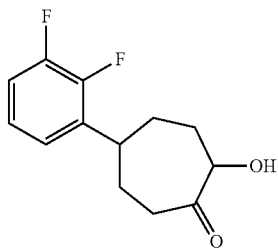

5-(2,3-difluorophenyl)-2-hydroxycycloheptanone. Ref. Plietker, B. J. Org. Chem. 2004, 69, 8287-8296. In a 500 mL round-bottomed flask (t=g) was added sodium bicarbonate (827 mg, 9.84 mmol) with a stirring bar. Ruthenium(III) chloride (8.17 mg, 0.039 mmol) was added (aqueous solution was used in the ref but it was difficult to completely dissolve). To the solids was added water (3.94 mL), EtOAc (20 ml), and MeCN (20 ml) to afford a brown suspension. Oxone (1.21E+04 mg, 19.69 mmol) was added in one portion, resulting in the formation of a bright yellow suspension. The mixture was cooled to −20° C. (Z)-5-(2,3-difluorophenyl)cyclohept-1-ene (820 mg, 3.94 mmol) was added (with 7.2 ml 1/1 EtOAc/MeCN wash). The color instantly turned to slightly tan. The reaction was stirred at −20 ~−15° C. for 1.5 hours. TLC showed no reaction. Warmed up to 0° C. for 10 minutes, but by TLC the reaction didn't improve much. It was warmed up to room temperature for 15-20 minutes. TLC showed disappearing of one major less polar spot (a minor one remained) and appearance of a more polar, slightly uv-active spot. The solids were filtered and washed with EtOAc. The organic solution was washed with aqueous $NaHSO_3$ solution. The organic layer was dried with $Na_2SO_4$ and concentrated to a colorless oil. It was purified by FCC up to 5% MeOH/$CH_2Cl_2$. The more polar peak/peaks were pooled and concentrated to a colorless oil (169 mg, 18%). It was directly carried onto the next protection reaction.

Example 1

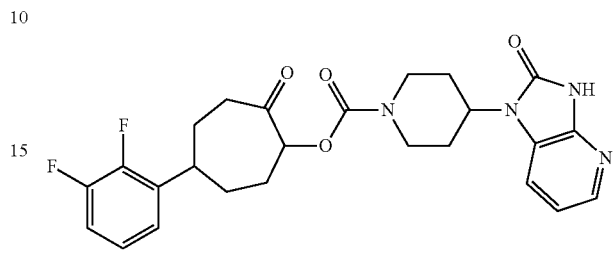

5-(2,3-difluorophenyl)-2-oxocycloheptyl 4-(2-oxo-2,3-dihydro-1H-imidazo[4,5-b]pyridin-1-yl)piperidine-1-carboxylate. In an oven-dried 50 mL round-bottomed flask (t=g) was added 5-(2,3-difluorophenyl)-2-hydroxycycloheptanone (22 mg, 0.092 mmol) and 4-Nitrophenyl chloroformate (20.30 mg, 0.101 mmol) in THF (3 mL) to give a colorless solution. DMAP (15.66 mg, 0.128 mmol) was added, and the mixture was stirred at room temperature for 3 hours. TLC showed a new less polar spot (more polar than the chloride) but mainly starting material. Allowed reaction to stir overnight for 24 hours. To the above reaction mixture was added 1-(piperidin-4-yl)-1H-imidazo[4,5-b]pyridin-2(3H)-one (53.6 mg, 0.184 mmol), followed by Hunig's Base (0.040 mL, 0.230 mmol). The resulted mixture was stirred at room temperature overnight. LCMS showed two close small peaks which has the MW of 484. 22 h: It was diluted with water and extracted with EtOAc. The organic layer was washed 3 times with water, brine, dried with $Na_2SO_4$ and concentrated to a tan oil. FCC up to 8% MeOH/$CH_2Cl_2$ afforded the desired product as mixture of two diasteromers: 11.7 mg (26%). LCMS: M+H=485.

Intermediate 6

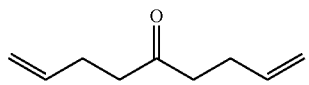

nona-1,8-dien-5-one. In an oven-dried 500 mL round-bottomed flask (t=g) was added 4-Pentenoyl chloride (6.04 mL, 54.7 mmol) in THF (80 mL) to give a tan solution. After cooling to −78° C., 3-Butenylmagnesium bromide (115 mL, 57.5 mmol) was added via syringe over 90 min. After warming to room temperature for 3 hours, the reaction was quenched with saturated $NH_4Cl$ solution. THF was stripped off and the remaining was extracted with EtOAc. The organic layer was washed with brine, dried with $Na_2SO_4$, and concentrated to a slightly yellow oil. Purification (two batches) by FCC up to 40% $Et_2O$/hexane afforded the product as a colorless oil: (5.13 g, 68%). $^1$H NMR (400 MHz, CDCl$_3$) δ 5.84-5.68 (m, 2H), 5.05-4.90 (m, 4H), 2.49 (t, J=7.4 Hz, 4H), 2.35-2.20 (m, 4H).

Intermediate 7

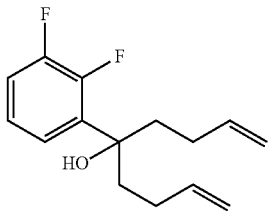

5-(2,3-difluorophenyl)nona-1,8-dien-5-ol. In an oven-dried 250 mL round-bottomed flask (t=g) was added 1-Bromo-2,3-difluorobenzene (2.304 mL, 20.58 mmol) in THF (60 mL) to give a colorless solution. After cooling to −78° C., BuLi (8.23 mL, 20.58 mmol) was added dropwise via syringe. The mixture was stirred at −78° C. for 20 minutes, and nona-1,8-dien-5-one (2.37 g, 17.15 mmol) (azeotroped with dry benzene) was added dropwise via canuula (plus 6 ml THF rinse). The mixture was warmed up to room temperature over 1 hour. Quenched with water and the THF solvent was stripped off. The remaining mixture was extracted with EtOAc. The layers were separated and the organic layer was washed with brine, dried with Na$_2$SO$_4$, and concentrated to a yellow oil. The residue was purified by FCC up to 35% Et$_2$O/hexane. The desired fractions were pooled and concentrated to the product as a colorless oil (2.39 g, 55.3%). $^1$H NMR (400 MHz, CDCl$_3$) δ 7.30-7.22 (m, 1H), 7.10-7.03 (m, 2H), 5.82-5.70 (m, 2H), 4.97-4.85 (m, 4H), 2.20-2.00 (m, 4H), 2.00-1.75 (m, 4H).

Intermediate 8

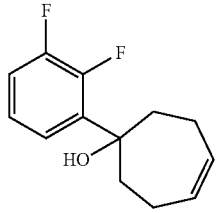

(Z)-1-(2,3-difluorophenyl)cyclohept-4-enol. In a 1 L round-bottomed flask (t=g) was added 5-(2,3-difluorophenyl)nona-1,8-dien-5-ol (1.76 g, 6.98 mmol) in CH$_2$Cl$_2$ (600 mL) to give a colorless solution. Grubbs I (0.175 g, 0.209 mmol) was added, and the mixture was heated at 40° C. for 2 hours. TLC showed clean conversion to a more polar spot (some impurities from starting material remained). Combined with 68908-198 and concentrated to dryness and the residue was subject to purification up to 50% Et$_2$O/hexane (twice). The major peak was pooled and concentrated to a light green oil (1.40 g, 89.2%). $^1$H NMR (400 MHz, CDCl$_3$) δ 7.34-7.25 (m, 1H), 7.08-7.00 (m, 2H), 5.90-5.80 (m, 2H), 2.60-2.48 (m, 2H), 2.21 (t, J=7.0 Hz, 2H), 2.10-1.98 (m, 2H), 1.90-1.75 (m, 2H).

Intermediate 9

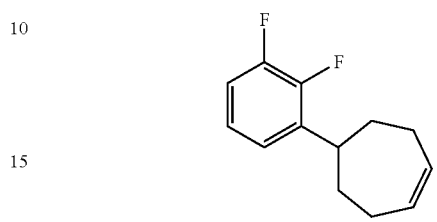

(Z)-5-(2,3-difluorophenyl)cyclohept-1-ene. In a 250 mL round-bottomed flask (t=g) was added (Z)-1-(2,3-difluorophenyl)cyclohept-4-enol (2.05 g, 9.14 mmol) in CH$_2$Cl$_2$ (40 mL) to give a colorless solution. Triethylsilane (7.30 mL, 45.7 mmol) was added, followed by TFA (20 mL). The mixture was stirred at room temperature for 3 hours: TLC showed a complete conversion (Rf=0.42 by pure hexane). It was concentrated down to a bi-layer oil (the lower layer wasn't hexane-soluble). Purification by FCC using only hexane afforded the desired product as a colorless oil (1.684 g, 88%). $^1$H NMR (400 MHz, CDCl$_3$) δ 7.00-6.90 (m, 3H), 5.90-5.82 (m, 2H), 3.20-3.05 (m, 1H), 2.40-2.15 (m, 4H), 1.90-1.78 (m, 2H), 1.60-1.40 (m, 2H).

Intermediate 10

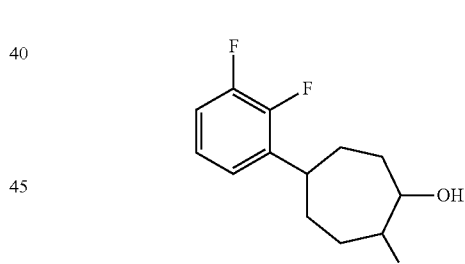

5-(2,3-difluorophenyl)cycloheptane-1,2-diol. See: D. A. Spiegel et al. Tetrahedron 2002, 58, 6545-6554. In a 250 mL round-bottomed flask (t=g) was added (Z)-5-(2,3-difluorophenyl)cyclohept-1-ene (1.249 g, 6.00 mmol) and NMO (1.546 g, 13.19 mmol) in Acetone (9 mL) and Water (0.18 mL) to give a white suspension. Osmium tetroxide (0.301 mL, 0.024 mmol) (2.5 wt % solution in 2-methyl-2-propanol) was added. The mixture was stirred at room temperature. NMO gradually dissolved within 30 minutes to become a yellow solution. 1 h: TLC showed complete conversion to a much polar spot. Sodium bisulfite (200 mg) was added and stirring continued for 30 minutes. Acetone was stripped off and the residue was extracted with EtOAc three times. The combined organic layers were washed with brine, dried and concentrated to a white solid (crude weight: 1.7 g). It was directly carried onto next reaction.

Intermediate 11

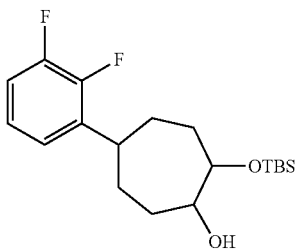

2-(tert-butyldimethylsilyloxy)-5-(2,3-difluorophenyl)cycloheptanol. In a 250 mL round-bottomed flask (t=g) was added 5-(2,3-difluorophenyl)cycloheptane-1,2-diol (1.454 g, 6.0 mmol) (crude material, azeotroped with dry benzene) in DMF (20 mL) to give a colorless solution. TBS-Cl (0.995 g, 6.60 mmol) and imidazole (0.980 g, 14.40 mmol) were added, and the mixture was stirred at room temperature for 5 hours. TLC (2/1 hexane/EtOAc) indicated complete conversion to two main spots. It was diluted with water and extracted with EtOAc twice. The combined organic layers were washed with brine, dried with $Na_2SO_4$ and concentrated to a colorless oil. Purification by FCC up to 30% EtOAc/hexane afforded the desired mono-protected product as a broad peak. The product fractions were pooled and concentrated to a colorless oil (1.79 g, 84% for two steps). $^1$H NMR (400 MHz, $CDCl_3$) δ 7.02-6.85 (m, 3H), 3.98-3.70 (m, 2H), 3.18-3.02 (m, 1H), 2.15-1.82 (m, 4H), 1.80-1.45 (m, 4H), 0.91 (s, 9H), 0.90 (2 s, 6H).

Intermediate 12 Intermediate 13

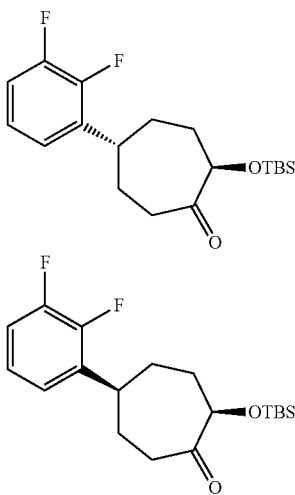

(2R,5R)-2-(tert-butyldimethylsilyloxy)-5-(2,3-difluorophenyl)cycloheptanone. In a 250 mL round-bottomed flask (t=g) was added 2-(tert-butyldimethylsilyloxy)-5-(2,3-difluorophenyl)cycloheptanol (1.73 g, 4.85 mmol) in $CH_2Cl_2$ (50 mL) to give a colorless solution. Dess-Martin Periodinane (2.264 g, 5.34 mmol) was added in one portion, and the mixture was stirred at room temperature overnight. 17 h: TLC showed complete conversion. It was diluted with $Et_2O$ and treated with 40 ml saturated $Na_2S_2O_3$ and $Na_2HCO_3$ solution (1/1 mixture) until the milky solution became clear (10 min). The layers were separated and the aqueous layer was extracted with $Et_2O$. The combined organic layers were washed with brine, dried with $Na_2SO_4$, and concentrated to a colorless oil (with some solids insoluble in hexane). Purification by FCC up to 40% $Et_2O$ in hexane afforded two peaks. They were individually pooled and concentrated. The less polar major one (978 mg, 55%) was a colorless oil. $^1$H NMR (500 MHz, $CDCl_3$) δ 7.02-6.90 (m, 3H), 4.34 (d, J=4.6 Hz, 1H), 2.82-2.75 (m, 2H), 2.54-2.46 (m, 1H), 2.45-2.32 (m, 1H), 2.17-1.98 (m, 2H), 1.90-1.68 (m, 3H), 0.94 (s, 9H), 0.08 (s, 6H); $^{13}$C NMR (125 MHz, $CDCl_3$) δ 213.4, 150.7 (dd, J=247.6 and 13.4 Hz), 147.8 (dd, J=245.7 and 13.4 Hz), 137.5 (d, J=11.5 Hz), 127.7, 122.2, 114.7 (d, J=17.3 Hz), 79.0, 40.0, 39.2, 33.2, 30.7, 29.4, 25.8, 18.2, −5.0. The more polar minor one solidified upon standing to a white solid (698 mg, 39%). It was re-crystallized from hexane and X-ray analysis verified the anti-stereochemistry relation. $^1$H NMR (500 MHz, $CDCl_3$) δ 7.10-6.97 (m, 2H), 6.97-6.90 (m, 1H), 4.34 (dd, J=3.0 and 9.7 Hz, 1H), 3.04-2.94 (m, 1H), 2.80-2.70 (m, 1H), 2.62-2.50 (m, 1H), 2.18-1.72 (m, 6H), 0.90 (s, 9H), 0.10 (s, 3H), 0.06 (s, 3H); $^{13}$C NMR (125 MHz, $CDCl_3$) δ 211.0, 150.8 (dd, J=248.6 and 13.5 Hz), 148.1 (dd, J=246.7 and 12.5 Hz), 136.4 (d, J=11.5 Hz), 124.2, 122.3, 115.1 (d, J=17.3 Hz), 78.4, 40.3, 39.4, 34.3, 33.0, 30.4, 25.9, 18.5, −4.5, −5.1.

Intermediate 14

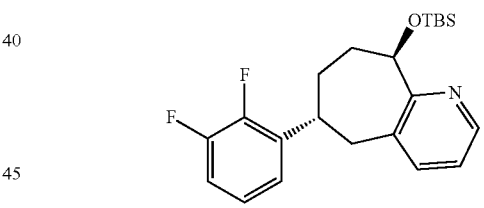

(6,9-anti)-9-(tert-butyldimethylsilyloxy)-6-(2,3-difluorophenyl)-6,7,8,9-tetrahydro-5H-cyclohepta[b]pyridine. In a 25 mL flask (t=g) was added (2S,5S)-2-(tert-butyldimethylsilyloxy)-5-(2,3-difluorophenyl)cycloheptanone (279 mg, 0.787 mmol) in Ethanol (4 mL) to give a colorless solution. Sodium tetrachloroaurate(III) dihydrate (9.39 mg, 0.024 mmol) and Propargylamine (0.101 mL, 1.574 mmol) were added. The reaction was heated at 80° C. for 5 hours. After the tan mixture was cooled to room temperature, it was diluted with EtOAc, filtered through a plug of cotton, and concentrated to a tan oil. FCC up to 20% EtOAc/hexane afforded the desired product as a major peak (60.3 mg, 20%) as well as a little recovered starting material. $^1$H NMR (400 MHz, $CDCl_3$) δ 8.45-8.40 (m, 1H), 7.32-7.29 (m, 1H), 7.08-7.04 (m, 1H), 7.04-6.92 (m, 2H), 6.92-6.80 (m, 1H), 5.13-5.07 (m, 1H), 3.30-3.00 (m, 3H), 2.32-2.10 (m, 2H), 2.10-1.90 (m, 2H), 0.91 (s, 9H), 0.074 (s, 3H), 0.042 (s, 3H).

Intermediate 15

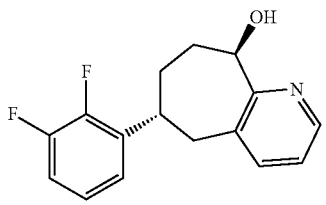

(6,9-anti)-6-(2,3-difluorophenyl)-6,7,8,9-tetrahydro-5H-cyclohepta[b]pyridin-9-ol. In a 50 mL round-bottomed flask (t=g) was added (6R,9R)-9-(tert-butyldimethylsilyloxy)-6-(2,3-difluorophenyl)-6,7,8,9-tetrahydro-5H-cyclohepta[b]pyridine (60.3 mg, 0.155 mmol) in THF (3 mL) to give a colorless solution. TBAF (0.310 mL, 0.310 mmol) was added, and the mixture was stirred at room temperature overnight. 19 h: LCMS and TLC showed complete conversion. THF was stripped off and the residue was diluted with EtOAc, washed with water, brine, dried with $Na_2SO_4$, and concentrated to a tan oil. FCC up to 30% EtOAc/hexane afforded one peak, which was pooled and concentrated to a white solid (35.7 mg, 84%). LCMS: [M+H]=276; $^1$H NMR (400 MHz, $CDCl_3$) δ 8.42-8.40 (m, 1H), 7.47 (d, J=7.6 Hz, 1H), 7.16 (dd, J=7.2 and 5.0 Hz, 1H), 7.15-7.00 (m, 3H), 5.97 (br., 1H), 4.88 (dd, J=11.6 and 1.6 Hz, 1H), 3.19 (t, J=12.8 Hz, 1H), 2.99-2.83 (m, 1H), 2.80 (d, J=14.4 Hz, 1H), 2.38-2.23 (m, 1H), 2.23-2.05 (m, 2H), 1.69-1.50 (m, 1H); $^{13}$C NMR (125 MHz, $CDCl_3$) δ 160.7, 150.8 (d, J=247.4 Hz), 148.1 (d, J=261.2 Hz), 145.1, 137.8, 136.5 (d, J=12.3 Hz), 133.6, 124.2, 122.4, 122.1, 115.1 (d, J=16.9 Hz), 71.8, 40.5, 37.6, 36.2, 35.8.

Example 2

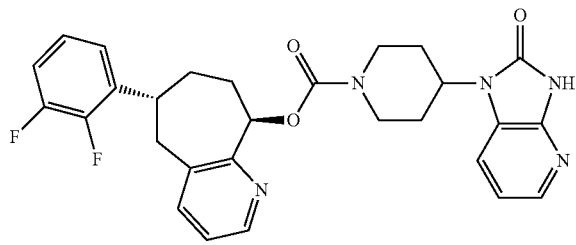

(6,9-anti)-6-(2,3-difluorophenyl)-6,7,8,9-tetrahydro-5H-cyclohepta[b]pyridin-9-yl 4-(2-oxo-2,3-dihydro-1H-imidazo[4,5-b]pyridin-1-yl)piperidine-1-carboxylate. In a 100 mL round-bottomed flask (t=g) was added (6R,9R)-6-(2,3-difluorophenyl)-6,7,8,9-tetrahydro-5H-cyclohepta[b]pyridin-9-ol (22.2 mg, 0.081 mmol) (azeotroped with dry benzene) and 4-nitrophenyl 4-(2-oxo-2,3-dihydro-1H-imidazo[4,5-b]pyridin-1-yl)piperidine-1-carboxylate (93 mg, 0.242 mmol) in THF (3 mL) to give a tan suspension. NaH (19.35 mg, 0.806 mmol) (excess) was added in one portion. The mixture was stirred under nitrogen at room temperature overnight. 18 h: LCMS showed complete conversion. It was quenched with water (gas evolves!) and extracted with EtOAc. The layers were separated and the aqueous layer was extracted with EtOAc (LCMS showed no product in the aqueous). The combined organic layers were washed with brine, dried with $Na_2SO_4$, and concentrated. Purification by FCC up to 8% $MeOH/CH_2Cl_2$ afforded the product as a white solid (28.6 mg, 68%). LCMS: [M+H]=520; $^1$H NMR (400 MHz, $CDCl_3$) δ 10.5 (br., 1H), 8.47 (d, J=3.6 Hz, 1H), 8.07 (d, J=4.4 Hz, 1H), 7.44 (br., 2H), 7.15 (br., 1H), 7.09-6.95 (m, 4H), 6.03 (d, J=10.8 Hz, 1H), 4.77-4.52 (br., 2H), 4.52-4.30 (br., 1H), 3.36 (t, J=12.6 Hz, 1H), 3.20-2.90 (m, 3H), 2.83 (d, J=14.4 Hz, 1H), 2.42-2.12 (m, 4H), 2.02-1.78 (m, 4H); mp 248° C.

Example 3

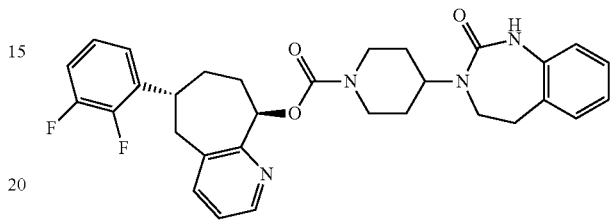

(6,9-anti)-6-(2,3-difluorophenyl)-6,7,8,9-tetrahydro-5H-cyclohepta[b]pyridin-9-yl 4-(2-oxo-4,5-dihydro-1H-benzo[d][1,3]diazepin-3(2H)-yl)piperidine-1-carboxylate. In a 100 mL round-bottomed flask (t=g) was added (6R,9R)-6-(2,3-difluorophenyl)-6,7,8,9-tetrahydro-5H-cyclohepta[b]pyridin-9-ol (13.5 mg, 0.049 mmol) (azeotroped with dry benzene) and 4-nitrophenyl 4-(2-oxo-4,5-dihydro-1H-benzo[d][1,3]diazepin-3(2H)-yl)piperidine-1-carboxylate (60.4 mg, 0.147 mmol) in THF (2 mL) to give a tan suspension. NaH (11.77 mg, 0.490 mmol) (excess) was added in one portion. The mixture was stirred under nitrogen at room temperature overnight. 18 h: LCMS showed complete conversion. It was quenched with water (gas evolves!) and extracted with EtOAc. The layers were separated and the aqueous layer was extracted with EtOAc. The combined organic layers were washed with brine, dried with $Na_2SO_4$, and concentrated. Purification by FCC up to 8% $MeOH/CH_2Cl_2$ afforded the product as a white powder. LCMS showed a minor peak (M+Br) but $^1$H NMR looks fine. Treatment with $NaHSO_3$ in MeOH/Water for 2 days didn't improve. The material was recovered without change (19.5 mg, 73%). LCMS: [M+H]= 547; $^1$H NMR (400 MHz, $CDCl_3$) δ 8.41 (d, J=Hz, 1H), 7.39 (d, J=Hz, 1H), 7.12-6.95 (m, 5H), 6.88 (t, J=Hz, 1H), 6.72 (d, J=Hz, 1H), 6.65 (s, 1H), 5.98 (d, J=Hz, 1H), 4.60-4.18 (br., 3H), 3.51 (br., 2H), 3.33 (t, J=Hz, 1H), 3.15-2.89 (m, 6H), 2.82 (d, J=Hz, 1H), 2.32-2.10 (m, 3H), 2.05-1.89 (m, 1H), 1.89-1.55 (m, 4H).

Intermediate 16

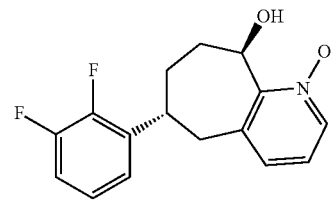

(6,9-trans)-6-(2,3-difluorophenyl)-9-hydroxy-6,7,8,9-tetrahydro-5H-cyclohepta[b]pyridine 1-oxide. In a 250 mL round-bottomed flask was (6,9-trans)-6-(2,3-difluorophenyl)-6,7,8,9-tetrahydro-5H-cyclohepta[b]pyridin-9-ol (191 mg, 0.694 mmol) in $CH_2Cl_2$ (4 mL) to give a colorless solution. mCPBA (202 mg, 0.902 mmol) was added, and the mixture was stirred at rt for 24 h. LCMS indicated a complete conversion to a major product peak. It was diluted with EtOAc and treated with 0.5 N NaOH. The layers were separated and the organic layer was washed with water, brine, dried with Na2SO4, and concentrated to a waxy solid/oil (crude: 100%). LCMS: [M+H]=292; ¹H NMR (400 MHz, CDCl₃) δ 8.06 (s, 1H), 7.24-6.40 (m, 5H), 5.27 (br, 1H), 3.42-3.02 (m, 2H), 3.02-2.68 (m, 2H), 2.30-1.95 (m, 3H), 1.80-1.60 (m, 1H).

Intermediate 17

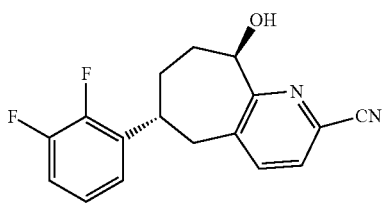

(6,9-trans)-6-(2,3-difluorophenyl)-9-hydroxy-6,7,8,9-tetrahydro-5H-cyclohepta[b]pyridine-2-carbonitrile. In a 100 mL round-bottomed flask was crude (6,9-trans)-6-(2,3-difluorophenyl)-9-hydroxy-6,7,8,9-tetrahydro-5H-cyclohepta[b]pyridine 1-oxide (0.202 g, 0.694 mmol) (azeotroped with dry benzene) in CH2Cl2 (4 mL) to give a colorless solution. Dimethylcarbamyl chloride (0.064 mL, 0.694 mmol) was added. After 2 h, Trimethylsilyl cyanide (0.111 mL, 0.833 mmol) was added and the mixture was stirred overnight under nitrogen for 16 h. Dimethylcarbamyl chloride (0.064 mL, 0.694 mmol) and trimethylsilyl cyanide (0.111 mL, 0.833 mmol) were again added. The mixture was heated at reflux (bath temp: 45° C.) for 22 h. LCMS showed multiple peaks and only tiny amount of sm left. It was quenched with saturated NaHCO3 solution and extracted with EtOAc. The layer was separated and the organic layer was washed with brine, dried and concentrated to a tan oil. It was dissolved in 4 ml THF and treated with TBAF (0.694 mL, 0.694 mmol) for 4 h. Aqueous work up with EtOAc afforded a tan residue. Purification by FCC up to 80% EtOAc/hexane afforded the product as a colorless solid (53 mg, 23%). LCMS: [M+H]=372; ¹H NMR (400 MHz, CDCl₃) δ 7.65-7.52 (m, 2H), 7.10-6.95 (m, 3H), 5.15 (d, J=4.0 Hz, 1H), 4.94 (d, J=11.6 Hz, 1H), 3.24 (t, J=12.8 Hz, 1H), 2.92-2.83 (m, 2H), 2.40-2.30 (m, 1H), 2.20-2.10 (m, 2H), 1.68-1.53 (m, 1H).

Example 4

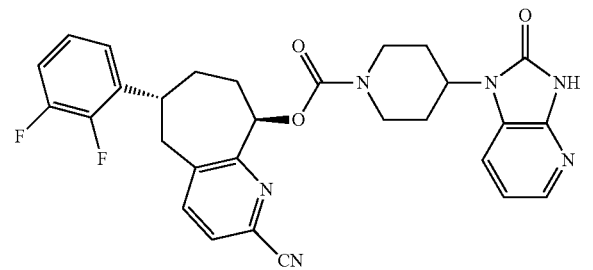

(6,9-trans)-2-cyano-6-(2,3-difluorophenyl)-6,7,8,9-tetrahydro-5H-cyclohepta[b]pyridin-9-yl 4-(2-oxo-2,3-dihydro-1H-imidazo[4,5-b]pyridin-1-yl)piperidine-1-carboxylate. In a 100 mL round-bottomed flask was (6,9-trans)-6-(2,3-difluorophenyl)-9-hydroxy-6,7,8,9-tetrahydro-5H-cyclohepta[b]pyridine-2-carbonitrile (52.6 mg, 0.175 mmol) (azeotroped with dry benzene) and 4-nitrophenyl 4-(2-oxo-2,3-dihydro-1H-imidazo[4,5-b]pyridin-1-yl)piperidine-1-carboxylate (201 mg, 0.525 mmol) in THF (2 mL) to give a tan suspension. NaH (42.0 mg, 1.752 mmol) (excess) was added in one portion. The mixture was stirred under nitrogen at r.t. overnight for 16 h. LCMS showed complete conversion. It was quenched with water (gas evolves!) and extracted with EtOAc. The layers were separated and the organic layer was washed with brine, dried with Na2SO4, and concentrated. Purification by FCC up to 10% MeOH/CH₂Cl₂ afforded the product as a white powder (76 mg, 72%). LCMS: [M+H]= 545; ¹H NMR (400 MHz, CDCl₃) δ 8.07 (br, 1H), 7.75-7.24 (m, 4H), 7.20-6.90 (m, 4H), 5.98 (d, J=11.2 Hz, 1H), 4.83-4.20 (m, 3H), 3.40 (t, J=12.8 Hz, 1H), 3.28-2.75 (m, 3H), 2.60-2.10 (m, 5H), 2.10-1.78 (m, 4H).

Intermediate 18

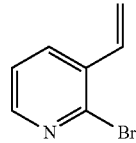

2-Bromo-3-vinylpyridine. See Spivey, A. C.; Shukla, L.; Hayler, J. F. Org. Lett. 2007, 9, 891-894. Butyllithium (22.75 mL, 59.1 mmol) was added to the THF (450 mL) suspension of methyltriphenylphosphonium bromide (21.13 g, 59.1 mmol) at 0° C. The solution turned to orange and the reaction was lift to room temperature for 30 min before cooled it back to 0° C. 2-bromonicotinaldehyde (10 g, 53.8 mmol) in 50 mL THF was added through canula to the reaction solution. The precipitate was formed and the reaction was lift to room temperature. The color of the reaction turned to green, gray. After a while, the color of to reaction became orange again. The reaction was stirred at room temperature over weekend. The solvent was removed mostly via vacuum and the crude was partitioned between water and diethyl ether. The organic layer was separated and the aqueous layer was extract twice with diethyl ether. The diethyl ether layer was combined, dried (Na2SO4), filtered and concentrated. The product was obtained by flash column eluted with ethyl acetate in hexane (10%) as yellow oil (8.78 g, 89%). MS (ESI)[M+H⁺]=184.04; 1H NMR δ ppm (400 MHz, CHLOROFORM-d) 8.21-8.29 (m, 1H) 7.78 (dd, J=7.68, 1.89 Hz, 1H) 7.20-7.28 (m, 1H) 6.96 (dd, J=17.37, 11.08 Hz, 1H) 5.72 (d, J=17.37 Hz, 1H) 5.46 (d, J=11.08 Hz, 1H).

Intermediate 19

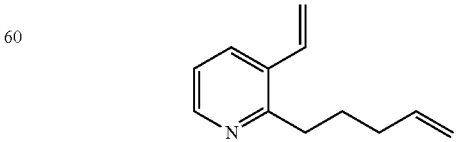

2-(Pent-4-enyl)-3-vinylpyridine. In a 500 mL round-bottomed flask was 2-bromo-3-vinylpyridine (4.151 g, 22.56 mmol) (azeotroped with dry benzene) in THF (40 mL) to give a colorless solution. Pd(Ph3P)4 (0.782 g, 0.677 mmol) was added under nitrogen. While stirring under nitrogen, 4-Pentenylzinc bromide (46 mL, 23.00 mmol) was added via syringe, and the resulted dark mixture was stirred at rt for 5 min. It was then heated at reflux (70° C.) overnight (4:00 pm). 17 h: LCMS indicated a complete conversion to the desired product. THF was stripped off. The reaction was quenched with NH4Cl solution and diluted with EtOAc. The layers were separated and the organic layer was washed with brine, dried and concentrated to a yellow oil. FCC up to 30% EtOAc/hexane afforded the desired product as a colorless oil (2.54 g, 65%). MS (ESI)[M+H$^+$]=174; 1H NMR (400 MHz, CHLOROFORM-d) δ ppm 8.39 (dd, J=4.78, 1.51 Hz, 1H) 7.69 (dd, J=7.81, 1.76 Hz, 1H) 7.07 (dd, J=7.81, 4.78 Hz, 1H) 6.89 (dd, J=17.37, 11.08 Hz, 1H) 5.80 (dddd, J=17.06, 10.26, 6.67, 6.55 Hz, 1H) 5.62 (d, J=17.37 Hz, 1H) 5.34 (d, J=11.08 Hz, 1H) 4.85-5.09 (m, 2H) 2.76-2.92 (m, 2H) 2.11 (q, J=7.13 Hz, 2H) 1.67-1.83 (m, 2H); 13C NMR (101 MHz, CHLOROFORM-d) δ ppm 159.17 (s, 1C) 148.31 (s, 1C) 138.38 (s, 1C) 133.22 (s, 1C), 133.19 (s, 1C), 131.73 (s, 1C) 121.40 (s, 1C) 117.22 (s, 1C) 114.87 (s, 1C) 34.99 (s, 1C) 33.64 (s, 1C) 28.60 (s, 1C).

Intermediate 20

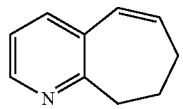

(Z)-8,9-Dihydro-7H-cyclohepta[b]pyridine. In a 2 L round-bottomed flask was 2-(pent-4-enyl)-3-vinylpyridine (2.1 g, 12.12 mmol) in ether (4 ml) to give a colorless solution. HCl (30 mL, 60.0 mmol) was added, and the mixture was stirred for 5 min. The volatiles were evaporated to give a colorless oil, which was then azeotroped with dry benzene to a white solid. It was then dissolved in CH$_2$Cl$_2$ (1 L) (degassed with argon) to give a colorless solution. GrubbsII (0.515 g, 0.606 mmol) was added, and the mixture was heated at a 40° C. oil bath with stirring under nitrogen for 5 h. LCMS indicated complete conversion (TLC showed a main spot less polar than the SM). The mixture was concentrated to a tan oil. It was dissolved EtOAc and washed with saturated NaHCO3 solution with a little 0.5N NaOH solution, brine, dried with Na2SO4, and concentrated to a tan oil. FCC up to 40% EtOAc/hexane afforded the desired product as a tan oil (1.79 g, 92%). MS (ESI)[M+H$^+$]=146.06; 1H NMR (400 MHz, CHLOROFORM-d) δ ppm 8.20 (d, J=4.78 Hz, 1H) 7.32 (d, J=7.55 Hz, 1H) 6.99 (dd, J=7.55, 5.04 Hz, 1H) 6.21 (dt, J=12.28, 2.05 Hz, 1H) 5.90 (dt, J=12.34, 4.41 Hz, 1H) 2.93-3.06 (m, 2H) 2.30-2.49 (m, 2H) 1.82-2.02 (m, 2H); 13C NMR (101 MHz, CHLOROFORM-d) δ ppm 160.56 (s, 1C) 146.26 (s, 1C) 137.79 (s, 1C) 134.18 (s, 1C) 131.32 (s, 1C) 127.24 (s, 1C) 121.16 (s, 1C) 39.10 (s, 1C) 32.54 (s, 1C) 24.87 (s, 1C).

Intermediate 21

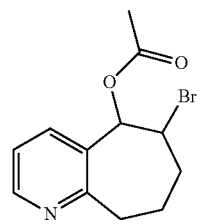

6-Bromo-6,7,8,9-tetrahydro-5H-cyclohepta[b]pyridin-5-yl acetate. In a 500 mL round-bottomed flask was (Z)-8,9-dihydro-7H-cyclohepta[b]pyridine (5.16 g, 35.5 mmol), LITHIUM ACETATE (9.38 g, 142 mmol) in Acetic Acid (100 mL) to give a tan suspension under nitrogen. N-Bromoacetamide (5.00 g, 36.2 mmol) was added. The flask was wrapped with aluminum foil and the mixture was stirred at rt overnight. 16 h: There was no solids left and LCMS showed complete conversion to the desired more polar product as a major peak. AcOH was stripped off under high vacuum. The residue was diluted with water and EtOAc. Na2CO3 was added to neutralize the mixture till no gas evolved. The layers were separated and the aqueous layer was extracted with EtOAc. The combined organic layers were washed with brine, dried with Na2SO4, and concentrated to a dense tan oil (10.5 g, 100%). The crude was used as it is. MS (ESI)[M+H$^+$]=284.17.

Intermediate 22

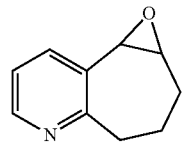

6-Bromo-6,7,8,9-tetrahydro-5H-cyclohepta[b]pyridin-5-yl acetate epoxide. In a 500 mL round-bottomed flask was 6-bromo-6,7,8,9-tetrahydro-5H-cyclohepta[b]pyridin-5-yl acetate (10.09 g, 35.5 mmol) (azeotroped with dry benzene) in THF (100 mL) to give a tan solution. SODIUM METHOXIDE (9.59 g, 178 mmol) was added, and the mixture was stirred at rt under nitrogen. 2 h: TLC showed complete conversion to the more polar product spot. 2.5 h: THF was stripped off and the residue was partitioned between water and EtOAc. The aqueous layer was extracted with EtOAc. The combined organic layers were washed with brine, dried with Na2SO4, and concentrated to a tan oil (5.71 g, 100%), which was directly used in the next reaction. MS (ESI)[M+H$^+$]=162.21.

Intermediate 23

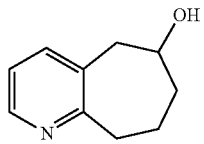

6,7,8,9-Tetrahydro-5H-cyclohepta[b]pyridin-6-ol. In a 500 mL round-bottomed flask was the epoxide (5.72 g, 35.5 mmol) and Pd/C (1.889 g, 1.775 mmol) in MeOH (100 mL) to give a black suspension. It was stirred under 1 atm hydrogen (balloon) for 2 h. LCMS indicated a little sm left. Another 0.95 g of Pd/C was added and the stirring continued for another 1 h. TLC showed no change (the trace might not be sm). It was filtered and concentrated to a tan oil (6 g, 100%). It was used in the next reactions without further purification and characterizations.

Intermediate 24

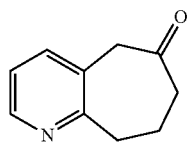

8,9-Dihydro-5H-cyclohepta[b]pyridin-6(7H)-one. In an oven-dried 500 mL round-bottomed flask was OXALYL CHLORIDE (3.42 mL, 39.1 mmol) in CH2Cl2 (100 mL) to give a colorless solution at −55° C. under nitrogen. DMSO (5.54 mL, 78 mmol) was added dropwise over 10 min. After the solution was stirred for an additional 30 min, 6,7,8,9-tetrahydro-5H-cyclohepta[b]pyridin-6-ol (5.79 g, 35.5 mmol) (azeotroped with dry benzene) dissolved in 20 ml CH2Cl2 (plus 20 ml rinse) was added via canuula over 5 min. The reaction mixture was stirred at −50-−55° C. for an additional 40 min (the solution became milky). Et3N (24.74 mL, 178 mmol) was added via syringe at −50° C. and the reaction mixture was stirred for 30 min (Gel like and difficult to stir. Needs occasional shaking at ambient temperature). 100 ml water was added, and the layers were separated. The aqueous layer was extracted with CH2Cl2 (2×100 ml). The combined organic layers were dried with Na2SO4, and concentrated to a tan oil with some solids. Purification by FCC up to 10% MeOH/CH2Cl2 afforded the desired product as an orange oil (4.947 g, 86% for 4 steps). 1H NMR (500 MHz, CHLOROFORM-d) δ ppm 8.28-8.38 (m, 1H) 7.37 (d, J=7.63 Hz, 1H) 7.00-7.13 (m, 1H) 3.65 (s, 2H) 3.10-3.18 (m, 2H) 2.50-2.60 (m, 2H) 2.01 (dd, J=6.71, 4.88 Hz, 2H); 13C NMR (126 MHz, CHLOROFORM-d) δ ppm 207.23 (s, 1C) 160.24 (s, 1C) 147.98 (s, 1C) 137.20 (s, 1C) 128.85 (s, 1C) 122.25 (s, 1C) 48.89 (s, 1C) 43.96 (s, 1C) 36.15 (s, 1C) 24.70 (s, 1C).

Intermediate 25

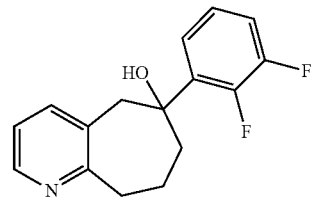

6-(2,3-Difluorophenyl)-6,7,8,9-tetrahydro-5H-cyclohepta[b]pyridin-6-ol. In an oven-dried 500 mL round-bottomed flask was BuLi (17.19 mL, 43.0 mmol) in THF (100 mL) to give a colorless solution at −78° C. under nitrogen. 1-Bromo-2,3-difluorobenzene (4.81 mL, 43.0 mmol) was added dropwise via syringe. The mixture was stirred at −78° C. for 20 min, and 8,9-dihydro-5H-cyclohepta[b]pyridin-6(7H)-one (4.947 g, 30.7 mmol) (azeotroped with dry benzene and dried under high vac) dissolved in 10 ml THF was added dropwise via canuula (plus 10 ml THF rinse). The mixture was warmed up to rt in 1 h. TLC showed some conversion to a slightly more polar spot. After quenched with saturated NH4Cl solution, THF was stripped off. The remaining mixture was partitioned between water and EtOAc. The layers were separated and the organic layer was washed with brine, dried with Na2SO4, and concentrated to a dark oil. The residue was purified by FCC up to 10% MeOH/CH2Cl2 (very difficult separation). The impure fractions were pooled and purified by FCC with EtOAc/CH2Cl2 up to pure EtOAc. The recovered SM: 1.88 g (38%). The product fractions were pooled and concentrated to a tan solid, which were washed repeatedly with Et2O to a tan solid (1.79 g, 21%). 1H NMR (400 MHz, CHLOROFORM-d) δ ppm 8.27 (dd, J=4.91, 1.38 Hz, 1H) 7.38-7.47 (m, 1H) 7.30-7.35 (m, 1H) 6.97-7.12 (m, 3H) 3.93 (dd, J=14.60, 2.52 Hz, 1H) 3.06-3.20 (m, 2H) 2.86 (dd, J=14.60, 1.76 Hz, 1H) 2.37-2.68 (m, 2H) 1.68-1.94 (m, 2H) 1.17 (t, J=7.05 Hz, 1H).

Intermediates 26 and 27

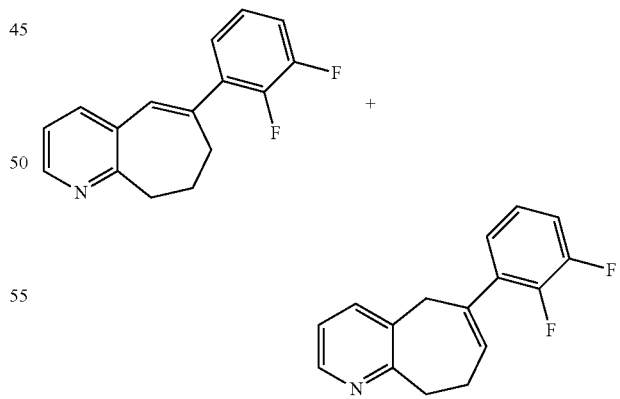

(E)-6-(2,3-Difluorophenyl)-8,9-dihydro-7H-cyclohepta[b]pyridine and (E)-6-(2,3-difluorophenyl)-8,9-dihydro-5H-cyclohepta[b]pyridine. In a 250 mL round-bottom flask was 6-(2,3-difluorophenyl)-6,7,8,9-tetrahydro-5H-cyclohepta[b]pyridin-6-ol (1.23 g, 4.47 mmol). HCl (20 mL 6M solution, 120 mmol) was added, and the mixture was heated at 100° C. (reflux) for 2 h. LCMS showed complete and clean conversion. After cooled to rt, it was diluted with EtOAc and slowly basified with 15 ml 10N NaOH. The layers were separated and the organic layer was washed with brine, dried and concentrated to a tan oil. FCC up to 80% EtOAc in hexane afforded the major peak (1) (0.71 g) as well as the minor peak (2) (90 mg) and some mixture of the two (0.34 g). Total: 1.14 g (97%: approximately 75% for 1 and 22% for 2). 1H NMR's confirmed both the structures. For (E)-6-(2,3-difluorophenyl)-8,9-dihydro-7H-cyclohepta[b]pyridine (1): 1H NMR (400 MHz, CHLOROFORM-d) δ ppm 8.33 (dd, J=5.04, 1.51 Hz, 1H) 7.40-7.51 (m, 1H) 6.98-7.18 (m, 4H) 6.53 (s, 1H) 3.04-3.22 (m, 2H) 2.63 (t, J=6.55 Hz, 2H) 2.17-2.32 (m, 2H). For (E)-6-(2,3-difluorophenyl)-8,9-dihydro-5H-cyclohepta[b]pyridine (2): 1H NMR (400 MHz, CHLOROFORM-d) δ ppm 8.35 (dd, J=4.91, 1.38 Hz, 1H) 7.39 (d, J=7.55 Hz, 1H) 6.81-7.10 (m, 4H) 5.67 (t, J=4.28 Hz, 1H) 3.73 (s, 2H) 3.23-3.34 (m, 2H) 2.48-2.65 (m, 2H).

Intermediate 28

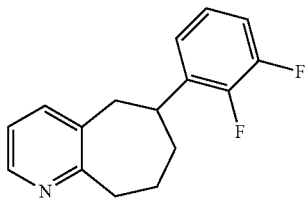

6-(2,3-Difluorophenyl)-6,7,8,9-tetrahydro-5H-cyclohepta[b]pyridine. In a 250 mL round-bottomed flask was (E)-6-(2,3-difluorophenyl)-8,9-dihydro-5H-cyclohepta[b]pyridine (112 mg, 0.435 mmol) in MeOH (4 mL) to give a colorless solution. Pd/C (46.3 mg, 0.044 mmol) was added, and the mixture was stirred under hydrogen balloon for 2 h. TLC showed one major peak as sm and LCMS showed both sm and product parent ions but co-eluted. Another 23 mg of Pd/C was added and the mixture was stirred under hydrogen overnight (19 h). LCMS showed complete conversion (a single peak with only product: M+H=260). It was filtered and washed with MeOH. The solution was concentrated to a colorless oil (106 mg, 94%). Crude 1H NMR confirmed the structure and showed excellent purity. 1H NMR (400 MHz, CHLOROFORM-d) δ ppm 8.30 (dd, J=4.78, 1.51 Hz, 1H) 7.35 (dd, J=7.55, 1.51 Hz, 1H) 6.89-7.12 (m, 4H) 3.17-3.31 (m, 1H) 3.01-3.17 (m, 2 H) 2.88-3.00 (m, 1H) 2.74 (d, J=14.10 Hz, 1H) 2.01-2.19 (m, 2H) 1.85-2.01 (m, 1H) 1.46-1.70 (m, 1H).

Intermediates 29 and 30

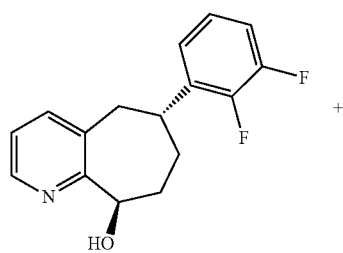

+

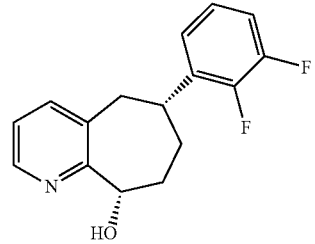

Racemic trans-6-(2,3-difluorophenyl)-6,7,8,9-tetrahydro-5H-cyclohepta[b]pyridin-9-ol and cis-6-(2,3-difluorophenyl)-6,7,8,9-tetrahydro-5H-cyclohepta[b]pyridin-9-ol. In a 100 mL round-bottomed flask was 6-(2,3-difluorophenyl)-6,7,8,9-tetrahydro-5H-cyclohepta[b]pyridine (106 mg, 0.409 mmol) in CH2Cl2 (4 ml) to give a colorless solution. mCPBA (137 mg, 0.613 mmol) was added and the resulted solution was stirred at rt overnight. 19 h: LCMS indicated complete conversion to the N-oxide. The mixture was diluted with EtOAc and washed with 1N NaOH solution. The organic layer was washed with brine, dried with Na2SO4, and concentrated in vacuo to a white solid. It was carried onto next reaction without further purification and characterizations. MS (ESI)[M+H+]=276.13. In a 100 mL round-bottomed flask was 6-(2,3-difluorophenyl)-6,7,8,9-tetrahydro-5H-cyclohepta[b]pyridine 1-oxide (113 mg, 0.409 mmol) (light yellow oil, azeotroped with dry benzene) in CH2Cl2 (4 mL) to give a light yellow solution. After cooling to 0° C., TFAA (0.144 mL, 1.023 mmol) was added, and the mixture was stirred at r.t. for 4 h. LCMS showed only 10% desired product and mainly SM (or maybe acylated N-oxide, slow rearrangement). Another 0.15 ml TFAA was added and the mixture was stirred at rt overnight. LCMS showed a little better. The mixture was refluxed at 45° C. for 4 h and the reaction didn't improve. Volatiles were stripped off and 2 ml acetic anhydride was added and the mixture was heated at 130° C. (preheated bath) for 1.5 h. LCMS showed no sm. It was cooled down and diluted with EtOAc. Basified with NaOH solution and the layers were separated. The organic layer was washed with water and concentrated to a tan oil. It was then dissolved in 2 ml THF and treated with 1.5 ml 1N NaOH for 1 h. LCMS showed mainly one peak as the desired product (M+H=276). The mixture was partitioned between EtOAc and water. The organic layer was separated and washed with brine, dried and concentrated to a tan oil. Purification by FCC up to 50% EtOAc/hexane afforded two compounds (very close spots on TLC): a and b. Further elution up to 80% EtOAc/hexane gave a more polar peak as c. As proved by 1H NMR, a was the desired trans-alcohol (32.3 mg, 29%) (the analytical data was the same as previously described); b was the dehydrated product (10.4 mg, 9.9%); and c was the cis-alcohol (36 mg, 32%). The cis-alcohol was much more polar that the trans-alcohol (Rf=0.16 for cis and 0.77 for trans in 50% EtOAc/hexanes). 1H NMR for the cis-alcohol: 1H NMR (500 MHz, CHLOROFORM-d) δ ppm 8.26 (d, J=4.58 Hz, 1H) 7.30 (d, J=7.63 Hz, 1H) 7.04 (dd, J=7.32, 4.88 Hz, 1H) 6.85-6.98 (m, 2H) 6.79 (t, J=6.87 Hz, 1H) 5.37 (br. s., 1 H) 5.01 (dd, J=7.17, 3.81 Hz, 1H) 3.28-3.52 (m, 2H) 2.93 (d, J=13.73 Hz, 1H) 2.17-2.33 (m, 1H) 1.89-2.15 (m, 3H).

Intermediate 31

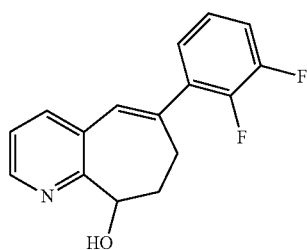

(E)-6-(2,3-Difluorophenyl)-8,9-dihydro-7H-cyclohepta[b]pyridin-9-ol. In a 250 mL round-bottomed flask was (E)-6-(2,3-difluorophenyl)-8,9-dihydro-7H-cyclohepta[b]pyridine (546 mg, 2.122 mmol) in CH2Cl2 (15 ml) to give a colorless solution. mCPBA (571 mg, 2.55 mmol) was added and the resulted solution was stirred at rt overnight. 4 h: LCMS showed only trace SM left. 21 h: The mixture was diluted with EtOAc and washed with 1N NaOH solution. The organic layer was washed with water, brine, dried with Na2SO4, and concentrated in vacuo to a dense oil (100%). It was carried onto next reaction without further purification and characterizations. MS (ESI)[M+H$^+$]=274.19. Ref: Kaiser, S.; Smidt, S. P.; Pfaltz, A. *Angew. Chem. Int. Ed.* 2006, 45, 5194-5197. In a 100 mL round-bottomed flask was (E)-6-(2,3-difluorophenyl)-8,9-dihydro-7H-cyclohepta[b]pyridine 1-oxide (0.580 g, 2.122 mmol) (azeotroped with dry benzene) in CH2Cl2 (16 mL) to give a colorless solution. After cooling to 0° C., TFAA (0.749 mL, 5.31 mmol) was added, and the mixture was stirred at r.t. for 4 h. It was left in fridge over weekend. LiOH (6.37 mL, 6.37 mmol) was added and the mixture was stirred for 2 h. It was diluted with EtOAc and water and the layers were separated. The organic layer was washed with brine, dried and concentrated to a tan oil. Purification by FCC up to 50% EtOAc/hexane afforded the product as a yellowish oil/solids (0.4 g, 69% for 2 steps). MS (ESI)[M+H$^+$]=274.19; 1H NMR (400 MHz, CHLOROFORM-d) δ ppm 8.36 (dd, J=4.78, 1.51 Hz, 1H) 7.50 (dd, J=7.81, 1.26 Hz, 1H) 7.20 (dd, J=7.68, 4.91 Hz, 1H) 6.96-7.11 (m, 3H) 6.44 (s, 1H) 5.63 (br., 1H) 4.77 (dd, J=10.45, 2.64 Hz, 1 H) 2.78-2.95 (m, 1H) 2.64-2.77 (m, 1H) 2.44-2.62 (m, J=13.60, 5.48, 5.48, 2.64 Hz, 1H) 1.92-2.15 (m, 1H); 13C NMR (101 MHz, CHLOROFORM-d) δ ppm 158.49 (s, 1C) 149.39-152.62 (m, 1C) 146.03-149.25 (m, 1C) 145.24 (s, 1C) 143.70 (s, 1C) 139.94 (s, 1C) 138.79 (s, 1C) 134.46 (d, J=10.79 Hz, 1C) 128.51 (d, J=11.56 Hz, 1C) 124.37 (br. s., 1C) 123.81-124.14 (m, 1C) 122.44 (s, 1C) 116.24 (d, J=16.95 Hz, 1C) 71.49 (s, 1C) 34.88 (s, 1C) 32.74 (d, J=3.08 Hz, 1C).

Intermediates 32 and 33

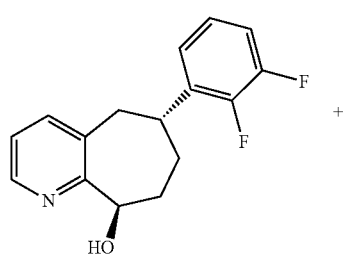

+

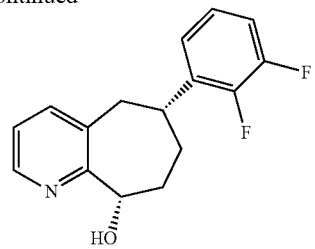

Racemic trans-6-(2,3-difluorophenyl)-6,7,8,9-tetrahydro-5H-cyclohepta[b]pyridin-9-ol and cis-6-(2,3-difluorophenyl)-6,7,8,9-tetrahydro-5H-cyclohepta[b]pyridin-9-ol. In a 500 mL round-bottomed flask was (E)-6-(2,3-difluorophenyl)-8,9-dihydro-7H-cyclohepta[b]pyridin-9-ol (660 mg, 2.415 mmol) in MeOH (20 mL) to give a colorless solution. Pd/C (257 mg, 0.242 mmol) was added, and the mixture was stirred under hydrogen balloon for 4 h. LCMS showed complete conversion. Filtered and concentrated to a colorless oil. Purification by FCC up to 80% EtOAc/hexane afforded two products: trans-alcohol (104.3 mg, 16%), and cis-alcohol (492.8 mg, 74%), both as white solids. Analytical data of both alcohols matched that of previously described.

Intermediate 34

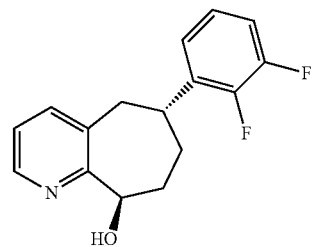

Racemic (6,9-trans-6-(2,3-difluorophenyl)-6,7,8,9-tetrahydro-5H-cyclohepta[b]pyridin-9-ol. In a 100 mL round-bottomed flask was (6,9-cis)-6-(2,3-difluorophenyl)-6,7,8,9-tetrahydro-5H-cyclohepta[b]pyridin-9-ol (489 mg, 1.776 mmol) (azeotroped with dry benzene) in THF (15 mL) to give a colorless solution. 4-Nitrobenzoic acid (594 mg, 3.55 mmol) and Ph3P (932 mg, 3.55 mmol) were added, and the mixture was cooled to 0° C. Diisopropyl azodicarboxylate (0.699 mL, 3.55 mmol) was added dropwise. The mixture was allowed to warm up to rt and stirred for 5 h. LCMS indicated complete conversion to the desired intermediate and a little dehydrated product. It was left stirring overnight and LCMS showed no change. LiOH (8.88 mL, 8.88 mmol) was added, and the mixture was stirred at rt for 3 h. LCMS indicated complete conversion of the intermediate to product. THF was stripped off and the residue was partitioned between EtOAc and 0.2N NaOH. The layers were separated and the organic was washed with brine, dried, and concentrated to a slightly tan oil. FCC up to 50% EtOAc/hexane afforded the desired product (378 mg, 77%) as a white solid. The analytical data matched that of previously described.

Intermediate 35

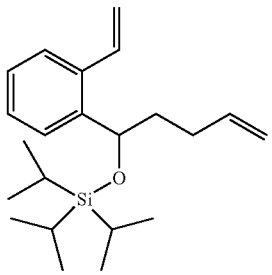

Triisopropyl(1-(2-vinylphenyl)pent-4-enyloxy)silane. 1-Bromo-2-vinylbenzene (2.8146 g, 15.38 mmol) was azeotropped by dry benzene twice before taken up in THF (50 ml). The solution was cooled to −78° C. BuLi (6.77 ml, 16.91 mmol) was added to the reaction mixture at −78° C. and stirred for 20 min at this temperature. pent-4-enal (1.670 ml, 16.91 mmol) was added to the reaction mixture and stirred for 4 hours while the bath temperature gradually warmed up. Chlorotriisopropylsilane (3.58 ml, 16.91 mmol) was added to the reaction mixture and the reaction was stirred overnight while the reaction was warmed up to room temperature. The solvent was mostly removed via vacuum and the crude was partitioned between ethyl acetate and water. The ethyl acetate layer was separated, dried (Na2SO4), filtered and concentrated. The product was obtained by flash column eluted with ether in hexane from 0 to 30% (3.9 g, 74% yield). MS (ESI) [M+H$^+$]=346.46.

Intermediate 36

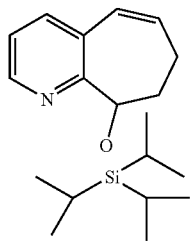

(Z)-9-(Triisopropylsilyloxy)-8,9-dihydro-7H-cyclohepta[b]pyridine. Hydrogen chloride (5.64 mL, 11.28 mmol) (10 mL, 2M diethyl ether solution) was added to the CH2Cl2 (25 mL) solution of 2-(1-(triisopropylsilyloxy)pent-4-enyl)-3-vinylpyridine (3.9 g, 11.28 mmol). The solvent was removed via vacuum and the corresponding HCl salt was azeotroped by benzene twice. The reaction was charged with CH2Cl2 (500 mL) and purged with N2 for 10 min before addition of Grubb II (0.192 g, 0.226 mmol). The reaction was heat to 40° C. for 3 hours, LCMS showed no starting material left. The reaction was washed with saturated NaHCO3 solution once. The CH2Cl2 was separated, dried (Na2SO4), filtered and concentrated. Flash column by ether in hexane from 0 to 25% gave the desired product as yellow oil (2.54 g, 71% yield). MS (ESI)[M+H$^+$]=318.35.

Intermediate 37

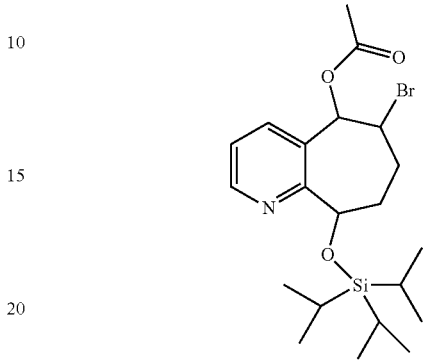

6-Bromo-9-(triisopropylsilyloxy)-6,7,8,9-tetrahydro-5H-cyclohepta[b]pyridin-5-yl acetate. N-bromoacetamide (2.021 g, 14.65 mmol) was added to the AcOH (100 mL) suspension of (Z)-9-(triisopropylsilyloxy)-8,9-dihydro-7H-cyclohepta[b]pyridine (4.5597 g, 14.36 mmol) and LITHIUM ACETATE (3.79 g, 57.4 mmol) at rt under N2. The flask was wrapped with alumina foil and stirred at room temperature overnight. The reaction became a clear yellow solution. The solvent was evaporated via high vacuum. The crude was partitioned between water and ethyl acetate. Na2CO3 was added until no bubbling. The organic was separated and the aqueous was extract by ethyl acetate again. The combined organic layer was dried (Na2SO4), filtered and concentrated to give a tan oil (crude product: 6.37 g). The crude was used as it is. MS (ESI)[M+H$^+$]=458.36.

Intermediate 38

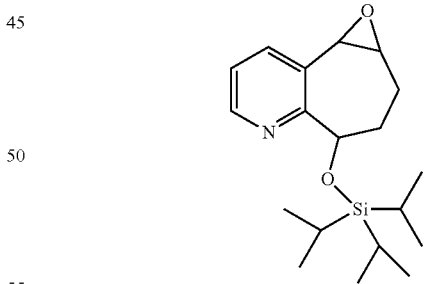

6-Bromo-9-(triisopropylsilyloxy)-6,7,8,9-tetrahydro-5H-cyclohepta[b]pyridin-5-yl acetate epoxide. Sodium methoxide (3.77 g, 69.8 mmol) was added to the THF (100 mL) solution of 6-bromo-9-(triisopropylsilyloxy)-6,7,8,9-tetrahydro-5H-cyclohepta[b]pyridin-5-yl acetate (6.37 g, 13.95 mmol) at rt under N2. The reaction was stirred for 2 hours. TLC showed no more starting material and the product was a more polar spot than starting material. The solvent was removed via vacuum and the crude was partitioned between ethyl acetate and water. The aqueous layer was extract again by ethyl acetate. The combined organic layer was dried (Na2SO4), filtered and concentrated to give the crude product as a tan oil (crude product: 4.22 g, 91%). MS (ESI)[M+H$^+$]= 334.30.

Intermediate 39

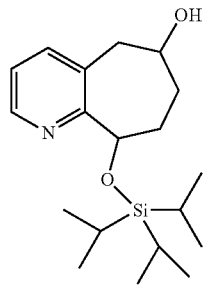

9-(Triisopropylsilyloxy)-6,7,8,9-tetrahydro-5H-cyclohepta[b]pyridin-6-ol. The mixture of the epoxide (4.22 g, 12.65 mmol), PALLADIUM ON CARBON (0.45 g, 0.423 mmol) in MeOH (100 mL) was hydrogenated at room temperature by H2 balloon for 2 hours. TLC showed no more starting material and a more polar spot as the desired product. The reaction was filtered through a silica pad and washed with methanol. The filtrate was concentrated to give the desired product as a tan oil (crude 4.1 g, 97%). MS (ESI)[M+H$^+$]= 336.37.

Intermediate 40

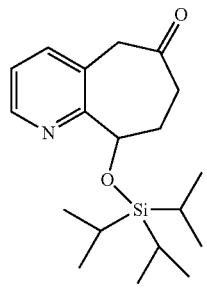

9-(Triisopropylsilyloxy)-8,9-dihydro-5H-cyclohepta[b]pyridin-6(7H)-one. In an oven dried 500 mL round bottom flask was charged with OXALYL CHLORIDE (6.49 mL, 72.9 mmol), CH2Cl2 (150 mL) under N2. The flask was cooled to −60° C. and DMSO (6.90 mL, 97 mmol) was added to the reaction mixture dropwise. After finish addition, the reaction was stirred at −60° C. for 30 min before cannula the 9-(triisopropylsilyloxy)-6,7,8,9-tetrahydro-5H-cyclohepta[b]pyridin-6-ol (8.1557 g, 24.31 mmol) (dissolved in 20 mL CH2Cl2 and rinsed with 20 mL CH2Cl2) to the reaction mixture at −60° C. The reaction was stirred at −55° C. for 40 min before addition of TEA (16.94 mL, 122 mmol). The reaction seems formed a thick suspension. The reaction was stirred for 1 hour and water was added to the reaction mixture. The organic layer was separated and the aqueous layer was extract by CH2Cl2 twice. The CH2Cl2 layer was combined, dried (Na2SO4), filtered and concentrated. Flash column by ethyl acetate in hexane from 25% to 50% gave the product as yellow oil (1.49 g, 18.4%). MS (ESI)[M+H$^+$]=334.30; 1H NMR (400 MHz, CHLOROFORM-d) δ ppm 8.36 (d, J=5.04 Hz, 1H) 7.46 (d, J=7.55 Hz, 1H) 7.16 (dd, J=7.55, 4.78 Hz, 1H) 5.22 (dd, J=4.78, 2.27 Hz, 1H) 4.66 (d, J=14.35 Hz, 1H) 3.26 (d, J=14.60 Hz, 1H) 2.94-3.05 (m, 1H) 2.42-2.55 (m, 1H) 2.36 (dd, J=14.10, 5.04 Hz, 1H) 2.03-2.17 (m, 1H) 1.03-1.16 (m, 3H) 0.96-1.00 (m, 9H) 0.89-0.92 (m, 9H).

Intermediate 41

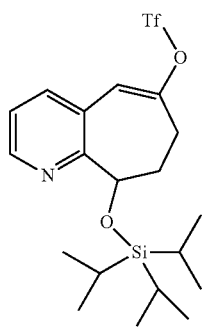

(E)-9-(Triisopropylsilyloxy)-8,9-dihydro-7H-cyclohepta[b]pyridin-6-yl trifluoromethanesulfonate. LDA (3.73 mL, 7.45 mmol) was added to the THF (25 mL) solution of DMPU (2.073 mL, 17.20 mmol) and 9-(triisopropylsilyloxy)-8,9-dihydro-5H-cyclohepta[b]pyridin-6(7H)-one (1.9119 g, 5.73 mmol) at −78° C. The reaction was stirred at this temperature for 2 hours before addition of 1,1,1-trifluoro-N-phenyl-N-(trifluoromethylsulfonyl)methanesulfonamide (2.66 g, 7.45 mmol). The reaction was stirred for overnight while it was gradually warmed up to room temperature. The solvent was removed via vacuum and the crude was loaded on the flash column, eluted with ethyl acetate in hexane from 0 to 15% to 25% to afford the desired product (2.3 g, 86%). MS (ESI)[M+H$^+$]=466.33; 1H NMR (400 MHz, CHLOROFORM-d) δ ppm 8.37 (dd, J=4.78, 1.51 Hz, 1H) 7.47-7.54 (m, 1H) 7.20 (dd, J=7.81, 4.78 Hz, 1H) 6.43 (d, J=2.01 Hz, 1H) 5.26 (d, J=7.55 Hz, 1H) 3.16-3.32 (m, 1H) 2.58-2.69 (m, 1H) 2.29-2.39 (m, 1H) 1.85-1.98 (m, 1H) 1.01-1.09 (m, 3H) 0.93-1.00 (m, 9H) 0.85 (d, J=7.05 Hz, 9H).

Intermediate 42

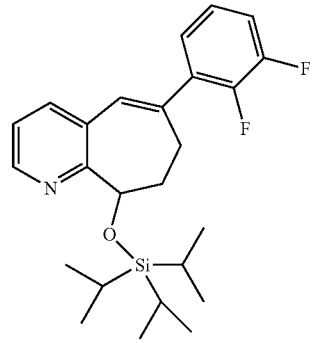

(E)-6-(2,3-difluorophenyl)-9-(triisopropylsilyloxy)-8,9-dihydro-7H-cyclohepta[b]pyridine. The mixture of 2,3-difluorophenylboronic acid (0.936 g, 5.93 mmol), sodium carbonate (4.57 mL, 9.14 mmol), (E)-9-(triisopropylsilyloxy)-8,9-dihydro-7H-cyclohepta[b]pyridin-6-yl trifluoromethanesulfonate (2.3 g, 4.94 mmol) and tetrakis (triphenylphosphine)palladium(0) (0.285 g, 0.247 mmol) in toluene (30 mL) and MeOH (6 mL) was heat to 80° C. under N2 for 3 hours. LCMS showed no more starting material. The reaction was diluted with ethyl acetate and washed with water one time. The ethyl acetate layer was separated, dried (Na2SO4), filtered and concentrated. Flash column by ethyl acetate in hexane from 0 to 25% afforded the desired product (0.8797 g, 54%). MS (ESI)[M+H$^+$]=430.43.

Intermediate 43

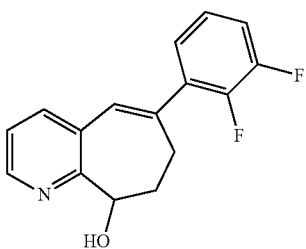

(E)-6-(2,3-difluorophenyl)-8,9-dihydro-7H-cyclohepta [b]pyridin-9-ol. The mixture of (E)-6-(2,3-difluorophenyl)-9-(triisopropylsilyloxy)-8,9-dihydro-7H-cyclohepta[b]pyridine (1.6072 g, 3.74 mmol) and TBAF (7.48 mL, 7.48 mmol) in THF (10 mL) was stirred at room temperature for 1 hour. LCMS showed no more starting material and conversion of the desired product. The solvent was removed via vacuum. The reaction was purified by flash column eluted with ethyl acetate in hexane from 0 to 35% to 50% to afford the desired product as a white solid (0.825 g, 81%). All analytical data matched that of previously described.

Intermediate 44

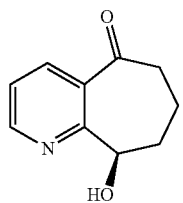

(R)-9-hydroxy-6,7,8,9-tetrahydro-5H-cyclohepta[b]pyridin-5-one. In a 1 L round-bottomed flask was (S)-9-hydroxy-6,7,8,9-tetrahydro-5H-cyclohepta[b]pyridin-5-one (19.14 g, 108 mmol) (obtained by enzyme reduction of the diketone) in THF (300 mL) to give a light orange solution. 4-Nitrobenzoic acid (27.1 g, 162 mmol) and Ph3P (42.5 g, 162 mmol) were added under nitrogen, and the mixture was cooled to 0° C. Diisopropyl azodicarboxylate (31.9 mL, 162 mmol) was added dropwise. The mixture was allowed to gradually warm to rt and stirred overnight (5:00 pm). The color changed to tan. 15 h: LCMS showed complete conversion. 80 ml water was added followed by LiOH (7.76 g, 324 mmol). The mixture was stirred at rt for 2 h (some LiOH was not completely dissolved). 2 h: LCMS showed complete conversion (product/dehydrated ~7/1 by intergration). THF was stripped off and the remaining mixture was slowly acidified with 40 ml concentrated HCl (12N). 300 ml EtOAc was added. The mixture was shaken in a 1 L separating funnel (10 ml hexane was added for better separation). The layers were separated and the organic layer was extracted with water (2×50 mL). The combined aqueous layers were washed with EtOAc (4×100 mL). The tan aqueous solution was then basified slowly with 50 mL 10N NaOH and was extracted with EtOAc (4×150 mL). The aqueous layer was saturated with NaCl and extracted with EtOAc (2×100 mL). The combined tan organic layers (TLC showed desired product, dehydrated product and some baseline) were washed with brine, dried and concentrated to a tan oil (crude weight: 19.24 g, 100%), which was directly used in the next step. MS (ESI)[M+H$^+$]=178.24.

Intermediate 45

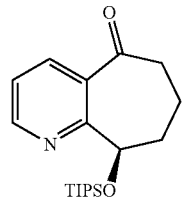

(R)-9-(Triisopropylsilyloxy)-6,7,8,9-tetrahydro-5H-cyclohepta[b]pyridin-5-one. In a 1 L round-bottomed flask was (R)-9-hydroxy-6,7,8,9-tetrahydro-5H-cyclohepta[b]pyridin-5-one (19.14 g, 108 mmol) (azeotroped with dry benzene) in CH2Cl2 (300 mL) to give a tan solution. After cooling to 0° C., TIPS-OTf (29.3 mL, 108 mmol) and Et3N (30.1 mL, 216 mmol) were added via syringe, and the mixture was stirred at 0° C. for 1 h. LCMS indicated complete conversion. Volatiles were stripped off and the residue was partitioned between NaHCO3 solution and EtOAc. The layers were separated and the organic layer was washed with brine, dried and concentrated to a tan oil (37 g). It was purified by FCC up to 20% EtOAc/hexane to afford the product as a white solid (26.3 g, 73% for two steps). MS (ESI)[M+H$^+$]=334.37.

Intermediate 46

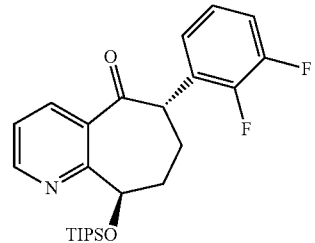

(6S,9R)-6-(2,3-Difluorophenyl)-9-(triisopropylsilyloxy)-6,7,8,9-tetrahydro-5H-cyclohepta[b]pyridin-5-one. See Fox, J. M.; Huang, X.; Chieffi, A.; Buchwald, S. L. *J. Am. Chem. Soc.* 2000, 122, 1360-1370. In an oven-dried 1 L flask was Sodium tert-butoxide (13.19 g, 137 mmol), PALLADIUM (II) ACETATE (0.948 g, 4.22 mmol), and 2-(Dicyclohexylphosphino)-2'-methylbiphenyl (1.539 g, 4.22 mmol) weighed in a nitrogen bag. (R)-9-(triisopropylsilyloxy)-6,7,8,9-tetrahydro-5H-cyclohepta[b]pyridin-5-one (35.21 g, 106 mmol), Toluene (106 mL) (degassed in the original bottle by nitrogen gas), and 1-bromo-2,3-difluorobenzene (14.18 mL, 127 mmol) were added under nitrogen. The flask stirred at 80° C. in a pre-heated oil bath for 20 h. Volatiles were stripped off and the residue was partitioned between EtOAc (400 ml) and water (400 ml). The layers were separated. The aqueous layer was extracted with EtOAc (50 ml). The combined organic layer was washed with brine, dried and concentrated to a dark oil. It was passed through a plug of silica gel (loaded with CH2Cl2 and eluted with EtOAc/hexane up to 30% EtOAc). The crude product was obtained as a dark red oil (86% mass recovery). 1H NMR showed approximately 6/1 ratio of the desired trans isomer to the cis isomer. MS (ESI)[M+H$^+$]= 446.21.

Intermediate 47

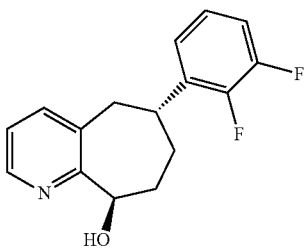

(6R,9R)-6-(2,3-difluorophenyl)-6,7,8,9-tetrahydro-5H-cyclohepta[b]pyridin-9-ol. In a 250 mL round-bottomed flask was (9R)-6-(2,3-difluorophenyl)-9-(triisopropylsilyloxy)-6,7,8,9-difluorophenyl)-9-(triisopropylsilyloxy)-6,7,8,9-tetrahydro-5H-cyclohepta[b]pyridin-5-one (9.59 g, 21.52 mmol) in MeOH (50 mL) to give a light yellow solution. NaBH4 (1.628 g, 43.0 mmol) was added, and the mixture was stirred at rt for 40 min. LCMS indicated complete conversion (a major peak and a minor peak of isomers). 1 h: MeOH was stripped off in vacuo and the residue was partitioned between water and EtOAc. The layers were separated. The organic layer was washed with brine, dried, and concentrated to a light yellow oil (9.63 g, 100%). MS (ESI)[M+H$^+$] =448.40. In a 500 mL round-bottomed flask was (9R)-6-(2, 3-difluorophenyl)-9-(triisopropylsilyloxy)-6,7,8,9-tetrahydro-5H-cyclohepta[b]pyridin-5-ol (9.63 g, 21.52 mmol) (azeotroped with dry benzene) in CH2Cl2 (100 mL) to give a light yellow solution. After cooling to 0° C. in an ice bath, Ms-Cl (1.845 mL, 23.67 mmol) and Et3N (9.00 mL, 64.6 mmol) were added slowly via syringe under nitrogen. The cooling bath was removed after 30 min, and the mixture was stirred at rt for 2 h (color changed to reddish tan). LCMS showed complete conversion. The solvent was stripped off and the residue was partitioned between NaHCO3 solution and EtOAc (150 ml). The layers were separated. The organic layer was washed with brine, dried and concentrated to a yellow oil, and dried overnight (10.82 g, 96%). MS (ESI)[M+H$^+$]=526.28. In a 500 mL round-bottomed flask was (9R)-6-(2,3-difluorophenyl)-9-(triisopropylsilyloxy)-6,7,8,9-tetrahydro-5H-cyclohepta[b]pyridin-5-yl methanesulfonate (11.31 g, 21.52 mmol) in THF (100 mL) to give a light yellow solution. LAH (16.14 mL, 32.3 mmol) (2M in THF) was added slowly via syringe under nitrogen, and the mixture was stirred at rt for 1 h (color turned to red). LCMS indicated complete conversion. Anhydrous Na2SO4 was added and the reaction was slowly quenched with water. Gel was formed. Combination of filtration and aqueous workup afforded a light yellow oil. Purification by FCC up to 70% EtOAc/hexane afforded the first peak the desired product as a dense tan oil (dried over 4 days: 1.44 g, 24%), 1H NMR and HPLC/LCMS of which matched previously described racemate. Up to 22% of the various hydrolyzed diols could be recovered.

Intermediate 48

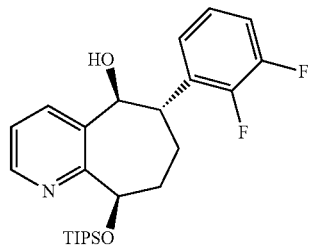

(5S,6S,9R)-6-(2,3-Difluorophenyl)-9-(triisopropylsilyloxy)-6,7,8,9-tetrahydro-5H-cyclohepta[b]pyridin-5-ol. In a 1 L round-bottomed flask was (9R)-6-(2,3-difluorophenyl)-9-(triisopropylsilyloxy)-6,7,8,9-tetrahydro-5H-cyclohepta[b]pyridin-5-one (48 g, 108 mmol) in cyclopentylmethylether (400 mL) to give a tan solution. After cooling to −15° C. in an ice-MeOH bath, LITHIUM BOROHYDRIDE (9.39 g, 431 mmol) was added, and the mixture (heterogeneous) was gradually warmed up to 10° C. in 4 h and stirred at rt for 30 min. LCMS indicated very good conversion. It was slowly quenched with 30 ml MeOH and most volatiles were stripped off under high vac. The remaining was diluted with EtOAc and slowly quenched with water with good stirring. The mixture was stirred at rt overnight. The layers were separated. The dark organic layer was washed with brine, dried, and concentrated to a dark oil (48 g, 100%). It was directly carried onto next reaction. MS (ESI)[M+H$^+$]=448.14.

Intermediate 49

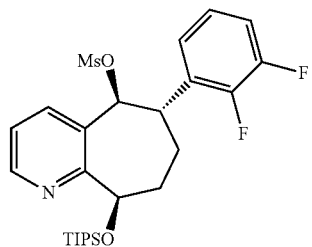

(5S,6S,9R)-6-(2,3-difluorophenyl)-9-(triisopropylsilyloxy)-6,7,8,9-tetrahydro-5H-cyclohepta[b]pyridin-5-yl methanesulfonate. In a 1 L round-bottomed flask was (5S,6S,9R)-6-(2,3-difluorophenyl)-9-(triisopropylsilyloxy)-6,7,8,9-tetrahydro-5H-cyclohepta[b]pyridin-5-ol (47.17 g, 105 mmol) (azeotroped with dry benzene) in C6H5CF3 (500 mL) to give a tan solution. Ms-Cl (24.63 mL, 316 mmol) was added at 0° C. followed by Et3N (73.4 mL, 527 mmol) in a dropping funnel under nitrogen (11:00 am). After dropwise addition of Et3N, the suspension was stirred at rt for 2 h. LCMS showed majorly product parent ion (overlapped with sm in LCMS). The solvent was stripped off and the residue was slowly treated with NaHCO3 solution (300 ml). EtOAc (400 ml) was added. The layers were separated and the aqueous layer was extracted with EtOAc (100 ml). The combined organic layers were washed with brine, dried and concentrated to a tan oil, which was used the next reaction without further purification and characterizations. MS (ESI)[M+H⁺]= 526.14.

Intermediate 50

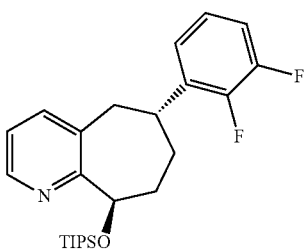

(6R,9R)-6-(2,3-Difluorophenyl)-9-(triisopropylsilyloxy)-6,7,8,9-tetrahydro-5H-cyclohepta[b]pyridine. In a 2l flask was (5S,6S,9R)-6-(2,3-difluorophenyl)-9-(triisopropylsilyloxy)-6,7,8,9-tetrahydro-5H-cyclohepta[b]pyridin-5-yl methanesulfonate (55.2 g, 105 mmol) (azeotroped with dry benzene) in THF (300 mL) to give a tan solution. Superhydride (525 mL, 525 mmol) (1.0M in THF) was added dropwise via dropping funnel under nitrogen, and the mixture was stirred at rt for 4 h. THF was stripped off and the tan oil was partitioned between water (300 ml) and EtOAc (400 ml). The layers were separated and the organic layer was washed with brine, dried and concentrated to a tan oil (close to 60 g). Purification by FCC (2.5 L packed column) up to 30% EtOAc/hexane did not give good purification but did get rid of baseline (not very uv active) junk (use just a silica plug and <10% EtOAc/hexane should be ok too). All the collected less polar fractions were combined and concentrated to a tan oil (33.58 g) and was directly used in the next step. MS (ESI) [M+H⁺]=432.19.

Intermediate 51

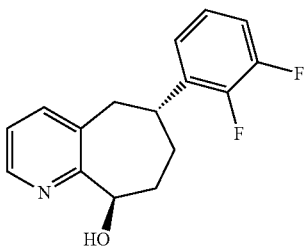

(6R,9R)-6-(2,3-difluorophenyl)-6,7,8,9-tetrahydro-5H-cyclohepta[b]pyridin-9-ol. In a 1 L round-bottomed flask was (6R,9R)-6-(2,3-difluorophenyl)-9-(triisopropylsilyloxy)-6,7,8,9-tetrahydro-5H-cyclohepta[b]pyridine (19.58 g, 45.4 mmol) in THF (400 mL) to give a tan solution. TBAF (54.4 mL, 54.4 mmol) was added via syringe and the mixture was stirred at rt overnight. 15 h: LCMS indicated complete conversion. THF was stripped off. The residue was combined with 78213-100 and partitioned between 400 ml EtOAc and 300 ml water. The layers were separated. The aqueous layer was extracted with EtOAc (50 ml). The combined organic layers were washed with brine, dried and concentrated to a tan oil. Careful purification by FCC with gradient up to 20% EtOAc/hexane can remove the slightly less polar spot. All products were subjected to recrystallization from MeOH. An X-ray structure was obtained. The overall yield from the TIPS-protected hydroxyketone was over 26%. All analytical data matched that of previously described. MS (ESI)[M+H⁺]= 276.15; 1H NMR (500 MHz, CHLOROFORM-d) δ ppm 8.45 (d, J=4.88 Hz, 1H) 7.50 (d, J=7.63 Hz, 1H) 7.20 (dd, J=7.48, 5.04 Hz, 1H) 7.01-7.11 (m, 3H) 4.92 (dd, J=11.29, 2.14 Hz, 1H) 3.18-3.30 (m, 1H) 2.90-2.99 (m, 1H) 2.84 (d, J=14.04 Hz, 1H) 2.33-2.43 (m, 1H) 2.16-2.26 (m, 2H) 1.56-1.73 (m, 1 H).

Intermediate 52

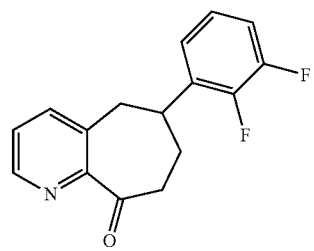

6-(2,3-Difluorophenyl)-7,8-dihydro-5H-cyclohepta[b]pyridin-9(6H)-one. In an oven-dried 100 mL round-bottomed flask was OXALYL CHLORIDE (0.131 mL, 1.497 mmol) in CH2Cl2 (4 mL) to give a colorless solution at −55° C. under nitrogen. DMSO (0.212 mL, 2.99 mmol) was added dropwise over 10 min. After the solution was stirred for an additional 30 min, (6R,9R)-6-(2,3-difluorophenyl)-6,7,8,9-tetrahydro-5H-cyclohepta[b]pyridin-9-ol (206 mg, 0.748 mmol) (racemic, azeotroped with dry benzene) dissolved in 2 ml CH2Cl2 (plus 2 ml rinse) was added via canuula over 5 min. The reaction mixture was stirred at −50-−55° C. for an additional 40 min (the solution became milky). Et3N (0.521 mL, 3.74 mmol) was added via syringe at −50° C. and the reaction mixture was stirred for 30 min. Water and EtOAc were added, and the layers were separated. The aqueous layer was extracted with EtOAc. The combined organic layers were dried with Na2SO4, and concentrated to a tan oil. TLC (1/1 EtOAc/hexane) showed two spots: the major more polar (comparable to cis-alcohol) and a little SM. Purification by FCC up to 60% EtOAc/hexane afforded the desired product as a colorless oil (148 mg, 72%), plus a little recovered sm. MS (ESI)[M+H⁺] =274.30. 1H NMR (400 MHz, CHLOROFORM-d) δ ppm 8.57 (dd, J=4.66, 1.64 Hz, 1H) 7.39 (d, J=7.81 Hz, 1H) 7.20-7.31 (m, 1H) 6.83-7.04 (m, 2H) 6.72 (t, J=6.92 Hz, 1H) 3.50 (dd, J=9.32, 6.30 Hz, 1H) 3.09 (d, J=6.30 Hz, 2H) 2.84-2.99 (m, 1H) 2.68-2.84 (m, 1H) 2.03-2.17 (m, 1H) 1.85-2.02 (m, 1 H); 13C NMR (100 MHz, CHLOROFORM-d) δ ppm 203.43, 154.56, 152.00-149.39 (dd, J=13.4 and 247 Hz), 149.52-146.94 (dd, J=12.5 and 247 Hz), 148.83, 138.77, 134.44, 134.22 (d, J=11.0 Hz), 125.87, 124.16, 122.36, 115.40 (d, J=17.0 Hz), 39.62, 36.83, 35.19, 27.33.

Intermediate 53

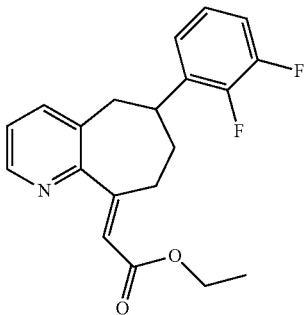

(E)-Ethyl 2-(6-(2,3-difluorophenyl)-7,8-dihydro-5H-cyclohepta[b]pyridin-9(6H)-ylidene)acetate. See Nagarajan, S. R. et al. *Bioorg. Med. Chem.* 2007, 15, 3390-3412. In a 100 mL round-bottomed flask was 6-(2,3-difluorophenyl)-7,8-dihydro-5H-cyclohepta[b]pyridin-9(6H)-one (148 mg, 0.542 mmol) (azeotroped with dry benzene) in Toluene (6 mL) to give a colorless solution. Ethyl (triphenylphosphoranylidene) acetate (208 mg, 0.596 mmol) was added, and the mixture was heated at reflux overnight (4:30 pm). 16 h: LCMS showed complete conversion to the desired product. TLC (1/1 EtOAc/hexane) showed one main less polar (a little less polar than the starting trans-alcohol). Toluene was stripped off and the residue was purified by FCC up to 50% EtOAc/hexane to provide the desired product as a colorless oil (139 mg, 75%). Both 1H NMR and 13C NMR were taken and confirmed the structure to be a single isomer. MS (ESI)[M+H$^+$]=346.46; 1H NMR (400 MHz, CHLOROFORM-d) δ ppm 8.43 (dd, J=4.78, 1.76 Hz, 1H) 7.33 (dd, J=7.55, 1.51 Hz, 1H) 7.13 (dd, J=7.55, 4.78 Hz, 1H) 6.91-7.00 (m, 2H) 6.80-6.90 (m, 1H) 6.36 (s, 1H) 4.17 (q, J=7.05 Hz, 2H) 3.25-3.43 (m, 2H) 3.04-3.14 (m, 1H) 2.93-3.05 (m, 1H) 2.88 (dd, J=14.86, 3.27 Hz, 1H) 2.04-2.21 (m, 1H) 1.83-2.02 (m, 1H) 1.25 (t, J=7.05 Hz, 3H); 13C NMR (100 MHz, CHLOROFORM-d) δ ppm 166.45, 159.22, 158.59, 151.99-149.47 (dd, J=13.4 and 247 Hz), 149.39-146.90 (dd, J=12.7 and 245 Hz), 147.55, 137.88, 135.46 (d, J=11.4 Hz), 133.41, 123.98, 123.25, 122.43, 120.89, 115.09 (d, J=16.9 Hz), 59.94, 38.62, 36.30, 32.49, 28.85, 14.27.

Intermediate 54

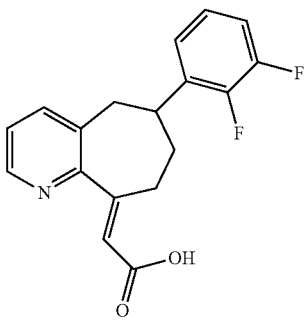

(E)-2-(6-(2,3-Difluorophenyl)-7,8-dihydro-5H-cyclohepta[b]pyridin-9(6H)-ylidene)acetic acid. In a 50 mL round-bottomed flask was (E)-ethyl 2-(6-(2,3-difluorophenyl)-7,8-dihydro-5H-cyclohepta[b]pyridin-9(6H)-ylidene) acetate (11.8 mg, 0.034 mmol) in THF (1 ml) to give a colorless solution. LiOH (0.2 ml, 0.200 mmol) was added and the mixture was stirred at rt overnight (4:30 pm). 16 h: LCMS indicated a little sm left. 0.5 ml MeOH was added and the mixture was stirred for another 24 h. LCMS indicated complete conversion. Concentrated and further dried under a high vac to remove water to a white solid. It was further dried by azeotroping with dry benzene and under high vac for 4 h. The white solid was then directly subject to next reaction. MS (ESI)[M+H$^+$]=316.21.

Intermediate 55

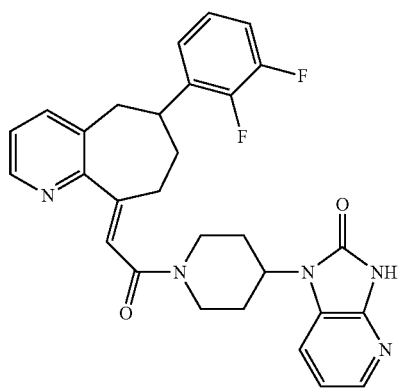

(E)-1-(1-(2-(6-(2,3-Difluorophenyl)-7,8-dihydro-5H-cyclohepta[b]pyridin-9(6H)-ylidene)acetyl)piperidin-4-yl)-1H-imidazo[4,5-b]pyridin-2(3H)-one. In a 100 mL round-bottomed flask was (E)-2-(6-(2,3-difluorophenyl)-7,8-dihydro-5H-cyclohepta[b]pyridin-9(6H)-ylidene)acetic acid (10.72 mg, 0.034 mmol) and 1-(piperidin-4-yl)-1H-imidazo[4,5-b]pyridin-2(3H)-one (22.26 mg, 0.102 mmol) (bis-HCl salt) in CH2Cl2 (2 ml) to give a colorless suspension. Hunig's Base (0.030 ml, 0.170 mmol) and 3-(DIETHOXYPHOSPHORYLOXY)-1,2,3-BENZO-TRIAZIN-4(3H)-ONE (20.35 mg, 0.068 mmol) were added. The reaction mixture was diluted with DMF (0.5 ml). Most solids were dissolved. It was stirred at rt for 44 h. It was diluted with EtOAc and washed with water. The organic layer was washed with brine, dried with Na2SO4, and concentrated to a tan oil/gel. Purification by FCC up to 8% MeOH in CH2Cl2 afforded the desired product as a white foam (18 mg, 100%). MS (ESI) [M+H$^+$]=516.27; 1H NMR (400 MHz, CHLOROFORM-d) δ ppm 11.18 (br. s., 1H) 8.45 (dd, J=4.78, 1.26 Hz, 1H) 8.04 (d, J=5.04 Hz, 1H) 7.39 (d, J=6.55 Hz, 1H) 7.23-7.30 (m, 1H) 7.15 (dd, J=7.68, 4.91 Hz, 1H) 6.84-7.08 (m, 4H) 6.73 (d, J=2.52 Hz, 1H) 4.91 (d, J=12.59 Hz, 1H) 4.61 (td, J=12.15, 3.65 Hz, 1 H) 4.34 (d, J=12.84 Hz, 1H) 3.37 (br. s., 1H) 3.02-3.31 (m, 3H) 2.66-2.97 (m, 3 H) 2.05-2.36 (m, 4H) 1.86-2.00 (m, 2H).

Intermediates 56 and 57

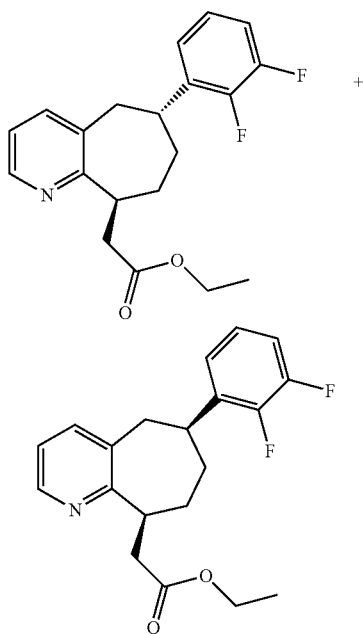

Ethyl 2-((6,9-trans)-6-(2,3-difluorophenyl)-6,7,8,9-tetrahydro-5H-cyclohepta[b]pyridin-9-yl)acetate and ethyl 2-((6,9-cis)-6-(2,3-difluorophenyl)-6,7,8,9-tetrahydro-5H-cyclohepta[b]pyridin-9-yl)acetate. In a 50 mL round-bottomed flask was (E)-ethyl 2-(6-(2,3-difluorophenyl)-7,8-dihydro-5H-cyclohepta[b]pyridin-9(6H)-ylidene)acetate (113.6 mg, 0.331 mmol) in MeOH (6 mL) to give a colorless solution. Pd/C (35.2 mg, 0.033 mmol) was added. The mixture was stirred under hydrogen balloon for 4 h. It was filtered, washed and concentrated. FCC up to 50% EtOAc/hexane afforded the two desired products, both as colorless oil. 1H NMR and 13C NMR of both 1 (50.0 mg, 40.5%) and 2 (66.7 mg, 54%) were obtained and confirmed the structure. The less polar one (1) is most likely the trans isomer as compared with the carbamate analogs (the ratio of trans/cis is 1/1.33). MS (ESI)[M+H⁺]=346.25 (tR=2.20 and 2.42 min on XBridge 4.6×50 mm S5 column with 4 min run). Trans product: 1H NMR (400 MHz, CHLOROFORM-d) δ ppm 8.32 (dd, J=4.78, 1.51 Hz, 1H) 7.36 (dd, J=7.43, 1.64 Hz, 1H) 6.93-7.09 (m, 4H) 4.06-4.23 (m, 2H) 3.68 (ddd, J=10.20, 7.68, 7.55 Hz, 1H) 3.32-3.47 (m, 1H) 3.22 (dd, J=16.24, 7.93 Hz, 1H) 2.85-3.00 (m, 1H) 2.74 (d, J=14.10 Hz, 1H) 2.59 (dd, J=16.12, 7.05 Hz, 1H) 2.04-2.17 (m, 2H) 1.91 (dt, J=13.85, 3.40 Hz, 1 H) 1.43-1.61 (m, 1H) 1.17-1.28 (m, 3H); 13C NMR (100 MHz, CHLOROFORM-d) δ ppm 173.58, 162.50, 152.01-149.41 (dd, J=13.3 and 246 Hz), 149.41-146.73 (dd, J=24.0 and 244 Hz), 146.28, 136.95, 136.86, 135.45, 124.15, 122.10, 121.41, 114.88 (d, J=17.0 Hz), 60.13, 41.59, 40.78, 38.58, 38.38, 37.76, 32.90, 14.27. Cis product: 1H NMR (400 MHz, CHLOROFORM-d) δ ppm 8.35 (dd, J=4.91, 1.64 Hz, 1H) 7.29 (dd, J=7.30, 1.51 Hz, 1H) 7.02 (dd, J=7.55, 4.78 Hz, 1H) 6.89-6.97 (m, 2H) 6.79-6.89 (m, 1H) 4.03-4.16 (m, 2H) 3.77 (dt, J=7.62, 3.87 Hz, 1H) 3.26 (br. s., 1H) 3.10 (d, J=6.04 Hz, 2H) 2.99 (dd, J=15.23, 7.43 Hz, 1H) 2.76 (dd, J=15.23, 8.18 Hz, 1H) 1.77-2.07 (m, 4H) 1.14-1.25 (m, 3H); 13C NMR (100 MHz, CHLOROFORM-d) δ ppm 172.62, 161.47, 152.00-149.40 (dd, J=13.7 and 247 Hz), 149.53-146.75 (dd, J=20.2 and 245 Hz), 146.90, 137.97, 136.72 (d, J=11.4 Hz), 133.82, 123.96, 122.41, 121.71, 114.82 (d, J=17.1 Hz), 60.34, 39.41, 36.84, 36.70, 35.68, 31.42, 29.64, 14.21.

Intermediate 58

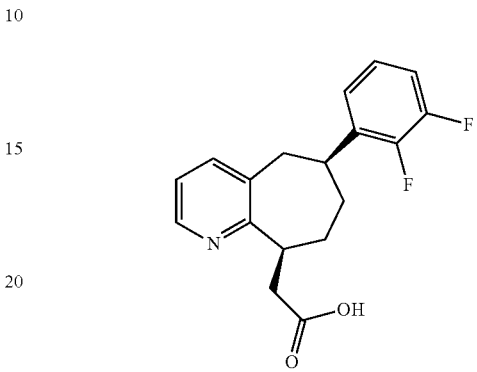

2-((6,9-Cis)-6-(2,3-difluorophenyl)-6,7,8,9-tetrahydro-5H-cyclohepta[b]pyridin-9-yl)acetic acid. In a 50 mL round-bottomed flask was ethyl 2-((6,9-cis)-6-(2,3-difluorophenyl)-6,7,8,9-tetrahydro-5H-cyclohepta[b]pyridin-9-yl) acetate (66.7 mg, 0.193 mmol) in THF (2 ml) to give a colorless solution. LiOH (0.4 ml, 0.400 mmol) was added and the mixture was stirred at rt overnight. 16 h: LCMS indicated good conversion with likely SM. 1 ml MeOH was added and the mixture was stirred for another 24 h. LCMS indicated complete conversion. Concentrated and further dried under a high vac to remove water to a white solid. It was further dried by azeotroping with dry benzene and under high vacuum for 4 h. The white solid was then directly subject to next reaction. MS (ESI)[M+H⁺]=318.22.

Example 5

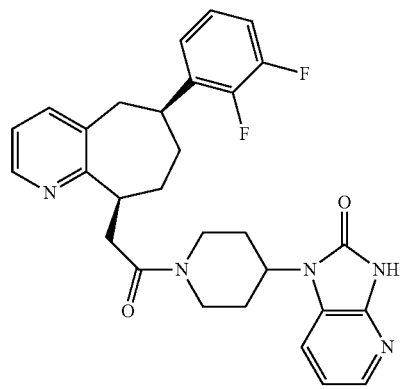

1-(1-(2-((6,9-Cis)-6-(2,3-difluorophenyl)-6,7,8,9-tetrahydro-5H-cyclohepta[b]pyridin-9-yl)acetyl)piperidin-4-yl)-1H-imidazo[4,5-b]pyridin-2(3H)-one. In a 100 mL round-bottomed flask was 2-((6,9-cis)-6-(2,3-difluorophenyl)-6,7,8,9-tetrahydro-5H-cyclohepta[b]pyridin-9-yl)acetic acid (61.2 mg, 0.193 mmol) and 1-(piperidin-4-yl)-1H-imidazo[4,5-b]pyridin-2(3H)-one (126 mg, 0.579 mmol) (bis-HCl salt) in CH2Cl2 (4 ml) to give a colorless suspension. Hunig's Base (0.169 ml, 0.965 mmol) and 3-(DIETHOXYPHOSPHORYLOXY)-1,2,3-BENZO-TRIAZIN-4(3H)-ONE (115 mg, 0.386 mmol) were added. The reaction mixture was diluted with DMF (1 ml). Most solids were dissolved. It was stirred at r.t. overnight. 20 h: LCMS showed no sm and product plus a less polar peak. 44 h: The less polar peak decreased. It was diluted with EtOAc and washed with water. The layers were separated. The organic layer was washed with brine, dried with Na2SO4, and concentrated to a tan oil. Purification by FCC (ISCO) up to 8% MeOH in CH2Cl2 afforded the desired product as a tan foam (91 mg, 87% for 2 steps). LCMS: >95%. 1H NMR confirmed the structure. MS (ESI)[M+H$^+$]=518.34; 1H NMR (400 MHz, CHLOROFORM-d) δ ppm 11.57 (br. s., 1H) 8.36 (br. s., 1H) 8.04 (d, J=4.78 Hz, 1H) 7.26-7.39 (m, 1H) 7.17-7.27 (m, 1H) 6.69-7.07 (m, 5 H) 4.81 (t, J=15.36 Hz, 1H) 4.61 (td, J=12.21, 4.03 Hz, 1H) 4.16-4.39 (m, 1H) 3.77-4.00 (m, 1H) 3.07-3.49 (m, 4H) 2.53-3.04 (m, 3H) 1.65-2.47 (m, 8H).

Intermediate 59

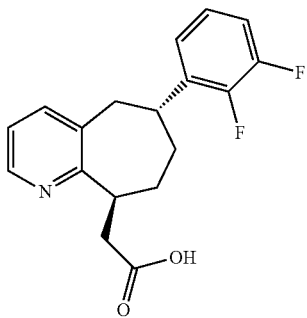

2-((6,9-Trans)-6-(2,3-difluorophenyl)-6,7,8,9-tetrahydro-5H-cyclohepta[b]pyridin-9-yl)acetic acid. In a 50 mL round-bottomed flask was ethyl 2-((6,9-trans)-6-(2,3-difluorophenyl)-6,7,8,9-tetrahydro-5H-cyclohepta[b]pyridin-9-yl)acetate (50.0 mg, 0.145 mmol) in THF (2 ml) to give a colorless solution. LiOH (0.4 ml, 0.400 mmol) was added and the mixture was stirred at rt overnight. 16 h: LCMS indicated a little sm left. 1 ml MeOH was added and the mixture was stirred for another 24 h. LCMS indicated complete conversion. The mixture was concentrated and further dried under a high vacuum to remove water to a white solid. It was further dried by azeotroping with dry benzene and under high vacuum for 4 h. The white solid was then directly subject to next reaction. MS (ESI)[M+H$^+$]=318.22.

Examples 6 and 7

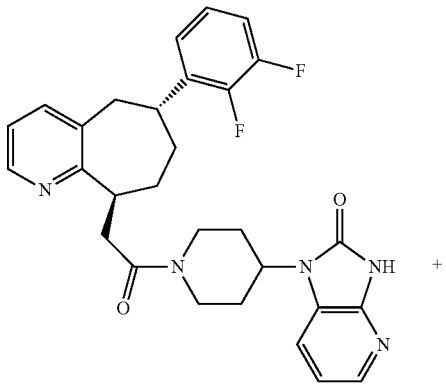

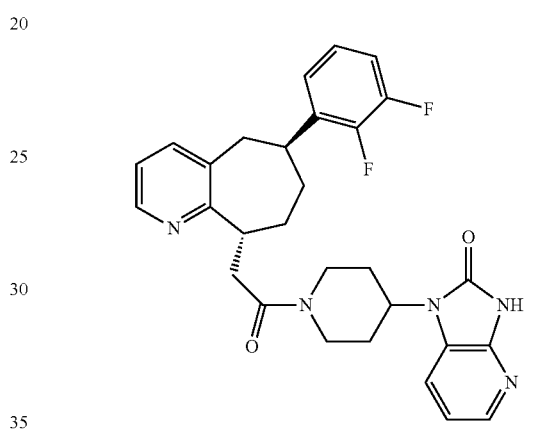

1-(1-(2-((6R,9S)-6-(2,3-Difluorophenyl)-6,7,8,9-tetrahydro-5H-cyclohepta[b]pyridin-9-yl)acetyl)piperidin-4-yl)-1H-imidazo[4,5-b]pyridin-2(3H)-one and 1-(1-(2-((6S,9R)-6-(2,3-difluorophenyl)-6,7,8,9-tetrahydro-5H-cyclohepta[b]pyridin-9-yl)acetyl)piperidin-4-yl)-1H-imidazo[4,5-b]pyridin-2(3H)-one. In a 100 mL round-bottomed flask was 2-((6,9-trans)-6-(2,3-difluorophenyl)-6,7,8,9-tetrahydro-5H-cyclohepta[b]pyridin-9-yl)acetic acid (46.0 mg, 0.145 mmol) and 1-(piperidin-4-yl)-1H-imidazo[4,5-b]pyridin-2(3H)-one (95 mg, 0.435 mmol) (bis-HCl salt) in CH2Cl2 (4 ml) to give a colorless suspension. Hunig's Base (0.127 ml, 0.725 mmol) and 3-(DIETHOXYPHOSPHORYLOXY)-1,2,3-BENZO-TRIAZIN-4(3H)-ONE (87 mg, 0.290 mmol) were added. The reaction mixture was diluted with DMF (1 ml). Most solids were dissolved. It was stirred at rt overnight. 44 h: LCMS indicated complete conversion. It was diluted with EtOAc and washed with water. The layers were separated. The organic layer was washed with brine, dried with Na2SO4, and concentrated to a tan oil/gel. Purification by FCC (ISCO) up to 8% MeOH in CH2Cl2 afforded the desired product as a tan foam (68 mg, 86% for 2 steps). MS (ESI) [M+H$^+$]=518.27; 1H NMR (400 MHz, CHLOROFORM-d) δ ppm 11.44 (br. s., 1H) 8.25-8.42 (m, 1H) 8.05 (d, J=5.29 Hz, 1H) 7.38 (t, J=8.44 Hz, 1H) 7.20-7.31 (m, 1H) 6.83-7.10 (m, 5H) 4.87 (d, J=12.34 Hz, 1H) 4.53-4.73 (m, 1H) 4.43 (t, J=15.36 Hz, 1H) 3.81-4.00 (m, 1H) 3.36-3.60 (m, 2H) 3.24 (t, J=12.97 Hz, 1H) 2.94 (t, J=11.21 Hz, 1H) 2.33-2.80 (m, 4H) 2.05-2.31 (m, 3H) 1.80-2.05 (m, 3H) 1.38-1.63 (m, 1H). The racemic product was resolved by chiral HPLC (Chiralpak AD-H analytical column, 4.6×250 mm, 5 µm; Mobile Phase:

40% MeOH in CO2; Temp: 35° C.; Flow rate: 2.0 mL/min. for 26 min; Injection: 5 uL of ~2 mg/mL in MeOH). Compound (6R,9S) was the first peak with tR=13.88 min while compound (6S,9R) was the second peak with tR=19.19 min).

Intermediate 60

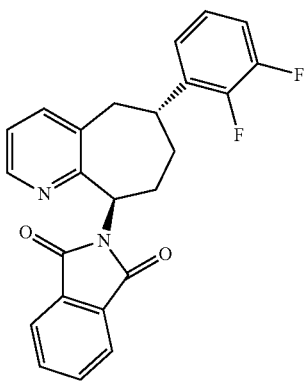

Trans-2-(-6-(2,3-difluorophenyl)-6,7,8,9-tetrahydro-5H-cyclohepta[b]pyridin-9-yl)isoindoline-1,3-dione. In a 500 mL round-bottomed flask was (6,9-cis)-6-(2,3-difluorophenyl)-6,7,8,9-tetrahydro-5H-cyclohepta[b]pyridin-9-ol (1.56 g, 5.67 mmol) (azeotroped with dry benzene) in CH2Cl2 (40 mL) to give a colorless solution. Isoindoline-1,3-dione (1.667 g, 11.33 mmol) and TRIPHENYLPHOSPHINE (2.97 g, 11.33 mmol) were added at 0° C., followed by DIAD (1.653 mL, 8.50 mmol). The mixture was warmed up to rt under nitrogen overnight. 17 h: LCMS showed complete conversion. It was concentrated to dryness. Direct FCC up to 50% EtOAc/hexane afforded two close peaks. The mixed peaks (including the dehydrated side product) were combined and concentrated to afford a white solid, which was directly used in the next step. MS (ESI)[M+H$^+$]=405.23.

Intermediate 61

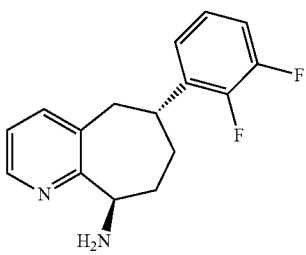

Trans-6-(2,3-difluorophenyl)-6,7,8,9-tetrahydro-5H-cyclohepta[b]pyridin-9-amine. In a 500 mL round-bottomed flask was 2-((6,9-trans)-6-(2,3-difluorophenyl)-6,7,8,9-tetrahydro-5H-cyclohepta[b]pyridin-9-yl)isoindoline-1,3-dione (2.293 g, 5.67 mmol) in MeOH (50 mL) to give a white suspension. HYDRAZINE (5 mL, 159 mmol) (5 ml hydrazine hydrate was used) was added, and the mixture was stirred in a preheated oil bath at 70° C. under nitrogen for 5 h (Solids gradually disappeared, and new solids gradually fall out). LCMS showed complete conversion. The residue was partitioned between 0.5N NaOH and EtOAc. The layers were separated and the aqueous layer was extracted with EtOAc. The combined organic layers were washed with brine, dried, and concentrated. FCC up to 10% MeOH (with 2M ammonia) in CH2Cl2 afforded the desired product as a colorless oil (0.65 g, 42% for two steps, some might have lost during purification), which solidified to a white solid upon standing. MS (ESI)[M+H$^+$]=275.26; 1H NMR (400 MHz, CHLOROFORM-d) δ ppm 8.38 (d, J=4.78 Hz, 1H) 7.30-7.41 (m, 1H) 6.89-7.10 (m, 4H) 4.28 (d, J=10.58 Hz, 1H) 3.13-3.29 (m, 1H) 2.63-3.00 (m, 4 H) 2.02-2.15 (m, 3H) 1.51-1.70 (m, 1H); 13C NMR (100 MHz, CHLOROFORM-d) δ ppm 170.83, 151.85-149.39 (dd, J=13.3 and 246 Hz), 149.29-146.72 (d, J=12.5 and 245 Hz), 146.24, 137.11, 136.62 (d, J=11.6 Hz), 134.30, 124.17, 122.10, 121.78, 114.95 (d, J=17.1 Hz), 55.25, 40.52, 37.57, 37.04, 37.00.

Intermediate 62

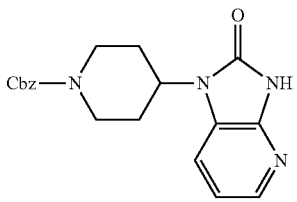

Benzyl 4-(2-oxo-2,3-dihydro-1H-imidazo[4,5-b]pyridin-1-yl)piperidine-1-carboxylate. In an oven-dried 500 mL round-bottomed flask was 1-(piperidin-4-yl)-1H-imidazo[4,5-b]pyridin-2(3H)-one dihydrochloride (2.91 g, 9.99 mmol) in CH2Cl2 (50 mL) to give a tan suspension. Et3N (5.57 mL, 40.0 mmol) was added under nitrogen. BENZYL CHLOROFORMATE (1.421 mL, 9.99 mmol) was added dropwise via syringe. The mixture was stirred at rt overnight (2:00 pm). LCMS showed good conversion (with some sm left). The reaction mixture was diluted with EtOAc and water. The layers were separated. The organic layer was washed with brine, dried and concentrated. The residue was purified by FCC up to 8% MeOH/CH2Cl2 to afford the desired product as a colorless oil (2.17 g, 62%). MS (ESI)[M+H$^+$]=353.30. It was carried on to next step without further characterizations.

Intermediate 63

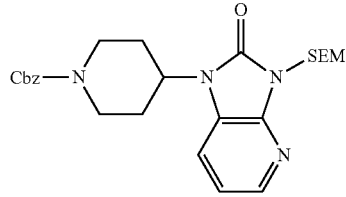

Benzyl 4-(2-oxo-3-((2-(trimethylsilyl)ethoxy)methyl)-2,3-dihydro-1H-imidazo[4,5-b]pyridin-1-yl)piperidine-1-carboxylate. In a 500 mL round-bottomed flask was benzyl 4-(2-oxo-2,3-dihydro-1H-imidazo[4,5-b]pyridin-1-yl)piperidine-1-carboxylate (1.62 g, 4.60 mmol) in THF (40 mL) to give a colorless solution. NaH (0.552 g, 22.99 mmol) (excess) was added. After stirring for 5 min under nitrogen, SEM-Cl (0.897 mL, 5.06 mmol) was added. The mixture was stirred at rt overnight. 16 h: LCMS showed good conversion. The reaction mixture was diluted with EtOAc and slowly quenched with water (gas evolves!). The layers were separated. The organic layer was washed with brine, dried and concentrated to a slightly green oil. TLC (10% MeOH/CH2Cl2) showed a major blue spot (Rf ~0.25) (slightly less polar than SM). Purification by FCC up to 10% MeOH/CH2Cl2 afforded the desired product as a colorless oil (1.92 g, 87%). MS (ESI) [M+H$^+$]=483.33; 1H NMR (400 MHz, CHLOROFORM-d) δ ppm 7.25-7.40 (m, 6H) 6.82-6.94 (m, 1H) 6.60 (t, J=7.05 Hz, 1H) 5.66 (s, 2H) 5.11 (s, 2H) 4.45-4.63 (m, 1H) 4.33 (br. s., 2H) 3.55-3.69 (m, 2H) 2.88 (d, J=1.01 Hz, 2H) 2.06 (d, J=9.06 Hz, 2 H) 1.80 (d, J=11.58 Hz, 2H) 0.82-1.00 (m, 2H) −0.13-−0.03 (m, 9H).

Intermediate 64

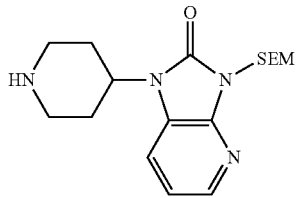

1-(Piperidin-4-yl)-3-((2-(trimethylsilyl)ethoxy)methyl)-1H-imidazo[4,5-b]pyridin-2(3H)-one. In a 500 mL round-bottomed flask was benzyl 4-(2-oxo-3-((2-(trimethylsilyl)ethoxy)methyl)-2,3-dihydro-1H-imidazo[4,5-b]pyridin-1-yl)piperidine-1-carboxylate (1.85 g, 3.83 mmol) in MeOH (30 mL) to give a colorless solution. Pd/C (0.408 g, 0.383 mmol) was added, and the mixture was stirred under hydrogen balloon overnight. 17 h: LCMS indicated complete conversion. It was filtered, washed, and concentrated under high vacuum to a colorless foam (1.31 g, 100%). MS (ESI)[M+H$^+$]=349.29; 1H NMR (400 MHz, CHLOROFORM-d) δ ppm 9.55 (br., 1H) 7.64-8.06 (m, 1H) 7.42 (br. s., 1H) 6.81 (br. s., 1H) 5.66 (br. s., 2 H) 4.73 (d, J=13.85 Hz, 1H) 3.42-3.89 (m, 4H) 3.08-3.42 (m, 2H) 2.88 (br. s., 2 H) 1.72-2.16 (m, 2H) 0.76-0.94 (m, 2H) −0.22-−0.08 (m, 9H).

Intermediate 65

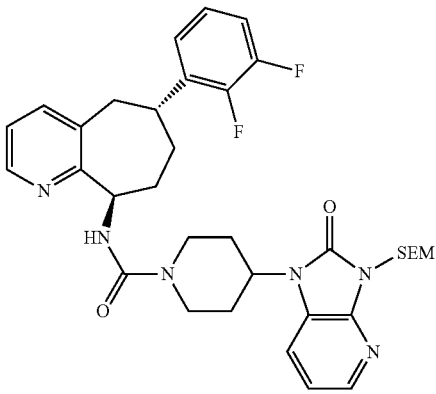

N-((6,9-trans)-6-(2,3-difluorophenyl)-6,7,8,9-tetrahydro-5H-cyclohepta[b]pyridin-9-yl)-4-(2-oxo-3-((2-(trimethylsilyl)ethoxy)methyl)-2,3-dihydro-1H-imidazo[4,5-b]pyridin-1-yl)piperidine-1-carboxamide. In an oven-dried 100 ml round-bottomed flask was 1-(piperidin-4-yl)-3-((2-(trimethylsilyl)ethoxy)methyl)-1H-imidazo[4,5-b]pyridin-2(3H)-one (262 mg, 0.752 mmol) in CH2Cl2 (8 mL) to give a colorless solution. Et3N (0.192 mL, 1.379 mmol) was added under nitrogen and the mixture was cooled to −20° C. Trichloromethyl chloroformate (0.061 mL, 0.502 mmol) was added dropwise. The mixture was gradually warmed up with stirring to 10° C. for 1 h, during which time the solution became slightly yellow. TLC (10% MeOH/CH2Cl2) showed a major less polar bright blue spot with no sm at the baseline. It was concentrated to dryness (white solids) under house vacuum and further dried under high vacuum. (6,9-trans)-6-(2,3-difluorophenyl)-6,7,8,9-tetrahydro-5H-cyclohepta[b]pyridin-9-amine (172 mg, 0.627 mmol) and Et3N (0.192 mL, 1.379 mmol) dissolved in 1 ml THF (plus 2 ml rinse) was added via canuula at rt. Another Et3N (0.192 mL, 1.379 mmol) was added. The resulted faint yellow suspension was stirred under nitrogen overnight. 16 h: LCMS showed complete conversion. It was diluted with water and EtOAc. The layers were separated. The organic layer was washed with brine, dried with Na2SO4, and concentrated. Purification by FCC up to 10% MeOH/CH2Cl2) afforded the desired product (465 mg, 93%). MS (ESI)[M+H$^+$]=649.34; 1H NMR (500 MHz, CHLOROFORM-d) δ ppm 8.36 (d, J=4.88 Hz, 1H) 7.96-8.09 (m, 1H) 7.55 (d, J=4.27 Hz, 1H) 7.46 (d, J=7.63 Hz, 1H) 7.29 (d, J=7.93 Hz, 1H) 7.13 (t, J=6.10 Hz, 1H) 6.97-7.09 (m, 3H) 6.93 (dd, J=7.32, 5.49 Hz, 1H) 5.39 (s, 2H) 5.11 (dd, J=10.38, 3.66 Hz, 1H) 4.53-4.66 (m, 1H) 4.33 (t, J=11.29 Hz, 2H) 3.70 (t, J=8.24 Hz, 2H) 3.25-3.44 (m, 1H) 2.84-3.05 (m, 3H) 2.77 (d, J=14.04 Hz, 1H) 2.19-2.50 (m, 4H) 2.11 (d, J=14.04 Hz, 1H) 1.91 (d, J=11.29 Hz, 2H) 1.53 (t, J=12.05 Hz, 1H) 0.95 (t, J=8.24 Hz, 2H) −0.06 (s, 9H).

Examples 8 and 9

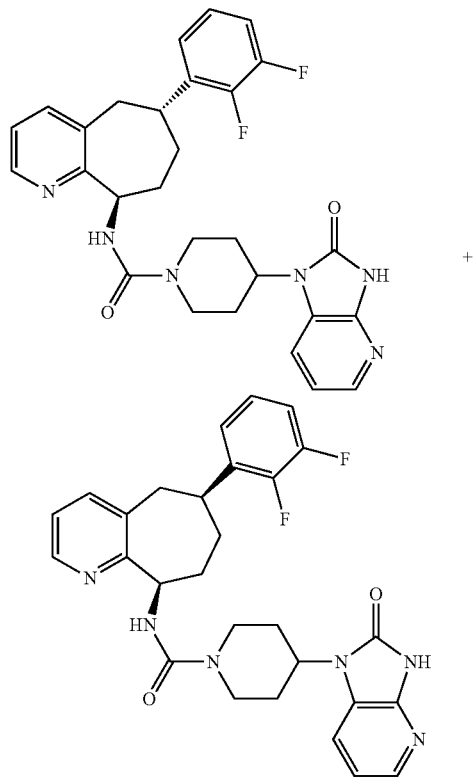

N-((6R,9R)-6-(2,3-difluorophenyl)-6,7,8,9-tetrahydro-5H-cyclohepta[b]pyridin-9-yl)-4-(2-oxo-2,3-dihydro-1H-imidazo[4,5-b]pyridin-1-yl)piperidine-1-carboxamide and N-((6S,9S)-6-(2,3-difluorophenyl)-6,7,8,9-tetrahydro-5H-cyclohepta[b]pyridin-9-yl)-4-(2-oxo-2,3-dihydro-1H-imidazo[4,5-b]pyridin-1-yl)piperidine-1-carboxamide. In a 250 mL round-bottomed flask was N-((6,9-trans)-6-(2,3-difluorophenyl)-6,7,8,9-tetrahydro-5H-cyclohepta[b]pyridin-9-yl)-4-(2-oxo-3-((2-(trimethylsilyl)ethoxy)methyl)-2,3-dihydro-1H-imidazo[4,5-b]pyridin-1-yl)piperidine-1-carboxamide (racemate) (200 mg, 0.308 mmol) in CH2Cl2 (4 mL) to give a tan solution. TFA (1.000 mL) was added, and the mixture was stirred at rt for 1 h. LCMS indicated complete conversion. Volatiles were stripped off. The residue was partitioned between 0.5N NaOH and EtOAc. The layers were separated and the aqueous layer was extracted with EtOAc (LCMS indicated no product in the aqueous layer). The combined organic layers were washed with brine, dried, and concentrated to a tan foam. Purification by FCC up to 10% MeOH/CH2Cl2 afforded the desired racemic product (118 mg, 74%) as a colorless foam/solid. LCMS indicated >95% impurity. MS (ESI)[M+H⁺]=519.24. 1H NMR (400 MHz, CHLOROFORM-d) δ ppm 11.78 (br. s., 1H) 8.23-8.41 (m, 1 H) 7.98 (d, J=4.28 Hz, 1H) 7.56 (d, J=4.28 Hz, 1H) 7.34-7.47 (m, 1H) 7.19-7.33 (m, 1H) 7.07 (dd, J=7.43, 4.91 Hz, 1H) 6.90-7.02 (m, 3H) 6.87 (dd, J=7.81, 5.29 Hz, 1H) 5.12 (dd, J=10.45, 3.90 Hz, 1H) 4.46-4.64 (m, 1H) 4.19-4.42 (m, 2H) 3.28 (t, J=12.59 Hz, 1H) 2.88-3.05 (m, 2H) 2.77-2.86 (m, 1H) 2.71 (d, J=13.85 Hz, 1H) 2.41 (d, J=13.35 Hz, 1H) 2.14-2.34 (m, 3H) 2.04 (d, J=12.09 Hz, 1H) 1.86 (d, J=10.32 Hz, 2H) 1.37-1.58 (m, 1H). The racemic product was resolved by chiral HPLC (Chiralpak AD-H analytical column, 4.6×250 mm, 5 μm; Mobile Phase: 40% MeOH in CO2; Temp: 35° C.; Flow rate: 2.0 mL/min. for 32 min; UV monitored @ 292 nm; Injection: 5 uL of ~2 mg/mL in MeOH). Compound (6R,9R) was the first peak with tR=15.26 min while compound (6S, 9S) was the second peak with tR=24.98 min).

Intermediate 66

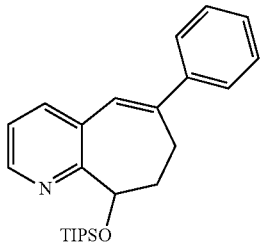

(E)-6-Phenyl-9-(triisopropylsilyloxy)-8,9-dihydro-7H-cyclohepta[b]pyridine. The mixture of phenylboronic acid (0.060 g, 0.495 mmol), sodium carbonate (0.382 mL, 0.764 mmol), (E)-9-(triisopropylsilyloxy)-8,9-dihydro-7H-cyclohepta[b]pyridin-6-yl trifluoromethanesulfonate (0.1922 g, 0.413 mmol) and tetrakis(triphenylphosphine)palladium(0) (0.024 g, 0.021 mmol) in Toluene (5 mL) and MeOH (1 mL) was heat to 80° C. under N2 for 3 hours. LCMS showed no more starting material. The reaction was diluted with ethyl acetate and washed with water one time. The ethyl acetate layer was separated, dried (Na2SO4), filtered and concentrated to give the crude product. The crude was used as it is. MS (ESI)[M+H⁺]=394.32.

Intermediate 67

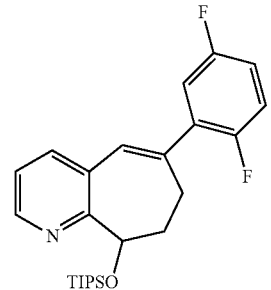

(E)-6-(2,5-Difluorophenyl)-9-(triisopropylsilyloxy)-8,9-dihydro-7H-cyclohepta[b]pyridine. The mixture of 2,5-difluorophenylboronic acid (0.088 g, 0.554 mmol), sodium carbonate (0.427 mL, 0.854 mmol), [Reactants] and tetrakis(triphenylphosphine)palladium(0) (0.027 g, 0.023 mmol) in Toluene (5 mL) and MeOH (1 mL) was heat to 80° C. under N2 for 3 hours. LCMS showed no more starting material. The reaction was diluted with ethyl acetate and washed with water one time. The ethyl acetate layer was separated, dried (Na2SO4), filtered and concentrated to give the crude product. The crude was used as it is. MS (ESI)[M+H⁺]=430.29.

Intermediate 68

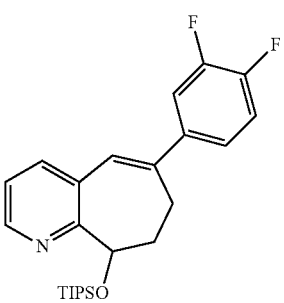

(E)-6-(3,4-Difluorophenyl)-9-(triisopropylsilyloxy)-8,9-dihydro-7H-cyclohepta[b]pyridine. The mixture of 3,4-difluorophenylboronic acid (0.083 g, 0.527 mmol), sodium carbonate (0.406 mL, 0.813 mmol), (E)-9-(triisopropylsilyloxy)-8,9-dihydro-7H-cyclohepta[b]pyridin-6-yl trifluoromethanesulfonate (0.2045 g, 0.439 mmol) and tetrakis(triphenylphosphine)palladium(0) (0.025 g, 0.022 mmol) in Toluene (5 mL) and MeOH (1 mL) was heat to 80° C. under N2 for 3 hours. LCMS showed no more starting material. The reaction was diluted with ethyl acetate and washed with water one time. The ethyl acetate layer was separated, dried (Na2SO4), filtered and concentrated to give the crude product. The Crude was used as it is. MS (ESI)[M+H+]=430.36.

Intermediate 69

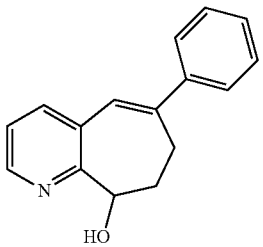

(E)-6-phenyl-8,9-dihydro-7H-cyclohepta[b]pyridin-9-ol. TBAF (1.041 mL, 1.041 mmol) was added to the THF (5 mL) solution of (E)-6-phenyl-9-(triisopropylsilyloxy)-8,9-dihydro-7H-cyclohepta[b]pyridine (0.2049 g, 0.521 mmol) at rt. The reaction was stirred at room temperature for 6 hours. The solvent was removed via vacuum to give the crude product. MS (ESI)[M+H+]=238.25.

Intermediate 70

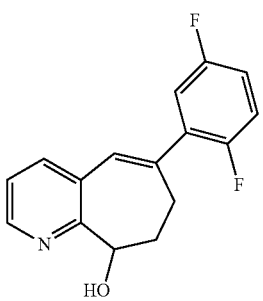

(E)-6-(2,5-Difluorophenyl)-8,9-dihydro-7H-cyclohepta[b]pyridin-9-ol. TBAF (0.954 mL, 0.954 mmol) was added to the THF (5 mL) solution of (E)-6-(2,5-difluorophenyl)-9-(triisopropylsilyloxy)-8,9-dihydro-7H-cyclohepta[b]pyridine (0.2049 g, 0.477 mmol) at rt. The reaction was stirred at room temperature for 6 hours. The solvent was removed via vacuum and the product was purified by flash column eluted with ethyl acetate in hexane from 0 to 50% to 100% (102.2 mg, 78%). MS (ESI)[M+H+]=274.23 1H NMR (400 MHz, CHLOROFORM-d) δ ppm 8.37 (dd, J=4.78, 1.26 Hz, 1H) 7.51 (dd, J=7.81, 1.26 Hz, 1H) 7.17-7.27 (m, 1H) 6.87-7.05 (m, 3H) 6.44 (s, 1H) 5.74 (br. s., 1H) 4.77 (dd, J=10.45, 2.64 Hz, 1H) 2.79-2.93 (m, 1H) 2.66-2.77 (m, 1H) 2.48-2.60 (m, J=13.53, 5.45, 5.45, 2.77 Hz, 1H) 1.97-2.11 (m, 1H).

Intermediate 71

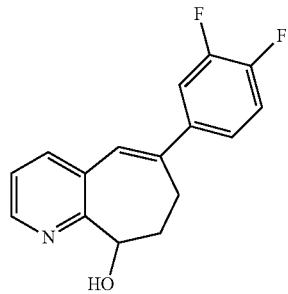

(E)-6-(3,4-Difluorophenyl)-8,9-dihydro-7H-cyclohepta[b]pyridin-9-ol. TBAF (0.878 mL, 0.878 mmol) was added to the THF (5 mL) solution of (E)-6-(3,4-difluorophenyl)-9-(triisopropylsilyloxy)-8,9-dihydro-7H-cyclohepta[b]pyridine (0.189 g, 0.439 mmol) at rt. The reaction was stirred at room temperature for 6 hours. The solvent was removed via vacuum and the product was purified by flash column eluted with ethyl acetate in hexane from 0 to 50% to 100% (93.5 mg, 78%). MS (ESI)[M+H+]=274.23.

General Reduction Procedure: The substrates (from TBAF de-protection) with Pd/C (10% activate carbon) (5% mol) in MeOH (5 mL) was hydrogenated with a H2 balloon overnight at room temperature. The reaction was filtered through celite plug and washed with ethyl acetate. The filtrate was concentrated and the product was purified via flash column eluted with ethyl acetate in hexane from 0 to 50%, to 100%. Trans products was eluted out first as a minor while cis products were much more polar as major products.

Intermediate 72

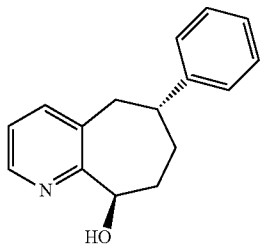

(6,9-trans)-6-phenyl-6,7,8,9-tetrahydro-5H-cyclohepta[b]pyridin-9-ol. From 0.224 mmol starting material, 15 mg product was obtained. Combined with the cis isomer the yield was 98%. MS (ESI)[M+H$^+$]=240.32.

Intermediate 73

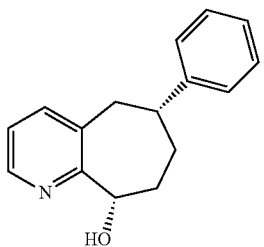

(6,9-Cis)-6-Phenyl-6,7,8,9-tetrahydro-5H-cyclohepta[b]pyridin-9-ol. From 0.224 mmol starting material, 38 mg product was obtained. Combined with trans isomer the yield was 98%. MS (ESI)[M+H$^+$]=240.32.

Intermediate 74

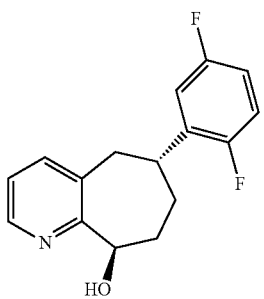

(6,9-trans)-6-(2,5-Difluorophenyl)-6,7,8,9-tetrahydro-5H-cyclohepta[b]pyridin-9-ol. From 0.374 mmol starting material, 19.3 mg product was obtained (trans, less-polar spot, Rf ~0.7, 25% ethyl acetate in hexane). Combined with cis isomer the yield was 90%. 1H NMR (400 MHz, CHLOROFORM-d) δ ppm 8.36-8.45 (m, 1H) 7.46 (dd, J=7.55, 1.26 Hz, 1H) 7.16 (dd, J=7.43, 4.91 Hz, 1H) 6.94-7.04 (m, 2H) 6.83-6.92 (m, 1H) 4.87 (dd, J=11.33, 2.01 Hz, 1H) 3.05-3.19 (m, 1H) 2.74-2.89 (m, 2H) 2.25-2.35 (m, 1H) 2.06-2.17 (m, 2H) 1.56-1.68 (m, 2H).

Intermediate 75

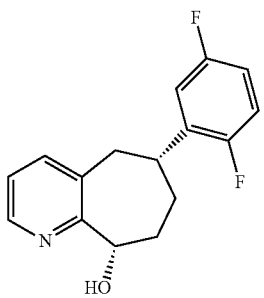

(6,9-Cis)-6-(2,5-Difluorophenyl)-6,7,8,9-tetrahydro-5H-cyclohepta[b]pyridin-9-ol. From 0.374 mmol starting material, 92.4 mg product was obtained (cis, more polar peak, Rf ~0.5, 50% ethyl acetate in hexane). Combined with trans isomer the yield was 90%. 1H NMR (400 MHz, CHLOROFORM-d) δ ppm 8.18-8.33 (m, 1H) 7.22-7.35 (m, 1H) 7.03 (dd, J=7.55, 5.04 Hz, 1H) 6.93 (td, J=9.25, 4.66 Hz, 1H) 6.70-6.87 (m, 2H) 4.92-5.07 (m, 1H) 3.34-3.45 (m, 1H) 3.29 (t, J=8.44 Hz, 1H) 2.89 (dd, J=14.10, 2.27 Hz, 1 H) 2.14-2.30 (m, 1H) 1.91-2.11 (m, 3H).

Intermediate 76

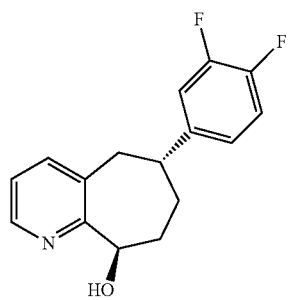

(6,9-Trans)-6-(3,4-Difluorophenyl)-6,7,8,9-tetrahydro-5H-cyclohepta[b]pyridin-9-ol. From 0.342 mmol starting material, 15 mg product was obtained. Combined with cis isomer the yield was 86%. MS (ESI)[M+H$^+$]=276.23; 1H NMR (400 MHz, CHLOROFORM-d) δ ppm 8.30-8.48 (m, 1H) 7.41-7.49 (m, 1H) 6.88-7.18 (m, 4H) 5.93 (br, s, 1H) 4.85 (dd, J=11.21, 2.14 Hz, 1H) 3.10 (dd, J=14.10, 11.58 Hz, 1H) 2.71-2.85 (m, 1H) 2.47-2.57 (m, 1H) 2.27-2.36 (m, 1 H) 1.97-2.18 (m, 2H) 1.47-1.68 (m, 1H).

Intermediate 77

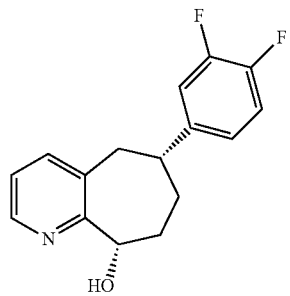

(6,9-cis)-6-(3,4-Difluorophenyl)-6,7,8,9-tetrahydro-5H-cyclohepta[b]pyridin-9-ol. From 0.342 mmol starting material, 66.4 mg product was obtained. Combined with trans isomer the yield was 86%. MS (ESI)[M+H$^+$]=276.23; 1H NMR (400 MHz, CHLOROFORM-d) δ ppm 8.33 (dd, J=5.04, 1.51 Hz, 1 H) 7.23-7.31 (m, 1H) 7.07 (dd, J=7.43, 4.91 Hz, 1H) 6.93-6.99 (m, 1H) 6.80-6.85 (m, 1H) 6.75 (dd, J=4.15, 2.14 Hz, 1H) 5.27 (br. s., 1H) 4.95 (dd, J=9.19, 2.64 Hz, 1H) 3.15-3.33 (m, 1H) 3.00-3.13 (m, 2H) 2.01-2.25 (m, 3H) 1.83-1.97 (m, 1H).

Example 10

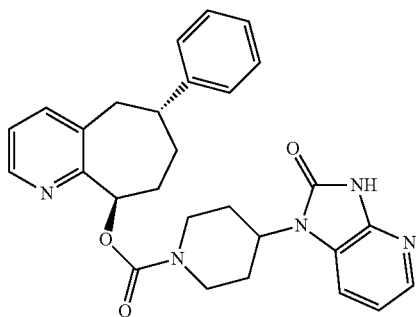

(6,9-Trans)-6-Phenyl-6,7,8,9-tetrahydro-5H-cyclohepta[b]pyridin-9-yl 4-(2-oxo-2,3-dihydro-1H-imidazo[4,5-b]pyridin-1-yl)piperidine-1-carboxylate. NaH (0.025 g, 1.003 mmol) was added to the THF (5 mL) suspension of 4-nitrophenyl 4-(2-oxo-2,3-dihydro-1H-imidazo[4,5-b]pyridin-1-yl)piperidine-1-carboxylate compound with triethylamine (1:3) trihydrochloride (0.080 g, 0.100 mmol) and (6R,9R)-6-phenyl-6,7,8,9-tetrahydro-5H-cyclohepta[b]pyridin-9-ol (0.016 g, 0.067 mmol) at rt. The reaction was stirred for 4 hours at room temperature. The reaction was quenched by adding water. The reaction was further partitioned between ethyl acetate and water. The ethyl acetate layer was separated and washed twice by water before dried (Na2SO4), filtered and concentrated. Flash column was performed (eluted with methanol in CH2Cl2 from 0 to 5% to 10%) (31.1 mg, 87%). MS (ESI)[M+H$^+$]=484.20; 1H NMR (500 MHz, CHLOROFORM-d) δ ppm 8.45 (d, J=4.58 Hz, 1H) 8.08 (d, J=5.19 Hz, 1H) 7.40 (d, J=7.32 Hz, 2H) 7.33 (t, J=7.78 Hz, 2H) 7.23 (d, J=7.93 Hz, 3H) 7.12 (br. s., 1H) 6.93-7.00 (m, 1H) 6.05 (d, J=10.99 Hz, 1H) 4.64 (br. s., 3H) 3.33 (dd, J=13.89, 11.75 Hz, 1H) 3.05 (br. s., 2 H) 2.88 (d, J=14.34 Hz, 1H) 2.61 (td, J=11.06, 3.20 Hz, 1H) 1.79-2.35 (m, 9H).

Example 11

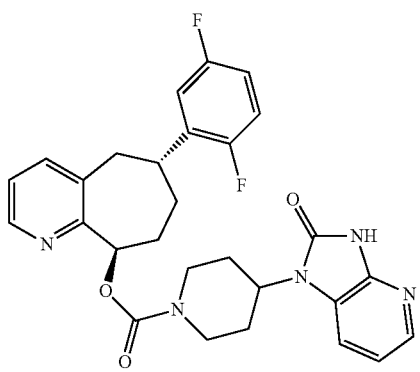

(6,9-trans)-6-(2,5-Difluorophenyl)-6,7,8,9-tetrahydro-5H-cyclohepta[b]pyridin-9-yl 4-(2-oxo-2,3-dihydro-1H-imidazo[4,5-b]pyridin-1-yl)piperidine-1-carboxylate. NaH (0.036 g, 1.417 mmol) was added to the THF (5 mL) suspension of 4-nitrophenyl 4-(2-oxo-2,3-dihydro-1H-imidazo[4,5-b]pyridin-1-yl)piperidine-1-carboxylate compound with triethylamine (1:3) trihydrochloride (0.113 g, 0.142 mmol) and (6R,9R)-6-(2,5-difluorophenyl)-6,7,8,9-tetrahydro-5H-cyclohepta[b]pyridin-9-ol compound with (6S,9S)-6-(2,5-difluorophenyl)-6,7,8,9-tetrahydro-5H-cyclohepta[b]pyridin-9-ol (1:1) (0.052 g, 0.094 mmol) at rt. The reaction was stirred for 4 hours at room temperature. The reaction was quenched by adding water. The reaction was further partitioned between ethyl acetate and water. The ethyl acetate layer was separated and washed twice by water before dried (Na2SO4), filtered and concentrated. Flash column was performed (eluted with methanol in CH2Cl2 from 0 to 5% to 10%) to give the desired product (32.2 mg, 63%). MS (ESI)[M+H$^+$]= 520.25; 1H NMR (400 MHz, CHLOROFORM-d) δ ppm 10.77 (br. s., 1H) 8.45 (d, J=4.03 Hz, 1H) 8.07 (d, J=4.78 Hz, 1H) 7.42 (d, J=6.80 Hz, 2H) 7.13 (br. s., 1H) 6.93-7.05 (m, 3H) 6.84-6.92 (m, 1H) 6.02 (d, J=10.83 Hz, 1H) 4.34-4.81 (m, 3H) 3.30 (t, J=12.59 Hz, 1H) 2.87-3.19 (m, 3H) 2.81 (d, J=14.35 Hz, 1H) 2.63 (br. s., 1H) 2.23-2.39 (m, 2H) 2.12-2.22 (m, 2H) 1.90 (br. s., 3H); 19F NMR (376 MHz, CHLOROFORM-d) δ ppm −118.29 (d, J=17.24 Hz, 1F)-124.51 (d, J=17.24 Hz, 1F).

Example 12

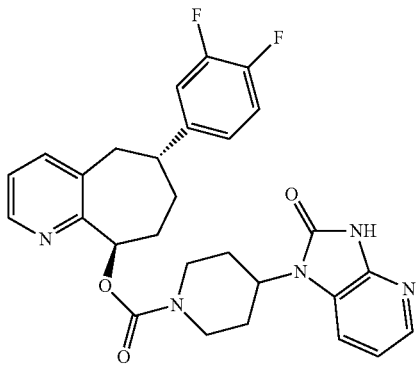

(6,9-Trans)-6-(3,4-Difluorophenyl)-6,7,8,9-tetrahydro-5H-cyclohepta[b]pyridin-9-yl 4-(2-oxo-2,3-dihydro-1H-imidazo[4,5-b]pyridin-1-yl)piperidine-1-carboxylate. NaH (0.056 g, 2.231 mmol) was added to the THF (5 mL) suspension of 4-nitrophenyl 4-(2-oxo-2,3-dihydro-1H-imidazo[4,5-b]pyridin-1-yl)piperidine-1-carboxylate compound with triethylamine (1:3) trihydrochloride (0.178 g, 0.223 mmol) and [Reactants] at rt. The reaction was stirred for 4 hours at room temperature. The reaction was quenched by adding water. The reaction was further partitioned between ethyl acetate and water. The ethyl acetate layer was separated and washed twice by water before dried (Na2SO4), filtered and concentrated. Flash column was performed (eluted with methanol in CH2Cl2 from 0 to 5% to 10%) to obtain the desired product (33.7 mg, 41.9%). MS (ESI)[M+H$^+$]=520.27; 1H NMR (400 MHz, CHLOROFORM-d) δ ppm 10.75 (br. s., 1H) 8.45 (d, J=3.78 Hz, 1H) 8.07 (d, J=5.04 Hz, 1H) 7.40 (d, J=7.05 Hz, 2H) 6.86-7.16 (m, 5 H) 6.00 (d, J=10.83 Hz, 1H) 4.33-4.76 (m, 3H) 3.26 (dd, J=13.85, 11.58 Hz, 1H) 3.03 (br. s., 2H) 2.80 (s, 1H) 2.50-2.66 (m, 1H) 1.82-2.21 (m, 6H) 1.19-1.28

(m, 2H); $^{19}$F NMR (376 MHz, CHLOROFORM-d) δ ppm −138.37−−135.13 (m, 1F)-141.92-139.34 (m, 1F).

Intermediate 78

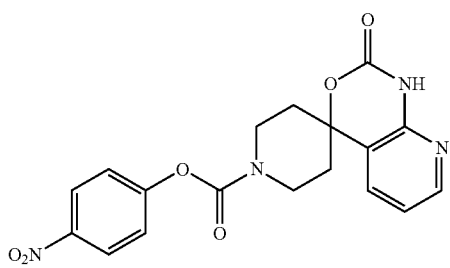

4-Nitrophenyl 2'-oxo-1',2'-dihydrospiro[piperidine-4,4'-pyrido[2,3-d][1,3]oxazine]-1-carboxylate. In a 50 mL round-bottomed flask was spiro[piperidine-4,4'-pyrido[2,3-d][1,3]oxazin]-2'(1'H)-one (187 mg, 0.853 mmol) (azeotroped with dry benzene) and 4-nitrophenyl carbonochloridate (174 mg, 0.861 mmol) in CH2Cl2 (6 mL) to give a tan solution. Et3N (0.238 mL, 1.706 mmol) was added, and the mixture was stirred at rt under nitrogen overnight (4:00 pm) and then over the weekend. The mixture still had some solids. 5 ml CHCl3 was added to dissolve the solids and the clear yellow solution was stirred for another day. TLC showed no starting amine. It was concentrated to dryness and further dried over high vacuum. The residue was then used as it is.

Example 13

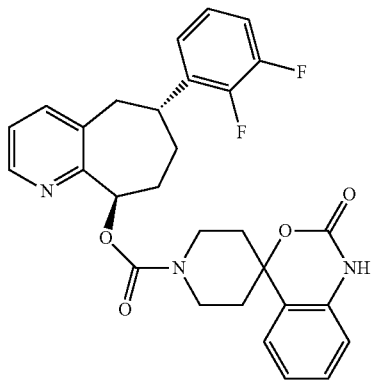

(6,9-Trans)-6-(2,3-difluorophenyl)-6,7,8,9-tetrahydro-5H-cyclohepta[b]pyridin-9-yl 2-oxo-1,2-dihydrospiro[benzo[d][1,3]oxazine-4,4'-piperidine]-1'-carboxylate. In a 100 mL round-bottomed flask was (6,9-trans)-6-(2,3-difluorophenyl)-6,7,8,9-tetrahydro-5H-cyclohepta[b]pyridin-9-ol (79.3 mg, 0.288 mmol) (azeotroped with dry benzene) and 4-nitrophenyl 2'-oxo-1',2'-dihydrospiro[piperidine-4,4'-pyrido[2,3-d][1,3]oxazine-1-carboxylate (221 mg, 0.576 mmol) in THF (5 mL) to give a tan suspension. NaH (69.1 mg, 2.88 mmol) (excess) was added under nitrogen. The mixture was stirred under nitrogen at rt overnight. 17 h: LCMS showed two small peaks with one likely product. It was quenched with water (gas evolves!) and extracted with EtOAc. The layers were separated and the aqueous layer was extracted with EtOAc. The combined organic layers were washed with brine, dried with Na2SO4, and concentrated. Purification by FCC up to 8% MeOH/CH2Cl2 afforded the desired product as a colorless solid (10.8 mg, 7.2%). MS (ESI)[M+H$^+$]=521.39; 1H NMR (400 MHz, CHLOROFORM-d) δ ppm 9.88 (br. s., 1H) 8.23-8.53 (m, 2H) 7.50 (br. s., 1H) 7.36-7.45 (m, 1H) 6.91-7.18 (m, 5H) 5.99 (d, J=10.32 Hz, 1H) 4.39 (br. s., 2H) 3.22-3.71 (m, 3H) 2.90-3.05 (m, 1H) 2.81 (d, J=14.35 Hz, 1H) 1.85-2.55 (m, 6H) 1.67 (s, 2H).

Intermediate 79

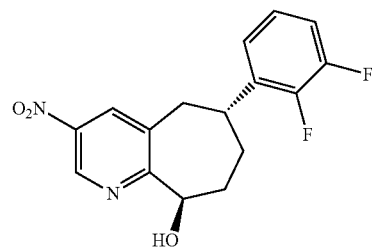

(6R,9R)-6-(2,3-difluorophenyl)-3-nitro-6,7,8,9-tetrahydro-5H-cyclohepta[b]pyridin-9-ol. In a 500 mL round-bottomed flask was (6R,9R)-6-(2,3-difluorophenyl)-6,7,8,9-tetrahydro-5H-cyclohepta[b]pyridin-9-ol (2.912 g, 10.58 mmol) (chiral, azeotroped with dry benzene) and Tetrabutylammonium nitrate (6.44 g, 21.16 mmol) in CH2Cl2 (80 mL) to give a colorless solution. TFAA (3.29 mL, 23.27 mmol) was added dropwise via syringe under nitrogen (3:00 pm). The mixture was stirred at rt overnight (4:00 pm). 17 h: Volatiles were stripped off and the residue was dissolved in 60 ml THF. 15 ml water and LITHIUM HYDROXIDE (1.267 g, 52.9 mmol) were added. The mixture was stirred at rt for 2 h. LCMS showed CF3CO— product was hydrolysed. It was diluted with EtOAc. The layers were separated. The organic layer was washed with brine, dried and concentrated to a tan oil. Purification by FCC up to 50% EtOAc/hexane afforded a less polar peak (likely nitrate ester by 1H NMR), sm (0.54 g, 18.5%), and product (376 mg, 11%). MS (ESI)[M+H$^+$]= 321.11; 1H NMR (400 MHz, CHLOROFORM-d) δ ppm 9.29 (d, J=2.27 Hz, 1H) 8.32 (d, J=2.27 Hz, 1H) 7.00-7.18 (m, 3H) 5.48 (d, J=3.02 Hz, 1H) 5.06 (d, J=11.58 Hz, 1H) 3.28-3.44 (m, 1H) 2.88-3.08 (m, 2H) 2.36-2.48 (m, 1H) 2.16-2.34 (m, 2H) 1.66-1.74 (m, 1H).

Intermediate 80

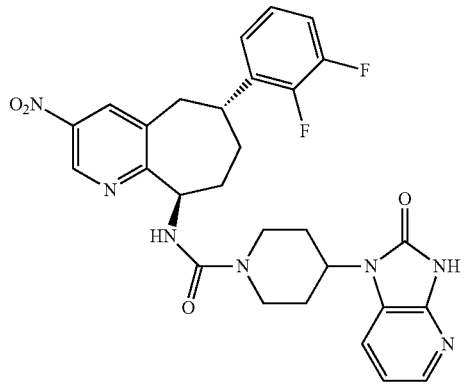

N-((6R,9R)-6-(2,3-difluorophenyl)-3-nitro-6,7,8,9-tetrahydro-5H-cyclohepta[b]pyridin-9-yl)-4-(2-oxo-2,3-dihydro-1H-imidazo[4,5-b]pyridin-1-yl)piperidine-1-carboxamide. In a 100 mL round-bottomed flask was (6R,9R)-6-(2,3-difluorophenyl)-3-nitro-6,7,8,9-tetrahydro-5H-cyclohepta[b]pyridin-9-ol (76.3 mg, 0.238 mmol) (azeotroped with dry benzene) and 4-nitrophenyl 4-(2-oxo-2,3-dihydro-1H-imidazo[4,5-b]pyridin-1-yl)piperidine-1-carboxylate (285 mg, 0.357 mmol) in THF (4 mL) to give a yellow suspension. NaH (57.2 mg, 2.382 mmol) (excess) was added at rt under nitrogen. The mixture was stirred under nitrogen at r.t. for 4 h. The reaction was slowly quenched with water and extracted with EtOAc. The layer was separated. The organic layer was washed with brine, dried and concentrated. The dark oil was purified by FCC up to 10% MeOH/CH2Cl2. The desired product as a major peak was concentrated to a light orange solid (17.1 mg, 13%). MS (ESI)[M+H$^+$]=565.03.

Example 14

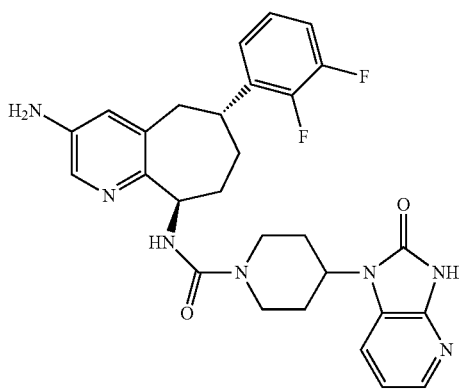

N-((6R,9R)-3-amino-6-(2,3-difluorophenyl)-6,7,8,9-tetrahydro-5H-cyclohepta[b]pyridin-9-yl)-4-(2-oxo-2,3-dihydro-1H-imidazo[4,5-b]pyridin-1-yl)piperidine-1-carboxamide. In a 100 mL round-bottomed flask was (6R,9R)-6-(2,3-difluorophenyl)-3-nitro-6,7,8,9-tetrahydro-5H-cyclohepta[b]pyridin-9-yl 4-(2-oxo-2,3-dihydro-1H-imidazo[4,5-b]pyridin-1-yl)piperidine-1-carboxylate (17.1 mg, 0.030 mmol) in MeOH (2 mL) to give a tan suspension. Pd/C (17 mg, 0.016 mmol) was added, and the mixture was stirred under hydrogen (balloon) for 4 h (10:30 am). LCMS indicated complete conversion. It was filtered and concentrated. The residue was purified by FCC up to 10% MeOH/CH2Cl2 to afford the desired product as a white solid (7.0 mg, 39%). MS (ESI)[M+H$^+$]=535.05; 1H NMR (400 MHz, CHLOROFORM-d) δ ppm 10.05 (br. s., 1H) 8.05-8.15 (m, 1H) 8.00 (br. s., 1H) 7.36-7.59 (m, 1H) 7.28 (s, 1H) 6.91-7.13 (m, 4H) 5.97 (d, J=10.32 Hz, 1H) 4.28-4.80 (m, 3H) 3.54-4.04 (m, 1H) 3.16-3.36 (m, 1H) 3.04 (br. s., 3H) 2.76 (d, J=14.35 Hz, 1H) 2.23-2.44 (m, 2H) 2.05-2.23 (m, 3H) 1.77-2.05 (m, 4H).

Intermediate 81

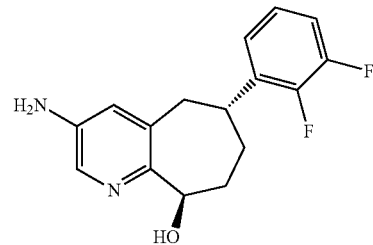

(6R,9R)-3-Amino-6-(2,3-difluorophenyl)-6,7,8,9-tetrahydro-5H-cyclohepta[b]pyridin-9-ol. The mixture of Pd/C (37 mg, 0.035 mmol) and (6R,9R)-6-(2,3-difluorophenyl)-3-nitro-6,7,8,9-tetrahydro-5H-cyclohepta[b]pyridin-9-ol (300 mg, 0.937 mmol) in methanol (10 mL) was hydrogenated under H2 (balloon) for 4 h. LCMS showed the reaction was over. The reaction was filtered through a celite plug. The filtrate was concentrated to give the crude product. MS (ESI)[M+H$^+$]=291.29; 1H NMR (400 MHz, CHLOROFORM-d) δ ppm 7.84 (br. s., 1H) 7.02 (br. s., 3H) 6.79 (br. s., 1H) 5.90 (br. s., 1H) 4.74 (d, J=10.32 Hz, 1H) 3.87 (br. s., 2H) 3.06 (t, J=12.34 Hz, 1H) 2.86 (br. s., 1H) 2.62 (d, J=13.85 Hz, 1H) 2.26 (d, J=12.34 Hz, 1 H) 1.96-2.12 (m, 3H) 1.52 (br. s., 1H).

Intermediate 82

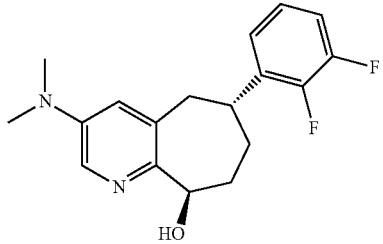

(6R,9R)-6-(2,3-Difluorophenyl)-3-(dimethylamino)-6,7,8,9-tetrahydro-5H-cyclohepta[b]pyridin-9-ol. SODIUM CYANOBOROHYDRIDE (242 mg, 3.86 mmol) was added to the Acetonitrile (2 mL) solution of (6R,9R)-3-amino-6-(2,3-difluorophenyl)-6,7,8,9-tetrahydro-5H-cyclohepta[b]pyridin-9-ol (56 mg, 0.193 mmol) and FORMALDEHYDE (1 mL, 13.43 mmol) at rt. The reaction was stirred at room temperature for 4 hours. ACETIC ACID (0.5 mL, 8.73 mmol) was added to the reaction mixture (Caution: heat generation was observed to cause acetonitrile reflux) and the reaction was stirred overnight. Volatile was removed mostly via vacuum and the crude was added NaOH (1N), extracted with ethyl acetate twice. The ethyl acetate layer was dried (Na2SO4), filtered and concentrated. Flash column by metha-

Example 15

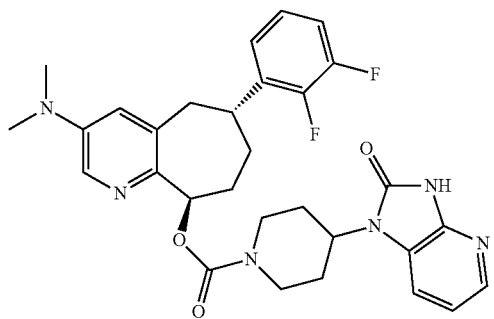

(6R,9R)-6-(2,3-difluorophenyl)-3-(dimethylamino)-6,7,8,9-tetrahydro-5H-cyclohepta[b]pyridin-9-yl 4-(2-oxo-2,3-dihydro-1H-imidazo[4,5-b]pyridin-1-yl)piperidine-1-carboxylate. (6R,9R)-6-(2,3-Difluorophenyl)-3-(dimethylamino)-6,7,8,9-tetrahydro-5H-cyclohepta[b]pyridin-9-ol (27.6 mg, 0.087 mmol) with stirring bar was azeotroped by benzene. Sodium hydride (20.80 mg, 0.867 mmol) was added to the THF (3 mL) suspension of (6R,9R)-6-(2,3-difluorophenyl)-3-(dimethylamino)-6,7,8,9-tetrahydro-5H-cyclohepta[b]pyridin-9-ol (27.6 mg, 0.087 mmol) and 4-nitrophenyl 4-(2-oxo-2,3-dihydro-1H-imidazo[4,5-b]pyridin-1-yl)piperidine-1-carboxylate (43.2 mg, 0.113 mmol). The reaction was stirred at this temperature overnight. The reaction was quenched by water and partitioned between ethyl acetate and water. The ethyl acetate layer was washed by water two more times before dried (Na2SO4), filtered and concentrated. Flash column by methanol in CH2Cl2 from 0 to 4% to 8% gave the desired product (19.8 mg, 36%). MS (ESI)[M+H$^+$]=563.35; 1H NMR (500 MHz, CHLOROFORM-d) δ ppm 10.30 (br. s., 1H) 8.08 (d, J=5.49 Hz, 1 H) 7.95-8.05 (m, 1H) 7.37-7.53 (m, 1H) 6.94-7.14 (m, 4H) 6.79 (br. s., 1H) 6.00 (d, J=10.38 Hz, 1H) 4.66 (br. m., 3H) 3.32 (t, J=12.67 Hz, 1H) 3.08 (br. m., 2 H) 2.91-3.02 (m, 6H) 2.29 (d, J=13.73 Hz, 2H) 2.13-2.24 (m, 2H) 1.86-2.07 (m, 2H) 1.20-1.40 (m, 3H) 0.75-0.98 (m, 1H).

Intermediate 83

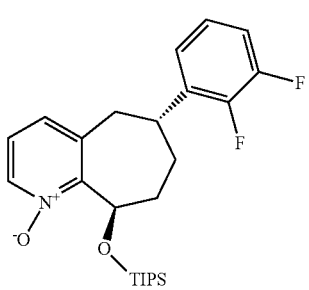

(6R,9R)-6-(2,3-Difluorophenyl)-9-(triisopropylsilyloxy)-6,7,8,9-tetrahydro-5H-cyclohepta[b]pyridine 1-oxide. mCPBA (1.239 g, 5.53 mmol) was added to the CH2Cl2 (30 mL) solution of (6R,9R)-6-(2,3-difluorophenyl)-9-(triisopropylsilyloxy)-6,7,8,9-tetrahydro-5H-cyclohepta[b]pyridine (2.17 g, 5.03 mmol) at rt. The reaction was stirred at room temperature overnight. The solvent was removed via vacuum. The product was purified by flash column eluted with ethyl acetate in hexane from 0 to 50% to 85%. The product was obtained by flushing the column with 85% ethyl acetate in hexane (1.572 g, 69%). MS (ESI)[M+H$^+$]=448.21; 1H NMR (400 MHz, CHLOROFORM-d) δ ppm 8.14 (br. s., 1H) 6.94-7.11 (m, 2H) 6.84-6.92 (m, 2H) 6.66-6.72 (m, 1H) 6.42 (t, J=4.28 Hz, 1H) 4.04 (dd, J=14.73, 4.41 Hz, 1H) 3.73-3.88 (m, 1H) 2.96 (dd, J=14.48, 5.41 Hz, 1H) 2.50 (d, J=5.79 Hz, 1H) 2.13-2.25 (m, 2H) 1.80-1.94 (m, 1H) 1.18-1.32 (m, 3H) 1.09 (d, J=7.55 Hz, 9H) 1.00 (d, J=7.55 Hz, 9H).

Intermediate 84

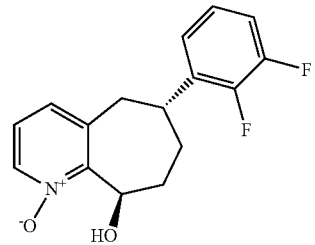

(6R,9R)-6-(2,3-Difluorophenyl)-9-hydroxy-6,7,8,9-tetrahydro-5H-cyclohepta[b]pyridine 1-oxide. TBAF (4.18 mL, 4.18 mmol) was added to the THF (10 mL) solution of (6R,9R)-6-(2,3-difluorophenyl)-9-(triisopropylsilyloxy)-6,7,8,9-tetrahydro-5H-cyclohepta[b]pyridine 1-oxide (1.56 g, 3.48 mmol) at rt. The reaction was stirred at room temperature for 2 hours and LCMS showed that the reaction was completed. The solvent was removed via vacuum and the crude was load to flash column and eluted with methanol in CH2Cl2 from 0 to 10% to afford the desired product (0.7662 g, 75%) as a yellow solid. MS (ESI)[M+H$^+$]=292.10; 1H NMR (400 MHz, CHLOROFORM-d) δ ppm 8.16-8.26 (m, 1H) 7.14-7.20 (m, 1H) 6.98-7.12 (m, 3H) 6.90 (td, J=7.55, 1.76 Hz, 1H) 5.38-5.48 (m, 1H) 3.24-3.47 (m, 2 H) 3.02 (dd, J=14.60, 1.76 Hz, 1H) 2.27-2.44 (m, 3H) 1.79-1.94 (m, 1H).

Intermediate 85

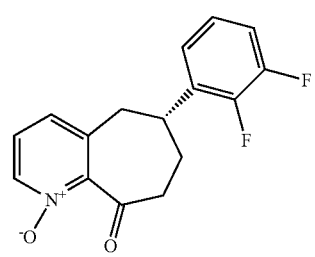

(R)-6-(2,3-Difluorophenyl)-9-oxo-6,7,8,9-tetrahydro-5H-cyclohepta[b]pyridine 1-oxide. Dess-MartinPeriodinane (1.227 g, 2.89 mmol) was added to the CH2Cl2 (8 mL) solution of (6R,9R)-6-(2,3-difluorophenyl)-9-hydroxy-6,7,8,9-tetrahydro-5H-cyclohepta[b]pyridine 1-oxide (0.7662 g, 2.63 mmol) at rt. The reaction was stirred at rt for 1 hour. The reaction was directly load to a column and separated with 10% methanol in CH2Cl2 (0 to 10% gradient) (0.54 g, 42%). MS (ESI)[M+H$^+$]=290.03.

Intermediate 86

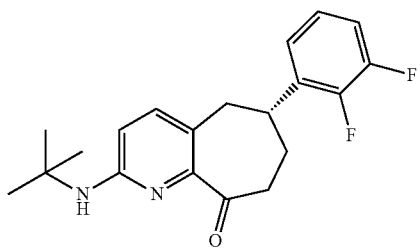

(R)-2-(tert-Butylamino)-6-(2,3-difluorophenyl)-7,8-dihydro-5H-cyclohepta[b]pyridin-9(6H)-one. At 0° C., the 4-methylbenzenesulfonic anhydride (0.930 g, 2.85 mmol) was added to the trifluoro-toluene (3 mL)/CH2Cl2 (3.00 mL) suspension of (R)-6-(2,3-difluorophenyl)-9-oxo-6,7,8,9-tetrahydro-5H-cyclohepta[b]pyridine 1-oxide (0.412 g, 1.424 mmol) and 2-methylpropan-2-amine (0.604 mL, 5.70 mmol). The reaction was stirred at 0° C. for 30 min before diluted with ethyl acetate. The crude was washed by NaOH (1N) twice and the ethyl acetate layer was separated, dried (Na2SO4), filtered and concentrated. Flash column by ethyl acetate in hexane from 0 to 40% to 60% gave the desired product (0.1861 g, 38%). MS (ESI)[M+H$^+$]=345.1; 1H NMR (400 MHz, CHLOROFORM-d) δ ppm 7.18 (d, J=8.56 Hz, 1H) 6.95-7.10 (m, 2H) 6.82-6.95 (m, 1H) 6.60 (d, J=8.56 Hz, 1H) 4.95 (br. s., 1H) 3.45-3.58 (m, 1H) 2.91-3.05 (m, 3H) 2.73-2.85 (m, 1H) 2.13-2.27 (m, 1H) 1.95-2.11 (m, 1H) 1.43 (s, 9H).

Intermediate 87

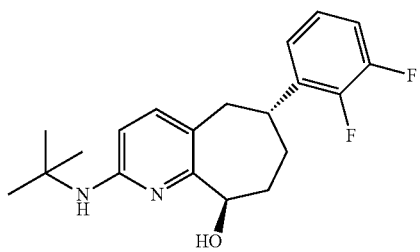

(6R,9R)-2-(tert-Butylamino)-6-(2,3-difluorophenyl)-6,7,8,9-tetrahydro-5H-cyclohepta[b]pyridin-9-ol. SODIUM BOROHYDRIDE (0.072 g, 1.893 mmol) was added to the MeOH (10 mL) solution of (R)-2-(tert-butylamino)-6-(2,3-difluorophenyl)-7,8-dihydro-5H-cyclohepta[b]pyridin-9 (6H)-one (0.2173 g, 0.631 mmol) at rt. The reaction was stirred at room temperature for 1 hour. LCMS showed the reaction was finished. The solvent was removed via vacuum. The crude was separated via flash column eluted with ethyl acetate in hexane from 0 to 35% to 65% to give two compounds. This is the less polar compound (134.9 mg, 61%). HPLC t$_R$=2.43 min; MS (ESI)[M+H$^+$]=347.33; 1H NMR (400 MHz, CHLOROFORM-d) δ ppm 7.18 (d, J=8.06 Hz, 1H) 6.99-7.11 (m, 3H) 6.28 (d, J=8.06 Hz, 1H) 4.76 (dd, J=11.33, 2.01 Hz, 1H) 4.53 (br. s., 1H) 3.03 (d, J=13.85 Hz, 1H) 2.89 (d, J=4.28 Hz, 1H) 2.64 (d, J=14.10 Hz, 1H) 2.28 (dd, J=12.59, 2.01 Hz, 1H) 2.13 (dd, J=9.82, 3.78 Hz, 2H) 1.58-1.71 (m, 1H) 1.42-1.55 (m, 9H).

Intermediate 88

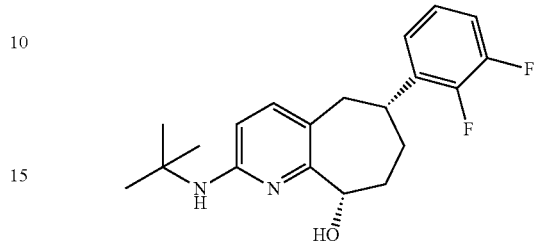

(6R,9S)-2-(tert-Butylamino)-6-(2,3-difluorophenyl)-6,7,8,9-tetrahydro-5H-cyclohepta[b]pyridin-9-ol. This is the more polar compound from above reaction (51.1 mg, 23%). HPLC t$_R$=2.31 min; MS (ESI)[M+H$^+$]=347.33; 1H NMR (400 MHz, CHLOROFORM-d) δ ppm 6.85-7.10 (m, 3H) 6.72-6.79 (m, 1H) 6.24 (d, J=8.31 Hz, 1H) 4.84 (dd, J=9.69, 3.15 Hz, 1H) 4.40-4.56 (m, 1H) 3.44-3.56 (m, 1H) 2.92-3.07 (m, 2H) 2.14-2.25 (m, 1H) 2.05-2.13 (m, 2H) 1.84-1.99 (m, 1H) 1.38-1.55 (s, 9H).

Example 16

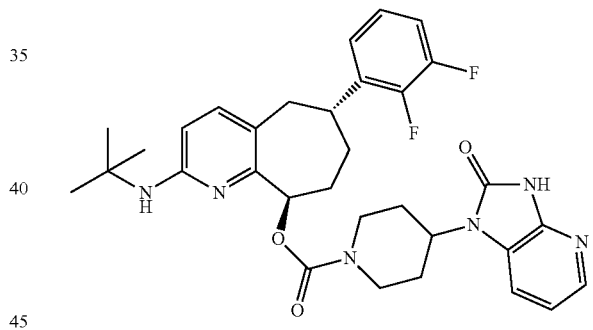

(6R,9R)-2-(tert-Butylamino)-6-(2,3-difluorophenyl)-6,7,8,9-tetrahydro-5H-cyclohepta[b]pyridin-9-yl 4-(2-oxo-2,3-dihydro-1H-imidazo[4,5-b]pyridin-1-yl)piperidine-1-carboxylate. (6R,9R)-2-(tert-butylamino)-6-(2,3-difluorophenyl)-6,7,8,9-tetrahydro-5H-cyclohepta[b]pyridin-9-ol (69.1 mg, 0.199 mmol) with stirring bar was azeotroped by benzene. Sodium hydride (47.9 mg, 1.995 mmol) was added to the THF (3 mL) suspension of (6R,9R)-2-(tert-butylamino)-6-(2,3-difluorophenyl)-6,7,8,9-tetrahydro-5H-cyclohepta[b]pyridin-9-ol (69.1 mg, 0.199 mmol) and 4-nitrophenyl 4-(2-oxo-2,3-dihydro-1H-imidazo[4,5-b]pyridin-1-yl)piperidine-1-carboxylate compound with triethylamine (1:3) trihydrochloride (238 mg, 0.299 mmol) at rt. The reaction was stirred at room temperature overnight. The reaction was quenched by water and partitioned between ethyl acetate and water. The ethyl acetate layer was washed by water twice before dried (Na2SO4), filtered and concentrated. Flash column by methanol in CH2Cl2 from 0 to 10% gave the desired product as a white solid. The product was further purified by prep HPLC (69.2 mg, 26%). 1H NMR (500 MHz, CHLOROFORM-d) δ ppm 8.07 (d, J=5.19 Hz, 1H) 7.34-7.44 (m, 1H) 6.96-7.15 (m, 4H) 6.08-6.28 (m, 1H) 5.83-5.99 (m, 1 H) 4.42-4.77 (m, 3H) 3.16-3.25 (m, 1H) 2.86-3.14 (m, 3H) 2.62-2.72 (m, 1H) 2.11-2.38 (m, 5H) 1.94 (d, J=11.90 Hz, 3H) 1.52-1.60 (m, 1H) 1.46 (s, 9H).

Example 17

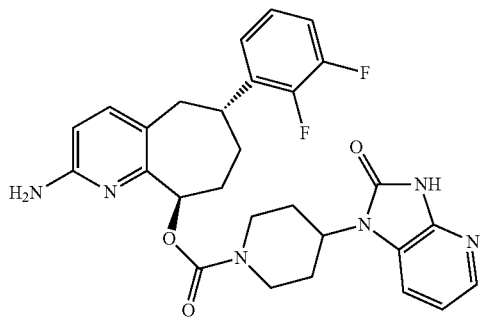

(6R,9R)-2-Amino-6-(2,3-difluorophenyl)-6,7,8,9-tetrahydro-5H-cyclohepta[b]pyridin-9-yl 4-(2-oxo-2,3-dihydro-1H-imidazo[4,5-b]pyridin-1-yl)piperidine-1-carboxylate. The mixture of (6R,9R)-2-(tert-butylamino)-6-(2,3-difluorophenyl)-6,7,8,9-tetrahydro-5H-cyclohepta[b]pyridin-9-yl 4-(2-oxo-2,3-dihydro-1H-imidazo[4,5-b]pyridin-1-yl)piperidine-1-carboxylate (0.1537 g, 0.117 mmol) and TFA (4 mL, 1.18E+04 mmol) was heat to 70° C. for 1 hour. LCMS showed that most of the starting material was converted to the desired product. There was no sign of hydrolysis of the carbamate to alcohol. TFA was removed via vacuum and the crude was partitioned between ethyl acetate and NaOH (1N). The ethyl acetate layer was separated, dried (Na2SO4), filtered and concentrated. Flash column by methanol in CH2Cl2 from 0 to 3.5% to 5%. At this point the desired product was not eluted out. The flash column was continued to eluted with 5% methanol in CH2Cl2 to gave the desired product as a white solid (64.8 mg, 90%). MS (ESI)[M+H$^+$]=535; 1H NMR (400 MHz, CHLOROFORM-d) δ ppm 11.44 (br. s., 1H) 8.13 (d, J=4.53 Hz, 1H) 7.36 (br. s., 1H) 7.14-7.24 (m, 1H) 6.99-7.10 (m, 4H) 6.37 (d, J=7.55 Hz, 1H) 5.87 (d, J=10.32 Hz, 1H) 5.57 (d, J=1.51 Hz, 1H) 4.48-4.83 (m, 2H) 4.17 (br. s., 1H) 3.23 (dd, J=13.72, 11.96 Hz, 1H) 2.95 (d, J=10.32 Hz, 3H) 2.69 (d, J=14.10 Hz, 2H) 2.08-2.31 (m, 3H) 1.83-2.08 (m, 3H) 1.19-1.35 (m, 1H) 0.81-0.95 (m, 1H).

Example 18

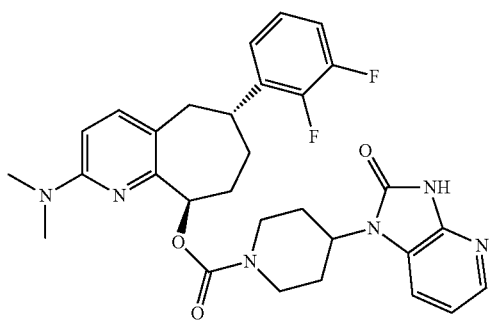

(6R,9R)-6-(2,3-difluorophenyl)-2-(dimethylamino)-6,7,8,9-tetrahydro-5H-cyclohepta[b]pyridin-9-yl 4-(2-oxo-2,3-dihydro-1H-imidazo[4,5-b]pyridin-1-yl)piperidine-1-carboxylate. SODIUM CYANOBOROHYDRIDE (108 mg, 1.721 mmol) was added to the Acetonitrile (2 mL) solution of (6R,9R)-2-amino-6-(2,3-difluorophenyl)-6,7,8,9-tetrahydro-5H-cyclohepta[b]pyridin-9-yl 4-(2-oxo-2,3-dihydro-1H-imidazo[4,5-b]pyridin-1-yl)piperidine-1-carboxylate (46 mg, 0.086 mmol) and FORMALDEHYDE (1 mL, 13.43 mmol) at rt. The reaction was stirred at room temperature for 4 hours. ACETIC ACID (0.5 mL, 8.73 mmol) was added to the reaction mixture and the reaction was stirred overnight. Volatile was removed mostly via vacuum and the crude was added NaOH (1N) and stirred at room temperature for 1 hour before extract with ethyl acetate. The ethyl acetate layer was dried (Na2SO4), filtered and concentrated. Flash column by methanol in CH2Cl2 from 0 to 4% to 8% gave the desired product (19.8 mg, 39%). MS (ESI)[M+H$^+$]=563.42.

Example 19

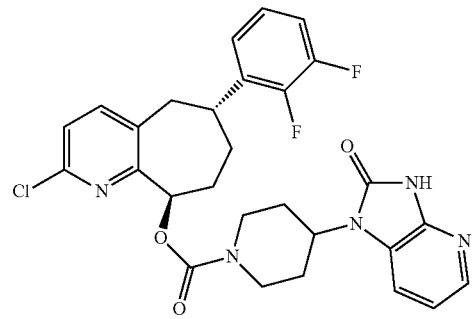

(6R,9R)-2-Chloro-6-(2,3-difluorophenyl)-6,7,8,9-tetrahydro-5H-cyclohepta[b]pyridin-9-yl 4-(2-oxo-2,3-dihydro-1H-imidazo[4,5-b]pyridin-1-yl)piperidine-1-carboxylate. To the mixture of (6R,9R)-2-amino-6-(2,3-difluorophenyl)-6,7,8,9-tetrahydro-5H-cyclohepta[b]pyridin-9-yl 4-(2-oxo-2,3-dihydro-1H-imidazo[4,5-b]pyridin-1-yl)piperidine-1-carboxylate (45 mg, 0.084 mmol), HYDROCHLORIC ACID (3 mL, 36.5 mmol) was added COPPER(I) CHLORIDE (16.67 mg, 0.168 mmol) and SODIUM NITRATE (21.47 mg, 0.253 mmol) at −5° C. The reaction was stirred at this temperature for 1 hour and stirred at room temperature for 1 hour. NaOH (1N) was added to the reaction mixture before extract with ethyl acetate twice. The ethyl acetate layer was washed by brine before separated, dried (Na2SO4), filtered and concentrated. Flash column by methanol in CH2Cl2 from 0 to 4% to 8% to give the desired product (6.4 mg, 12%). MS (ESI)[M+H$^+$]=554.09.

Intermediate 89

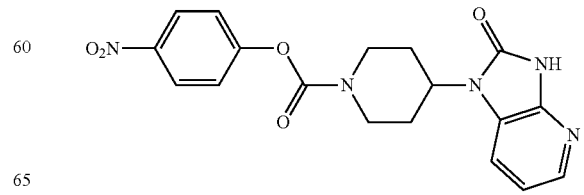

4-Nitrophenyl 4-(2-oxo-2,3-dihydro-1H-imidazo[4,5-b]pyridin-1-yl)piperidine-1-carboxylate. The mixture of 2-oxo-1-(piperidinium-4-yl)-2,3-dihydro-1H-imidazo[4,5-b]pyridin-4-ium chloride (10.41 g, 35.8 mmol) in THF (300 mL) and DMF (167 mL) was stirred at rt for 10 min under N2. The reaction mixture is still a suspension at this time. 4-methylmorpholine (27.5 mL, 250 mmol) was added slowly to the reaction mixture. The internal reaction temperature became 22° C. (from 20° C.). The reaction stirred for another 10 min before 4-nitrophenyl 4-(2-oxo-2,3-dihydro-1H-imidazo[4,5-b]pyridin-1-yl)piperidine-1-carboxylate was added in one portion at room temperature. The reaction temperature increased to 27° C. The reaction was stirred for 2 hours. 1000 mL of water was added slowly to the reaction mixture and all the suspension was dissolved, then the solution became cloudy. The reaction was stirred at room temperature overnight. The reaction was filtered and the solid was washed by water and CH3CN. The product was combined with 79044-022 as an off white powder (7.4 g, 54%) and was used as is.

Example 20

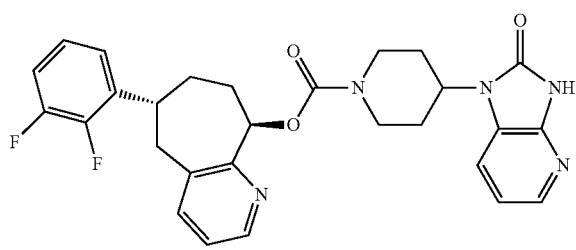

(6R,9R)-2-Chloro-6-(2,3-difluorophenyl)-6,7,8,9-tetrahydro-5H-cyclohepta[b]pyridin-9-yl 4-(2-oxo-2,3-dihydro-1H-imidazo[4,5-b]pyridin-1-yl)piperidine-1-carboxylate. In an oven-dried 1 L round-bottomed flask was (6R,9R)-6-(2,3-difluorophenyl)-6,7,8,9-tetrahydro-5H-cyclohepta[b]pyridin-9-ol (12.74 g, 46.3 mmol) (>99.9% purity) and 4-nitrophenyl 4-(2-oxo-2,3-dihydro-1H-imidazo[4,5-b]pyridin-1-yl)piperidine-1-carboxylate (26.6 g, 69.4 mmol) in DMF (200 mL) to give a light yellow suspension under nitrogen. After cooling to −15° C. with MeOH-ice bath, NaHMDS (139 mL, 139 mmol) was added dropwise. After the gel was formed (addition of 1.5 equiv. base), the cooling bath was removed and the remaining base was added dropwise. The mixture was stirred under nitrogen at rt for 2 h. LCMS showed complete conversion. 3 h: It was quenched with saturated NaHCO3 solution (400 ml). The suspension was partitioned between 500 ml water and 700 ml EtOAc. The layers were separated and the aqueous layer was extracted with EtOAc (2×250 ml). No product left in aqueous by LCMS. The combined organic layers were washed with 300 ml saturated NaHCO3, 2×300 ml water, 300 ml brine, dried over Na2SO4, and concentrated to a yellow foam/solid. The crude product was purified by FCC (c.a. 900 g silica gel) up to 4% MeOH/CH2Cl2. The resulted product as a tan solid was further purified by recrystallization from iPrOH (21.64 g, 90%) as a white crystalline powder (submitted for HPLC-MS analysis: 99.2%, and ee evaluation: 100% ee); mp 248° C.

Single Crystal X-Ray Measurements. A Bruker APEX2 Kappa CCD diffractometer equipped with a rotating anode generator of Cu Kα radiation, (λ=1.54178 Å) was used to collect diffraction data at the room temperature. Indexing and processing of the measured intensity data were carried out with the APEX2 software package/program suite (APEX2 Data collection and processing user interface: APEX2 User Manual, v1.27; BRUKER AXS, INc., 5465 East Cheryl Parkway, Madison, Wis. 53711 USA). The final unit cell parameters were determined using the entire data set.

The structure was solved by direct methods and refined by the full-matrix least-squares techniques, using the SHELXTL software package (Sheldrick, G M. 1997, SHELXTL. Structure Determination Programs. Version 5.10, Bruker AXS, Madison, Wis., USA.). The function minimized in the refinements was $\Sigma w(|F_o|-|F_c|)^2$. R is defined as $\Sigma||F_o|-|F_c||/\Sigma|F_o|$ while $R_w=[\Sigma_w(|F_o|-|F_c|)^2/\Sigma_w|Fo|^2]^{1/2}$, where w is an appropriate weighting function based on errors in the observed intensities. Difference Fourier maps were examined at all stages of refinement. All non-hydrogen atoms were refined with anisotropic thermal displacement parameters. The hydrogen atoms associated with hydrogen bonding were located in the final difference Fourier maps while the positions of the other hydrogen atoms were calculated from an idealized geometry with standard bond lengths and angles. They were assigned isotropic temperature factors and included in structure factor calculations with fixed parameters.

The crystal data of the compound of example 20 is shown below. The fractional atomic coordinates are listed in Table 2. It should be understood by one of ordinary skill in the art that slight variations in the coordinates are possible and are considered to be within the scope the present disclosure. Temperature: room temperature; Wavelength: 0.71070; Crystal system, space group: Orthorhombic, P2(1)2(1)2(1); Unit cell dimensions: a=7.5941(1) Å, alpha=90 deg.; b=13.8789(2) Å, beta=90 deg.; c=24.7319(3) Å, gamma=90 deg.; Volume: 2606.69(6) Å$^3$; Z, Calculated density: 4, 1.324 Mg/m$^3$.

| Atom | X | Y | Z | U(eq) |
|---|---|---|---|---|
| O(1) | −3138(3) | −3128(1) | −795(1) | 52(1) |
| O(2) | −4445(3) | −2737(1) | −1587(1) | 59(1) |
| O(3) | 874(3) | −7046(2) | −2345(1) | 76(1) |
| N(1) | −249(3) | −2383(2) | −1185(1) | 59(1) |
| N(2) | −3324(3) | −4230(2) | −1451(1) | 58(1) |
| N(3) | 752(3) | −5384(2) | −2444(1) | 59(1) |
| N(4) | 2908(4) | −6179(2) | −2849(1) | 60(1) |
| N(5) | 4345(4) | −4861(2) | −3287(1) | 67(1) |
| F(1) | −5198(4) | 864(2) | −133(1) | 120(1) |
| F(2) | −6096(7) | 2376(2) | 450(2) | 169(2) |
| C(1) | −4103(7) | 1133(3) | 266(1) | 86(1) |
| C(2) | −4607(9) | 1936(3) | 572(2) | 110(2) |
| C(3) | −3566(11) | 2247(3) | 987(2) | 117(2) |
| C(4) | −2071(10) | 1750(4) | 1105(2) | 115(2) |
| C(5) | −1557(6) | 961(3) | 798(2) | 88(1) |
| C(6) | −2606(5) | 631(2) | 368(1) | 69(1) |
| C(7) | −2092(4) | −273(2) | 61(1) | 60(1) |
| C(8) | −1890(5) | −73(2) | −550(1) | 66(1) |
| C(9) | −732(4) | −785(2) | −837(1) | 59(1) |
| C(10) | 892(5) | −517(3) | −1040(1) | 75(1) |
| C(11) | 1939(5) | −1169(3) | −1310(1) | 76(1) |
| C(12) | 1308(4) | −2088(3) | −1376(1) | 66(1) |
| C(13) | −1215(4) | −1750(2) | −914(1) | 51(1) |
| C(14) | −2915(4) | −2126(2) | −662(1) | 50(1) |
| C(15) | −2877(4) | −2071(2) | −46(1) | 54(1) |
| C(16) | −3363(4) | −1096(2) | 186(1) | 60(1) |
| C(17) | −3664(3) | −3316(2) | −1307(1) | 49(1) |

| Atom | X | Y | Z | U(eq) |
|---|---|---|---|---|
| C(18) | −3817(4) | −4559(2) | −1991(1) | 66(1) |
| C(19) | −2208(4) | −4617(2) | −2360(1) | 67(1) |
| C(20) | −805(4) | −5238(2) | −2104(1) | 60(1) |
| C(21) | −320(4) | −4856(2) | −1544(1) | 60(1) |
| C(22) | −1952(5) | −4816(2) | −1191(1) | 65(1) |
| C(23) | 1452(4) | −6298(2) | −2527(1) | 59(1) |
| C(24) | 3110(4) | −5225(2) | −2978(1) | 54(1) |
| C(25) | 4272(5) | −3902(3) | −3342(2) | 79(1) |
| C(26) | 3046(6) | −3334(3) | −3100(2) | 85(1) |
| C(27) | 1738(5) | −3728(2) | −2770(2) | 73(1) |
| C(28) | 1776(4) | −4716(2) | −2715(1) | 56(1) |

Example 21

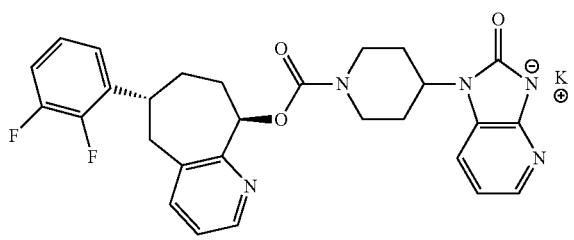

Potassium 1-(1-(((6R,9R)-6-(2,3-difluorophenyl)-6,7,8,9-tetrahydro-5H-cyclohepta[b]pyridin-9-yloxy)carbonyl)piperidin-4-yl)-2-oxo-1,2-dihydroimidazo[4,5-b]pyridin-3-ide. In an oven-dried 100 mL round-bottomed flask was (6R,9R)-6-(2,3-difluorophenyl)-6,7,8,9-tetrahydro-5H-cyclohepta[b]pyridin-9-yl 4-(2-oxo-2,3-dihydro-1H-imidazo[4,5-b]pyridin-1-yl)piperidine-1-carboxylate (1.08 g, 2.079 mmol) in Ethanol (10 mL) to give a colorless solution. POTASSIUM TERT-BUTOXIDE (0.233 g, 2.079 mmol) was added in one portion. Heat-gun was used to slightly heat the solution with swirling until the solids were completely dissolved. Volatiles were stripped off to a white foam/powder. The powder was further dried under high vacuum with occasional warm at 50° C. bath then at rt under high vacuum over 3 days. LCMS and HPLC were obtained. HPLC showed 98% purity with no single purity >0.5%. 1H NMR (400 MHz, d6-DMSO) 8.44 (s, 1H), 7.61-7.55 (m, 2H), 7.31-7.21 (m, 4H), 6.91 (s, 1H), 6.41 (s, 1H), 5.93 (d, J=12 Hz, 1H), 4.38 (br, 2H), 4.11 (br, 1H), 3.50-3.41 (m, 1H), 3.21-2.78 (m, 5H), 2.30-1.50 (m, 7H).

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

We claim:

1. A compound of formula II, or a salt thereof, where Ar¹ is phenyl substituted with 0-3 substituents selected from the group consisting of cyano, halo, alkyl, haloalkyl, alkoxy, haloalkoxy, and alkylSO$_2$, and where R¹ is hydrogen, trialkylsilyl, alkoxy, alkylcarbonyl, benzyl, benzoyl, or pivaloyl

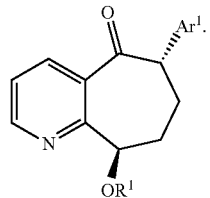

2. The compound of claim 1: (6S,9R)-6-(2,3-difluorophenyl)-9-(triisopropylsilyloxy)-6,7,8,9-tetrahydro-5H-cyclohepta[b]pyridin-5-one

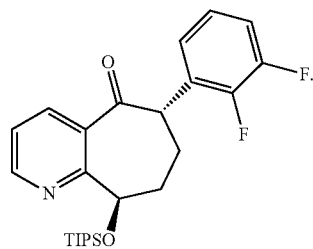

3. A compound of formula III where R¹ is hydrogen, trialkylsilyl, alkoxy, alkylcarbonyl, benzyl, benzoyl, or pivaloyl

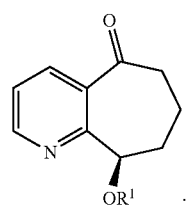

4. The compound of claim 3: (R)-9-(triisopropylsilyloxy)-6,7,8,9-tetrahydro-5H-cyclohepta[b]pyridin-5-one

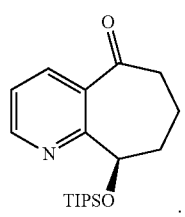

5. The compound (R)-9-hydroxy-6,7,8,9-tetrahydro-5H-cyclohepta[b]pyridin-5-one
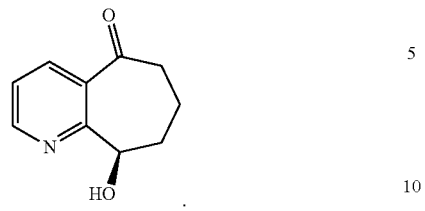
* * * * *